(12) United States Patent
Weiner et al.

(10) Patent No.: US 8,304,234 B2
(45) Date of Patent: *Nov. 6, 2012

(54) COMPOSITIONS AND METHODS FOR DELIVERY OF GENETIC MATERIAL

(75) Inventors: David B. Weiner, Merion Station, PA (US); William V. Williams, Havertown, PA (US); Bin Wang, Beijing (CN)

(73) Assignees: The Trustees of the Universtiy of Pennsylvania, Philadelphia, PA (US); The Wistar Institute, Philadelphia, PA (US)

(*) Notice: Subject to any disclaimer, the term of this patent is extended or adjusted under 35 U.S.C. 154(b) by 1697 days.

This patent is subject to a terminal disclaimer.

(21) Appl. No.: 11/317,548

(22) Filed: Dec. 23, 2005

(65) Prior Publication Data

US 2006/0222629 A1 Oct. 5, 2006

Related U.S. Application Data

(63) Continuation of application No. 09/359,975, filed on Jul. 23, 1999, now Pat. No. 7,001,759, which is a continuation of application No. 08/979,385, filed on Nov. 26, 1997, now Pat. No. 5,981,505, which is a continuation of application No. 08/495,684, filed as application No. PCT/US94/00899 on Jan. 26, 1994, now abandoned, which is a continuation-in-part of application No. 08/125,012, filed on Sep. 21, 1993, now Pat. No. 5,593,972, and a continuation-in-part of application No. 08/124,962, filed on Sep. 21, 1993, now abandoned, and a continuation-in-part of application No. 08/093,235, filed on Jul. 15, 1993, now abandoned, and a continuation-in-part of application No. 08/029,336, filed on Mar. 11, 1993, now abandoned, which is a continuation of application No. 08/008,342, filed on Jan. 26, 1993, now abandoned.

(51) Int. Cl.
| | |
|---|---|
| A61K 31/167 | (2006.01) |
| C12N 15/63 | (2006.01) |
| C12N 15/87 | (2006.01) |
| C07H 21/04 | (2006.01) |

(52) U.S. Cl. .................. 435/320.1; 536/23.1; 536/23.7; 536/23.72; 435/455; 514/615; 514/818; 514/44

(58) Field of Classification Search .......................... None
See application file for complete search history.

(56) References Cited

U.S. PATENT DOCUMENTS

| | | | | |
|---|---|---|---|---|
| 3,688,765 | A | 9/1972 | Gasaway | 604/70 |
| 4,224,404 | A | 9/1980 | Viza et al. | 435/2 |
| 4,394,448 | A | 7/1983 | Szoka, Jr. et al. | 435/172.3 |
| 4,596,556 | A | 6/1986 | Morrow et al. | 604/70 |
| 4,680,027 | A | 7/1987 | Parsons et al. | 604/68 |
| 4,806,463 | A | 2/1989 | Goodchild et al. | 435/5 |
| 4,945,050 | A | 7/1990 | Sanford et al. | 435/172.1 |
| 5,017,487 | A | 5/1991 | Stunnenberg et al. | 435/172.3 |
| 5,024,656 | A | 6/1991 | Gasaway et al. | 604/70 |
| 5,036,006 | A | 7/1991 | Sanford et al. | 435/170.1 |
| 5,185,254 | A | 2/1993 | Linnenbach | 435/172.3 |
| 5,466,676 | A | 11/1995 | Booth et al. | 514/44 |
| 5,593,972 | A | 1/1997 | Weiner et al. | 514/44 |
| 6,214,804 | B1 * | 4/2001 | Felgner et al. | 514/44 |

FOREIGN PATENT DOCUMENTS

| | | | |
|---|---|---|---|
| EP | 0 386 882 | | 9/1990 |
| WO | WO 90/11092 | | 10/1990 |
| WO | WO 91/07425 | | 5/1991 |
| WO | WO 91/09958 | | 7/1991 |
| WO | WO 91/12329 | * | 8/1991 ..................... 435/455 |
| WO | WO 92/20316 | | 11/1992 |
| WO | WO 93/17706 | | 9/1993 |
| WO | WO 93/23552 | | 11/1993 |

OTHER PUBLICATIONS

W. French Anderson in 1998 (Nature, vol. 392, 1998, pp. 25-30).*
Verma et al., Nature, 1997, vol. 389, pp. 239-242.*
Kmiec, 1999, American Scientist, vol. 87, pp. 240-247).*
Mountain, TIBTECH, 2000, vol. 18, pp. 119-128.*
Juengst, BMJ, 2003, vol. 326, pp. 1410-1411.*
Barnett et al., *Conf. Adv. AIDS Vaccine Dev.*, Feb. 11-15, 1996, p. 126, Poster 6.
Bruck et al., "HIV-1 envelope-elicited neutralizing antibody titres correlate with protection and virus load in chimpanzees," *Vaccine*, 1994, 12(12), 1141-1148.
Girard et al., "Failure of a Human Immunodeficiency Virus Type 1 (HIV-1) Subtype B-Derived Vaccine to Prevent Infection of Chimpanzees by an HIV-1 Subtype E Strain," *J. Viol.*, 1996, 70(11), 8229-8233.
Orkin et al., *Report and Recommendations of the Panel to Assess the NIH-Investment in Research on Gene Therapy*, Dec. 7, 1995.
Reitz, M.S., "Letter to the Editor on the Historical Origins of HIV-1 (MN) and (RF)", *AIDS Research and Human Retroviruses*, 1992, 8, 1539-1541.

(Continued)

*Primary Examiner* — Nancy T Vogel
*Assistant Examiner* — Catherine Hibbert
(74) *Attorney, Agent, or Firm* — Pepper Hamilton, LLP

(57) ABSTRACT

Methods of introducing genetic material into cells of an individual and compositions and kits for practicing the same are disclosed. The methods comprise the steps of contacting cells of an individual with a polynucleotide function enhancer and administering to the cells, a nucleic acid molecule that is free of retroviral particles. The nucleic acid molecule comprises a nucleotide sequence that encodes a protein that comprises at least one epitope that is identical or substantially similar to an epitope of a pathogen antigen or an antigen associated with a hyperproliferative or autoimmune disease, a protein otherwise missing from the individual due to a missing, nonfunctional or partially functioning gene, or a protein that produces a therapeutic effect on an individual. Methods of prophylactically and therapeutically immunizing an individual against HIV am disclosed. Pharmaceutical compositions and kits for practicing methods of the present invention are disclosed.

28 Claims, 10 Drawing Sheets

OTHER PUBLICATIONS

Thomason, D.B. et al., "Stable incorporation of a bacterial gene into adult rat skeletal muscle in vivo", *Am. J. Physiology*, 1990, 258(3), C578-C581.

Zolla-Pazner et al., *Int. Conf. AIDS (Canada)*, Jul. 7-12, 1996, 11(1), p. 14, Abstract No. Mo.A.406.

Chaudhary et al., "A Rapid Method of Cloning Functional Variable-Region Antibody Genes in *Escherichia coli* as Single-Chain Immunotoxins", *PNAS USA*, 1990, 87, 1066-1070.

Chen, L. et al., "Human Papillomavirus Type 16 Nucleoprotein E7 is a Tumor Rejection Antigen", *PNAS USA*, 1991, 88, 110-114.

Estin, C.D. et al., "Transfected Mouse Melanoma Lines that Express Vairous Levels of Human Melanoma-Associated Antigen p97", *J. Nat. Can. Institute*, 1989, 81(6), 445-448.

Fendly, B.M. et al., "The Extracellular Domain of HER2/neu is a Potential Immunogen for Active Specific Immunotherapy of Breast Cancer", *J. Biological Response Modifiers*, 1990, 9, 449-455.

Fidler, I. et al., "Biological and Experimental Consequences of the Zonal Composition of Solid Tumors", *Cancer Research*, 1981, 41, 3266-3267.

Fisher et al., "A Molecular Clone of HTLV-III with Biological Activity", *Nature*, 1985, 316, 262-265.

Haynes, B.F., "Scientific and Social Issues of Human Immunodeficiency Virus Vaccine Development", *Science*, 1993, 260, 1279-1286.

Hoffenbach, A. et al., "Unusually High Frequencies of HIV-Specific Cytotoxic T Lymphocytes in Humans", *J. Immunology*, 1989, 142, 452-462.

Howell et al., "Limited T-Cell receptor Beta-Chain heterogeneity Among Interleukin 2 Receptor-Positive Synovial T Cells Suggests a Role for Superantigen in Rheumatoir Arthritis", *PNAS USA*, 1988, 88, 10921-10925.

Kabat et al., "Sequence of Proteins of Immunological Interest", U.S. Dept. of Health and Human Services, bethesda, MD, 1987.

Khoka, R. et al., "Suppression of Invasion by Inducible Expression of Tissue Inhibitor of Metalloproteinase-1 (TIMP-1) in B16-F10 Melanoma Cells", *J. National Cancer Institute*, 1992, 84(13), 1017-1022.

Kundig et al., "Nonimmunogenic Tumor Cells May Efficiently Restimulate Tumor Antigen-Specific Cytotoxic T Cells", *J. Immunology*, 1993, 150, 4450-4456.

Ledley, F., "Clinical Considerations in the Design of Protocols for Somatic Gene Therapy", *Human Gene Therapy*, 1991, 2, 77-83.

McCoy, Bargmann and Weinberg, "Human Colon Carcinoma Kiras2 Oncogene and its Corresponding Proto-Oncogene", *Mol. Cell. Biol.*, 1984, 4, 1577-1582.

Oksenberg et al., "Limited Heterogeneity of Rearranged T-Cell receptor V Alpha Transcripts in Brains of Multiple Sclerosis Patients", *Nature*, 1990, 345, 344-348.

Paliard et al., "Evidence for the Effects of a Superantigen in Rheumatoid Arthritis", *Science*, 1991, 253, 325-329.

Reddel, R.R. et al., "Neoplastic Transformation of Human Mesothelial Cells Transfected with a Mutant c-Ha-*ras* Oncogene", *Proceedings of the 80th Annual Meeting of the American Association for Cancer Research*, May 24-27, 1989, 30, 439, Abs. 1743.

Torpey III, D. et al., "Effects of Adoptive Immunotherapy with Autologous CD8+ T Lymphocytes on Immunologic Parameters: Lymphocyte Subsets and Cytotoxic Activity", *Clinical Immunology and Immunopathology*, 1993, 68(3), 263-272.

Warner, J.F. et al., "Induction of HIV-Specific CTL and Antibody Responses in Mice Using Retroviral Vector-Transduced Cells", *AIDS Res. and Human Retroviruses*, 1991, 7, 645-655.

Williams et al., "Restricted Heterogeneity of T Cell Receptor Transcripts in Rheumatoid Synovium", *J. Clin. Invest.*, 1992, 90, 326-333.

Wucherpfennig et al., "Shared Human T Cell receptor V Beta Usage to Immunodominant Regions of Myelin Basic Protein", *Science*, 1990, 248, 1016-1019.

Brandsma et al., "Use of a Rapid, Efficient Inoculation Method to Induce Papillomas by Cottontail Rabbit Papillomavirus DNA Shows that the E7 Gene is Required", *PNAS USA*, 1991, 88, 4816-4820.

Butini, L. et al., "Comparative Analysis of HIV-Sepcific CTL Activity in Lymphoid Tissue and Peripheral Blood", *J. Cell. Biochem.*, 1994, Suppl 18B, 147, Abst. J 306.

Davis, B.D. et al. (eds.), "Microbiology", 3rd Edition, Harper and Row, Hagerstown, 1980, p. 294.

Feigner, P.L. and Rhodes, "Gene Therapeutics", *Nature*, 1991, 349, 351-352.

Furth, P.A., "Gene Transfer into Somatic Tissues by Jet Injection", *Analytical Biochemistry*, 1992, 205, 365-368.

Garry, R.F. et al., "Detection of a Human Intracisternal A-Type Retroviral Particle Antigenically Related to HIV", *Science*, 1990, 250, 1127-1129.

Knuth, A. et al., "Cellular and Humoral Immune Responses Against Cancer: Implications for Cancer Vaccines", *Curr. Opin. Immunol.*, 1991, 3(5), 659-664.

Reddy et al., "Molecular Cloning of Human T-Cell Lymphotrophic Virus Type I-like Proviral Genome from the Peripheral Lymphocyte DNA of a Patient with Chronic Neurologic Disorders", *PNAS USA*, 1988, 85, 3599-3603.

Ritchie et al., "The Pharmacological Basis of Therapeutics", Gilman et al. (eds.), 8th Edition, Chapter 15, 3111, Jan. 2000.

Wang, B. et al., "Genetic Immunization: A Novel Method for Vaccine Development against HIV", in "Vaccines 93 Modern Approaches to New Vaccines Including Prevention of AIDS", Cold Spring Harbor Laboratory Press, Cold Spring Harbor, New York, 1993, pp. 143-150.

Wang, B. et al., "Gene Inoculation Generates Immune Responses Against Human Immunodeficiency Virus Type 1", *PNAS USA*, 1993, 90, 4156-4160.

Acsadi, G. et al., "Human Dystrophin expression in mdx Mice after Intramuscular Injection of DNA Constructs", *Nature*, 1991, 352, 815-818.

Aldovini et al., "Mutation of RNA and Protein Sequences Involved in Human Immunodeficiency Virus Type 1 Packaging Result in Production of Noninfectious Virus", *J. Virology*, 1990, 64, 1920-1926.

Anderson, W. French, "Prospects for Human Gene Therapy", *Science*, 1984, 226, 401-4091.

Anilionis et al., "Structure of the Glycoprotein Gene in Rabies Virus", *Nature*, 1981, 294, 275-278.

Benoit et al., "Destruction and Regeneration of Skeletal Muscle After Treatment with a Local Anaesthetic, Bupivacaine (Marcaine®)", *J. Anat.*, 1970, 107, 547-556.

Benvenisty et al., "Direct Introduciton of Genes Into Rats and Expression of the Genes", *PNAS USA*, 1986, 83, 9551-9555.

Berman et al., "Protection of Chimpanzees From Infection by HIV-1 After Vaccination with recombinant Glycoprotien gp120 but not gp160", *Nature*, 1990, 345, 622-625.

Brigham et al., "Rapid Communicaiton: In Vivo Transfection of Murine Lungs with a Functioning Prokaryotic Gene Using a Liposome Vehicle", *Am. J. Medical Sciences*, 1989, 298, 278-281.

Chen et al., "HIV-1 gp41 Contains Two Sites for Interaction with Several Proteins on the Helper T-Lymphoid Cell Line, H9", *AIDS*, 1992, 6, 533-539.

Cheng-Mayer et al., "Human Immunodeficiency Virus Can Productively Infect Cultured Human Glial Cells", *PNAS USA*, 1987, 84, 3526-3530.

Crowe et al., "Improved Cloning Efficiency of Polymerase Chain Reaction (PCR) Products after Proteinase K Digestion", *Nucleic Acids Res.*, 1991, 19, 184.

Desquenne-Clark et al., "T-Cell Receptor Peptide Immunization Leads to Enhanced and Chronic Experimental Allergic Encephalomyelitis", *PNAS USA*, 1991, 88, 7219-7223.

Desrosiers, R., "HIV with Multiple Gene Deletions as a Live Attenuated Vaccine for Aids", *AIDS Research and Human Retroviruses*, 1992, 8(3), 411-421.

Di Fiore et al., "erbB-2 is a Potent Oncogene When Overexpressed in NIH/3T3 Cells", *Science*, 1987, 237, 178-182.

Dubensky et al., "Direct Transfection of Viral and Plasmid DNA into the Liver or Spleen of Mice", *PNAS USA*, 1984, 81, 7529-7533.

Fisher et al., "HIV Infection is Blocked in vitro by Recombinant Soluble CD4", *Nature*, 1988, 331, 76-78.

Friedmann et al., "Progress Toward Human Gene Therapy", *Science*, 1989, 244, 1275-1281.

Goudsmit et al., "Human Antibody Response to a Strain-Specific HIV-1 gp120 Epitope Associated with Cell Fusion Inhibition", *AIDS*, 1988, 2, 157-164.

Hahn et al., "Suppression of Murine Lupus Nephritis by Administration of an Anti-Idiotypic Antibody to Anti-DNA", *J. Immunology*, 1984, 132, 187-190.

Hall-Craggs, E.C.B., "Rapid Degeneration and Regeneration of a Whole Skeletal Muscle Following Treatment with Bupivacain (Marcain)", *Experimental Neurology*, 1974, 43, 349-358.

Howley, P.M., "Papillomavirinae and Their Replication", *Virology*, 1990, 58, 1625-1650.

Israel et al., "Biological Activity of Polyoma Viral DNA in Mice and Hamsters", *J. Virology*, 1979, 29, 990-996.

Kaneda et al., "Increased Expression of DNA Cointroduced with Nuclear Protein in Adult Rat Liver", *Science*, 1989, 243, 357-378.

Klein et al., "Transformation of Microbes, Plants and Animals by Particle Bombardment", *Bio/Technology*, 1992, 10, 286-291.

Koenig et al., "Detection of AIDS Virus in Macrophages in Brian Tissue from AIDS Patients with Encephalopathy", *Science*, 1986, 233, 1089-1093.

Kowalski et al., "Functional Regions of the Envelope Glycoprotein of Human Immunodeficiency Virus Type 1", *Science*, 1987, 237, 1351-1355.

Langlois et al., "The Ability of Certain HIV Vaccines to Provoke Reactions Against Normal Cells", *Science*, 1992, 255, 292-293.

Lasky et al., "Neutralization of the AIDS Retrovirus by Antibodies to a Recombinant Envelope Glycoprotein", *Science*, 1986, 233, 209-212.

Lasky et al., "Delineation of a Region of the Human Immunodeficiency Virus Type 1 gp120 Glycoprotein Critical for Interaction with the CD4 Receptor", *Cell*, 1987, 50, 975-985.

Letvin et al., "Risks of Handling HIV", *Nature*, 1991, 349, 573.

Maddon et al., "The T4 Gene Encodes the AIDS Virus Receptor and is Expressed in the Immune System and the Brain", *Cell*, 1986, 47, 333-348.

Montefiori et al., "Evaluation of Antiviral Drugs and Neutralizing Antibodies to Human Immunodeficiency Virus by a Rapid and Sensitive Microtiter Infection Assay", *J. Clinical Microbiology*, 1988, 26, 231-235.

Morgenstern et al., "Advanced Mammalian Gene Transfer: High Titre Retroviralz Vectors with Multiple Drug Selection Markers and a Complementary Helper-Free Packaging Cell Line", *Nucleic Acids Res.*, 1990, 18, 3587-3596.

Nabel et al., "Site-Sepcific Gene Expression in Vivo by Direct Gene Transfer into the Arterial Wall", *Science*, 1990, 249, 1285-1288.

Nicolau et al., "In vivo Expression of Rat Insulin After Intravenous Administration of the Liposome-Entrapped Gene for Rat Insulin I", *PNAS USA*, 1983, 80, 1068-1072.

Osther et al., "Protective Humoral Immune Responses to the Human Immunodeficiency Virus Induced in Immunized Pigs: A Possible Source of Therapeutic Immunoglobulin Preparations", *Hybridoma*, 1991, 10, 673-683.

Osther et al., "The Quick Western Blot, A Novel Transportable 50-Minute HIV-1 Antibody Test", *Transplantation*, 1989, 47, 834-838.

Putney et al., "Development of an HIV Subunit Vaccine", *V International Conference on AIDS*, Quebec, Canada, Jun. 4-9, 1989.

Reiz, M. S., *AIDS Res. Human Retro.*, 1992, 8, 1549.

Ronen, D. et al., "Expression of wild-type and mutant p53 proteins by recombinant vaccinia viruses", *Nucleic Acids Research*, 1992, 20(13), 3435-3441.

Sambrook et al., "Molecular Cloning: A Laboratory Manual", Cold Spring Harbor Laboratory Press, 1989.

Schauer, M. and Billich, "The N-Terminal Region of HIV-1 Integrase is Required for Integration Activity, but not for DNA-Binding", *Biochem. Biophy. Res.Comm.*, 1992, 185(3), 874-880.

Schrier et al., "B- and T-Lymphocyte Responses to an Immunodominant Epitope of Human Immunodeficiency Virus", *J. Virology*, 1988, 62, 2531-2536.

Seed et al., "Molecular Cloning of the CD2 Antigen, the T-Cell Erythrocyte Receptor, by a Rapid Immunoselection Procedure", *PNAS USA*, 1987, 84, 3365-3369.

Seeger et al., "The Cloned Genome of Ground Squirrel Hepatitis Virus is Infectious in the Animal", *PNAS USA*, 1984, 81, 5849-5852.

Shah et al., "Papillomaviruses", *Virology*, 1990, 59, 1651-16761.

Sun et al., "Generation and CHaracterization of Monoclonal Antibodies to the Putative CD4-Binding Domain of Human immunodeficiency Virus Type 1 gp120", *J. Virology*, 1989, 63, 3579-3585.

Szala et al., "Molecular Cloning of cDNA for the Carcinoma-Associated Antigen GA733-2", *PNAS USA*, 1990, 87, 3542-3546.

Tang et al., "Genetic Immunization is a Simple Method for Eliciting an Immune Response", *Nature*, 1992, 356, 152-154.

Teitelbaum et al., "In Vivo Effects of Antibodies Against a High Frequency Idiotype of Anti-DNA Antibodies in MRL Mice", 1984, 132, 1282-1285.

Thomason et al., "Stable Incorporation of a Bacterial Gene into Adult Rat Skeletal Muscle in vivo", *Cell Physiol.*, 1990, 27, C578-581.

Ugen et al., "Generation of Monoclonal Antibodies Against the Amino Region of gp120 Which Elicits Antibody Dependent Cellular Cytotoxicity", Cold Spring Harbor Laboratory Press, 1992.

Vandenbark et al., "Immunization with a Synthetic T-Cell Receptor V-Region Peptide Protects Against Experimental Autoimmune Encephalomyelitis", *Nature*, 1989, 341, 541-544.

Weiner et al., "Non-CD4 Molecules on Human Cells Improtant in HIV-1 Cell Entry", *Vaccines*, 1989, 115-120.

Wells, D., "Improved Gene Transfer by Direct Plasmid Injection Associated with Regeneration in Mouse Skeletal Muscle", *FEBS Letters*, 1993, 332, 179-182.

Will et al., "Cloned HBV DNA causes Hepatitis in Chimpanzees", *Nature*, 1982, 299, 740-742.

Williams et al., "Molecular Diagnosis of *Borrelia burgdorferi* Infection (Lyme Disease)", *DNA and Cell Biology*, 1992, 11, 207-213.

Wolff, J.A. et al., "Direct gene transfer into mouse muscle in vivo", *Science*, 1990, 247, 1465-1468.

Wolff et al., "Conditions Affecting Direct Gene Transfer into Rodent Muscle In Vivo", *BioTechniques*, 1991, 11, 474-485.

Wu et al., "Receptor-Mediated Gene Delivery and Expression in Vivo", *J. Biological Chemistry*, 1988, 263, 14621-14624.

Yang et al., "In vivo and in vitro Gene Transfer to Mammalian Somatic Cells by Particle Bombardment", *PNAS USA*, 1990, 87, 9568-9572.

Zelenin et al., "High-Velocity Mechanical DNA Transfer ofl the Chloramphenicolacetyl Transferase Gene into Rodent Liver, Kidney and Mammary Gland Cells in Organ Explants and in vivo", *FEBS Letters*, 1991, 280, 94-96.

Boiron et al., "A Biological Property of Deoxyribonucleic Acid", *Discussion and Preliminary Reports*, 1965, 150-153.

Fleckenstein et al., "Tumour Induction with DNA of Oncogenic Priamte Herpesviruses", *Nature*, 1978, 274, 57-59.

Glaser, V., *Genetic Engin. News*, 1996, 16(1), 6.

Mayne et al., "Tumour Induction by Simian Adenovirus SA7 DNA Fragments", *Nature New Biology*, 1971, 232, 182-183.

McCutchan et al., "Enhancement of the Infectivity of Simian Virus 40 Deoxyribonucleic Acid with Diethylaminoethyl-Dextran", *J. Nat. Cancer Institute*, 1968, 41, 351-356.

Orth et al., "Infectious and Oncogenic Effect of DNA Extracted from Cells Infected with Polyoma Virus", *P.S.E.B.M.*, 1964, 115, 1090-1095.

Rowe et al., "Studies of Mouse Polyoma Virus Infection", U.S. Dept. of Health, Education and Welfare, 1958, pp. 379-391.

Schultz, A.M. et al., *AIDS*, 1993, 7(Supp. 1), S161-S170.

Sol et al., "Oncogenicity of SV40 DNA int eh Syrian Hamster", *J. Gen. Vir.*, 1977, 37, 635-638.

Ulmer et al., "Heterologous Protection Against Influenza by Injection of DNA Encoding a Viral Protein", *Science*, 1993, 259, 1745-1749.

Vitadello et al., "Gene Transfer in Regenerating Muscle", *J. Cellular Biochem.*, 1993, Suppl. 17E:252, Mar. 29-Apr. 25, 1993.

Jenkins et al., "Formation of lentivirus particles by mammalian cells infected with recombinant fowlpox virus," *Aids Research and Human Retroviruses* (1991) 7(12):991-998.

Thomason et al., "Stable Incorporation of a Bacterial Gene Into Adult Rat Skeletal Muscle In-Vivo," *American Journal of Physiology*, 1990, vol. 258, No. 3, pp. C578-C582.

De-Chu et al., "Genetic Immunization in a Simple Method for Eliciting an Immune Response," *Nature*, 1992, vol. 356, No. 6365, pp. 152-154.

Kaneda et al., "Increased Expression of DNA Cointroduced With Nuclear Protein in Adult Rat Liver," *Science*, 1989, vol. 243, pp. 375-378.

Wang et al., "Gene Inoculation Generates Immune Responses Against Human Immunodeficiency Virus Type 1," *Proceedings of the National Academy of Sciences*, 1993, vol. 90, No. 9, pp. 4156-4160.

Wells et al., "Improved Gene Transfer by Direct Plasmid Injection Associated With Regeneration in Mouse Skeletal Muscle," *FEBS Letters*, 1993, vol. 332, No. ½, pp. 179-182.

E. T. Juengst, BMJ, 2003, vol. 326, pp. 1410-1411.*

A. Mountain, TIBTECH, 2000, vol. 18, pp. 119-128.*

E. B. Kmiec, American Scientist, 1999, vol. 87, pp. 240-247.*

Verma et al., Nature, 1997, vol. 329, pp. 239-242.*

W. French Anderson, Nature, 1998, vol. 392, pp. 25-30.*

Webster et al. DNA vaccines A review of developments. Biodrugs vol. 8(4):273-292, Oct. 1997.*

Rabinovich et al. Vaccine technologies: View to the future. Science vol. 265:1401-1404, Sep. 1994.*

Cho et al. Macromolecular versus small-molecule therapeutics: Drug discovery, development and clinical considerations. TIBTECH vol. 14:153-158, May 1996.*

Piscitelli et al. Immune-based therapies for treatmetn of HIV infection. Ann. Pharmacol. vol. 30:62-76, Feb. 1996.*

Danko et al. Pharmacological enhancement of in vivo foreign gene expression in muscle. Gene Therapy, vol. 1(2):114-121, Feb. 1994.*

Chattergoon et al. Genetic immunization: a new era in vaccines and immune therapeutics. FASEB J. vol. 11:753-563, Jun. 1997.*

Weiner et al. Genetic vaccines. Scientific American. vol. 281(1):34-42, Jul. 1999.*

Yasutomi et al. A vaccine-elicited, single viral epitope-specific cytotoxic T lymphocyte response does not pretect against intravenous, cell-free simian immunodeficiency virus challenge. J. Virol. vol. 69(4):2279-2284, 1995.*

Price et al. Lineage analysis in teh vertebrate nervous system by retrovirus-mediated gene transfer. PNAS vol. 84:156-16, 1987.*

* cited by examiner

COMPOSITIONS AND METHODS FOR DELIVERY OF GENETIC MATERIAL

CROSS REFERENCE TO RELATED APPLICATIONS

This Application is a continuation of U.S. patent application Ser. No. 09/359,975, filed Jul. 23, 1999, issued on Feb. 21, 2006, as U.S. Pat. No. 7,001,759, which is a continuation of U.S. patent application Ser. No. 08/979,385, filed on Nov. 26, 1997, issued on Nov. 9, 1999, as U.S. Pat. No. 5,981,505, which is a file wrapper continuation of U.S. patent application Ser. No. 08/495,684, which is a national stage entry of PCT Application No. PCT/US94/00899 filed on Jan. 26, 1994, now abandoned, which is a continuation-in-part application of and claiming priority to the following five non-provisional applications: U.S. patent application Ser. No. 08/125,012, filed Sep. 21, 1993, which issued as U.S. Pat. No. 5,593,972 on Jan. 14, 1997; U.S. patent application Ser. No. 08/124,962, filed on Sep. 21, 1993, now abandoned; U.S. patent application Ser. No. 08/093,235, filed on Jul. 15, 1993, now abandoned; U.S. patent application Ser. No. 08/029,336, filed on Mar. 11, 1993, now abandoned; and U.S. patent application Ser. No. 08/008,342, filed on Jan. 26, 1993, now abandoned.

FIELD OF THE INVENTION

The present invention relates to compositions and methods for introducing genetic material into the cells of an individual. The compositions and methods of the invention can be used to deliver protective and/or therapeutic agents including genetic material that encodes protein targets for immunization and therapeutic proteins.

IN THE SEQUENCE LISTING

Please add new pages 1-12 containing the Sequence Listing submitted under 37 C.F.R. §§1.821-1.825.

BACKGROUND OF THE INVENTION

The direct introduction of a normal, functional gene into a living animal has been studied as a means for replacing defective genetic information. In some studies, DNA is introduced directly into cells of a living animal without the use of a viral particle or other infectious vector. Nabel, E. G., et al., (1990) *Science* 249:1285-1288, disclose site-specific gene expression in vivo of a beta-galactosidase gene that was transferred directly into the arterial wall in mice. Wolfe, J. A. et al., (1990) *Science* 247:1465-1468, disclose expression of various reporter genes that were directly transferred into mouse muscle in vivo. Acsadi G., et al., (1991) *Nature* 352:815-818, disclose expression of human dystrophin gene in mice after intramuscular injection of DNA constructs. Wolfe, J. A., et al., 1991 *BioTechniques* 11(4):474-485, which is incorporated herein by reference, refers to conditions affecting direct gene transfer into rodent muscle in vivo. Felgner, P. L. and G. Rhodes, (1991) *Nature* 349:351-352, disclose direct delivery of purified genes in vivo as drugs without the use of retroviruses.

The use of direct gene transfer as an alternative anti-pathogen vaccination method has been suggested. Use of direct gene transfer by single injection is suggested as a possible vaccination strategy against HIV. A cellular immune response to HIV gp120 resulting from introduction of plasmid DNA encoding the same into cells is reported to have been observed. PCT International Application Number PCT/US90/01515 published Oct. 4, 1990 discloses methods of immunizing an individual against pathogen infection by directly injecting naked polynucleotides into the individual's cells in a single step procedure. The use of transfecting agents other than lipofectins is specifically excluded from the disclosed methods. The stimulation of inoculated cells is neither disclosed nor suggested. An HIV vaccine is disclosed which consists of the introduction of polynucleotides that encode the viral protein gp120. The operability of this vaccine is not evidenced.

Thomason, D. B. et al., (1990) *Cell Physiol.* 27:C578-581 and PCT Patent Application Serial No. WO 91/12329 disclose administering bupivacaine to muscle cells in order to induce satellite cell proliferation as part of a retroviral-mediated gene delivery protocol.

SUMMARY OF THE INVENTION

The present invention relates to methods of introducing genetic material into the cells of an individual. The methods comprises the steps of contacting cells of said individual with a polynucleotide function enhancer agent, which is preferably an agent that facilitates the uptake of DNA by the cells or enhances an inflammatory response, and administering to the cells, a nucleic acid molecule that comprises a nucleotide sequence that either encodes a desired peptide or protein, or serves as a template for functional nucleic acid molecules. The nucleic acid molecule is administered free from retroviral particles. The desired protein may either be a protein which functions within the individual or it serves as a target for an immune response.

The present invention relates to a method of immunizing an individual against a pathogen. The method comprises the steps of contacting cells of said individual with a polynucleotide function enhancer agent, which is preferably an agent that facilitates the uptake of DNA by the cells or enhances the immune response, and administering to the cells, a nucleic acid molecule that comprises a nucleotide sequence that encodes a peptide which comprises at least an epitope identical or substantially similar to an epitope displayed on a pathogen antigen and is operatively linked to regulatory sequences. The nucleic acid molecule is capable of being expressed in the cells of the individual.

The present invention relates to a method of immunizing a human against HIV. The method comprises the steps of administering to a human a nucleic acid molecule that comprises a nucleotide sequence that encodes at least one peptide that comprises at least one epitope identical or substantially similar to an epitope displayed on an HIV protein operatively linked to regulatory sequences.

The present invention relates to a method of immunizing a human against HIV. The method comprises the steps of administering two different nucleic acid molecules to different cells of the human. Each nucleic acid molecule comprises a nucleotide sequence that encodes at least one peptide which comprises at least one epitope identical or substantially similar to an epitope displayed on an HIV protein operatively linked to regulatory sequences. The different nucleic acid molecules each comprise different nucleotide sequences that encode at least one different peptide from the other and are each capable of being expressed in human cells.

The present invention relates to methods of immunizing an individual against a hyperproliferative disease or an autoimmune disease. The methods comprise the steps of administering to cells of an individual, a nucleic acid molecule that comprises a nucleotide sequence that encodes a peptide that comprises at least an epitope identical or substantially similar to an epitope displayed on a hyperproliferative disease-associated protein or an autoimmune disease-associated protein, respectively, and is operatively linked to regulatory sequences; the nucleic acid molecule being capable of being expressed in the cells.

The present invention relates to methods of treating an individual suffering from a disease comprising the steps of contacting cells of said individual with a polynucleotide function enhancer agent, which is preferably an agent that facilitates the uptake of DNA by the cells or enhances an inflammatory response, and administering to cells of an individual, a nucleic acid molecule that comprises a nucleotide sequence which functions in place of a defective gene or which encodes a molecule that produces a therapeutic effect in the individual and is operatively linked to regulatory sequences; the nucleic acid molecule being capable of being expressed in the cells.

The present invention relates to pharmaceutical compositions which comprise a nucleic acid molecule and a polynucleotide function enhancer. The present invention relates to pharmaceutical kits which comprise a container comprising a nucleic acid molecule and a container comprising a polynucleotide function enhancer.

The present invention relates to prophylactic and therapeutic HIV vaccines comprising a pharmaceutically acceptable carrier or diluent and a nucleic acid molecule that encodes one or more peptides that each comprises at least an epitope identical or substantially similar to an epitope displayed on at least one HIV protein operatively linked to regulatory sequences; the nucleic acid molecule being capable of being expressed in human cells.

The present invention relates to prophylactic and therapeutic HIV vaccines comprising two inoculants. The first inoculant comprises a pharmaceutically acceptable carrier or diluent and a first nucleic acid molecule. The first nucleic acid molecule comprises a nucleotide sequence that encodes one or more peptides that each comprises at least an epitope identical or substantially similar to an epitope displayed on at least one HIV protein operatively linked to regulatory sequences; the nucleic acid molecule being capable of being expressed in human cells. The second inoculant comprises a pharmaceutically acceptable carrier or diluent and a second nucleic acid molecule. The second nucleic acid molecule comprises a nucleotide sequence that encodes one or more peptides that each comprises at least an epitope identical or substantially similar to an epitope displayed on at least one HIV protein operatively linked to regulatory sequences; the nucleic acid molecule being capable of being expressed in human cells. The first and second nucleic acid molecules are different and encode different peptides.

DETAILED DESCRIPTION OF THE INVENTION

Figure 1A:
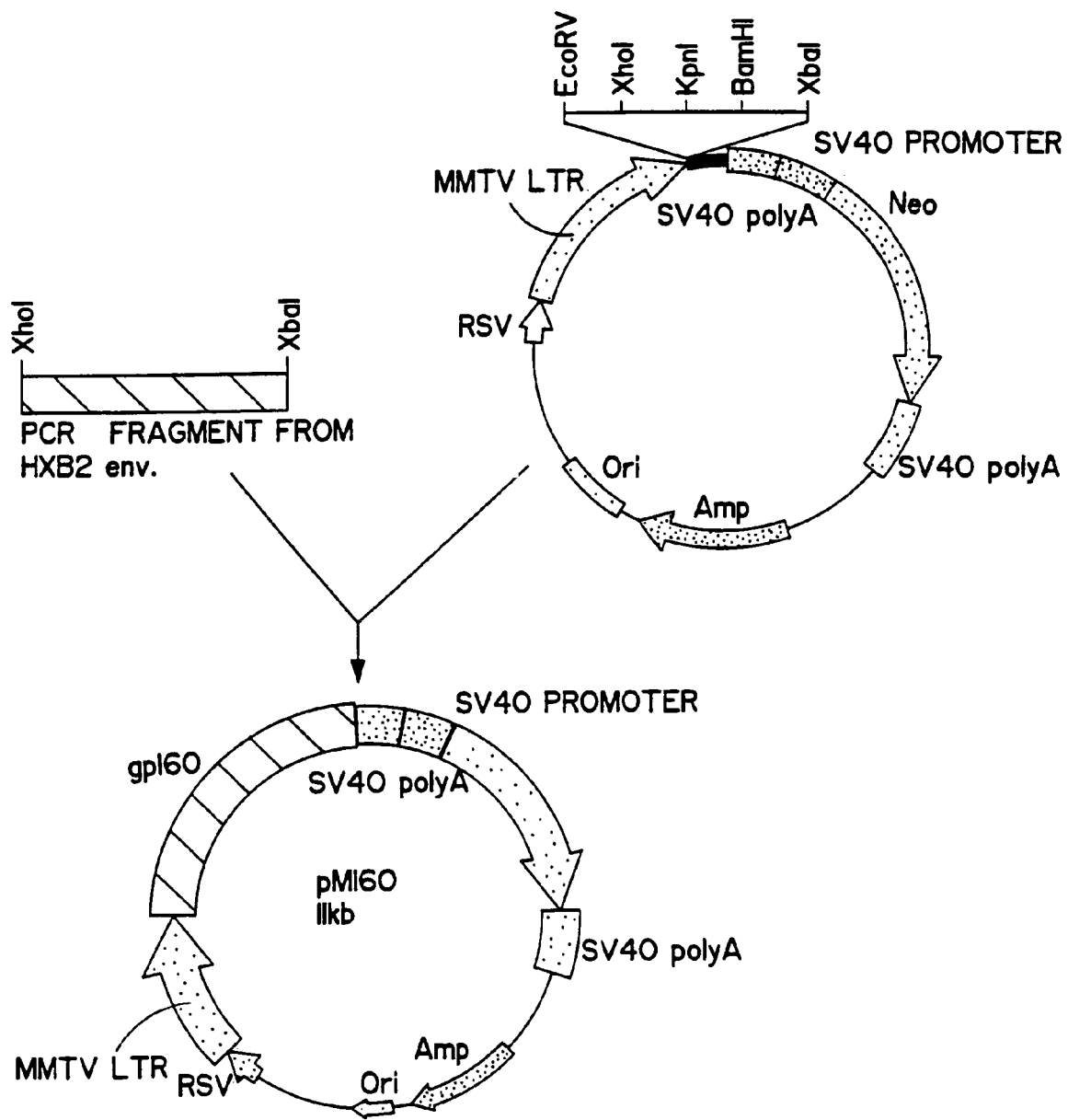
FIG. 1A is a diagram depicting the construction of plasmid pM160 which was produced by inserting a PCR-generated fragment that encodes the HIV-HXB2 glycoprotein gp160 into plasmid pMAMneoBlue (Clonetech).
Figure 1B:
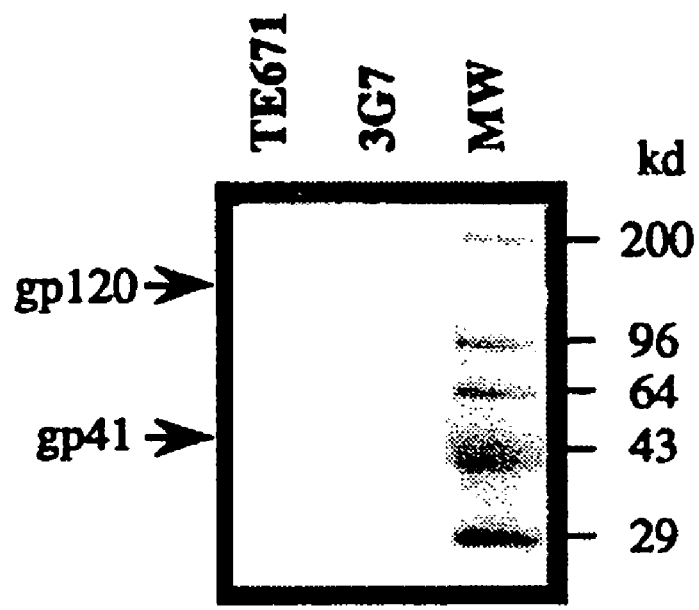
FIG. 1B is a photograph of an autoradiogram of a Western blot of whole cell lysates of cells transfected with the pM160 plasmid (3G7 cells) versus vector-alone transfected cells (TE671 cells) showing production of gp120 and gp41 in 3G7 cells and not in TE671 cells.

The present invention relates to a method of introducing nucleic acid molecules into the cells of an animal which provides for the high level of uptake and function of the nucleic acid molecules. The method of the present invention comprises the steps of administering nucleic acid molecules that are free from viral particles, particularly retroviral particles, to the cell of an individual in conjunction with administration of a co-agent which enhances the inflammatory response and/or enhances expression of the nucleic acid molecule in the tissue and/or facilitates the uptake of the nucleic acid molecule by the cell. Preferred embodiments of the present invention provide methods of delivering nucleic acid molecules to cells of an individual without the use of infectious agents.

Nucleic acid molecules which are delivered to cells according to the invention may serve as: 1) genetic templates for proteins that function as prophylactic and/or therapeutic immunizing agents; 2) replacement copies of defective, missing or non-functioning genes; 3) genetic templates for therapeutic proteins; 4) genetic templates for antisense molecules; or 5) genetic templates for ribozymes. In the case of nucleic acid molecules which encode proteins, the nucleic acid molecules preferably comprise the necessary regulatory sequences for transcription and translation in the cells of the animal. In the case of nucleic acid molecules which serve as templates for antisense molecules and ribozymes, such nucleic acid molecules are preferably linked to regulatory elements necessary for production of sufficient copies of the antisense and ribozyme molecules encoded thereby respectively. The nucleic acid molecules are free from retroviral particles and preferably provided as DNA in the form of plasmids.

The co-agent is also referred to herein as a "polynucleotide function enhancer" or "PFE". A PFE is a compound or composition which enhances the inflammatory response and/or enhances expression of the nucleic acid molecule in the tissue and/or facilitates the uptake of the nucleic acid molecule by the cell and preferably has more than one of these properties. Polynucleotide function enhancers that facilitate DNA and RNA uptake by cells and stimulate cell division and replication are also referred to as cell stimulating agents. Preferred co-agents according to the present invention are selected from the group consisting of benzoic acid esters and anilides. In preferred embodiments, the PFE is bupivacaine.

According to some aspects of the present invention, compositions and methods are provided which prophylactically and/or therapeutically immunize an individual against a pathogen or abnormal, disease-related cell. The genetic material encodes a peptide or protein that shares at least an epitope with an immunogenic protein found on the pathogen or cells to be targeted. The genetic material is expressed by the individual's cells and serves as an immunogenic target against which an immune response is elicited. The resulting immune response is broad based: in addition to a humoral immune response, both arms of the cellular immune response are elicited. The methods of the present invention are useful for conferring prophylactic and therapeutic immunity. Thus, a method of immunizing includes both methods of protecting an individual from pathogen challenge, or occurrence or proliferation of specific cells as well as methods of treating an individual suffering from pathogen infection, hyperproliferative disease or autoimmune disease.

The present invention is useful to elicit broad immune responses against a target protein, i.e. proteins specifically associated with pathogens or the individual's own "abnormal" cells. The present invention is useful to immunize individuals against pathogenic agents and organisms such that an immune response against a pathogen protein provides protective immunity against the pathogen. The present invention is useful to combat hyperproliferative diseases and disorders such as cancer by eliciting an immune response against a target protein that is specifically associated with the hyperproliferative cells. The present invention is useful to combat autoimmune diseases and disorders by eliciting an immune response against a target protein that is specifically associated with cells involved in the autoimmune condition.

Some aspects of the present invention relate to gene therapy; that is, to compositions for and methods of introducing nucleic acid molecules into the cells of an individual exogenous copies of genes which either correspond to defective, missing, non-functioning or partially functioning genes in the individual or which encode therapeutic proteins, i.e. proteins whose presence in the individual will eliminate a deficiency in the individual and/or whose presence will provide a therapeutic effect on the individual thereby providing a means of delivering the protein by an alternative means from protein administration.

As used herein the term "desired protein" is meant to refer to peptides and protein encoded by gene constructs of the present invention which either act as target proteins for an immune response or as a therapeutic or compensating protein in gene therapy regimens.

According to the present invention, DNA or RNA that encodes a desired protein is introduced into the cells of an individual where it is expressed, thus producing the desired protein. The DNA or RNA encoding the desired protein is linked to regulatory elements necessary for expression in the cells of the individual. Regulatory elements for DNA expression include a promoter and a polyadenylation signal. In addition, other elements, such as a Kozak region, may also be included in the genetic construct.

As used herein, the term "genetic construct" refers to the DNA or RNA molecule that comprises a nucleotide sequence which encodes the desired protein and which includes initiation and termination signals operably linked to regulatory elements including a promoter and polyadenylation signal capable of directing expression in the cells of the vaccinated individual.

As used herein, the term "expressible form" refers to gene constructs which contain the necessary regulatory elements operable linked to a coding sequence that encodes a target protein, such that when present in the cell of the individual, the coding sequence will be expressed.

As used herein, the term "genetic vaccine" refers to a pharmaceutical preparation that comprises a genetic construct that comprises a nucleotide sequence that encodes a target protein including pharmaceutical preparations useful to invoke a therapeutic immune response.

As used herein, the term "genetic therapeutic" refers to a pharmaceutical preparation that comprises a genetic construct that comprises a nucleotide sequence that encodes a therapeutic or compensating protein.

As used herein, the term "target protein" refers to a protein against which an immune response can be elicited. The target protein is an immunogenic protein which shares at least an epitope with a protein from the pathogen or undesirable cell-type such as a cancer cell or a cell involved in autoimmune disease against which immunization is required. The immune response directed against the target protein will protect the individual against and treat the individual for the specific infection or disease with which the target protein is associated.

As used herein, the term "sharing an epitope" refers to proteins which comprise at least one epitope that is identical to or substantially similar to an epitope of another protein.

As used herein, the term "substantially similar epitope" is meant to refer to an epitope that has a structure which is not identical to an epitope of a protein but nonetheless invokes an cellular or humoral immune response which cross reacts to that protein.

As used herein, the term "therapeutic protein" is meant to refer to proteins whose presence confers a therapeutic benefit to the individual.

As used herein, the term "compensating protein" is meant to refer to proteins whose presence compensates for the absence of a fully functioning endogenously produced protein due to an absent, defective, non-functioning or partially functioning endogenous gene.

Genetic constructs comprise a nucleotide sequence that encodes a desired protein operably linked to regulatory elements needed for gene expression. Accordingly, incorporation of the DNA or RNA molecule into a living cell results in the expression of the DNA or RNA encoding the desired protein and thus, production of the desired protein.

When taken up by a cell, the genetic construct which includes the nucleotide sequence encoding the desired protein operably linked to the regulatory elements may remain present in the cell as a functioning extrachromosomal molecule or it may integrate into the cell's chromosomal DNA. DNA may be introduced into cells where it remains as separate genetic material in the form of a plasmid. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be administered to the cell. It is also contemplated to provide the genetic construct as a linear minichromosome including a centromere, telomeres and an origin of replication.

The molecule that encodes a desired protein may be DNA or RNA which comprise a nucleotide sequence that encodes the desired protein. These molecules may be cDNA, genomic DNA, synthesized DNA or a hybrid thereof or an RNA molecule such as mRNA. Accordingly, as used herein, the terms "DNA construct", "genetic construct" and "nucleotide sequence" are meant to refer to both DNA and RNA molecules.

The regulatory elements necessary for gene expression of a DNA molecule include: a promoter, an initiation codon, a stop codon, and a polyadenylation signal. In addition, enhancers are often required for gene expression. It is necessary that these elements be operable linked to the sequence that encodes the desired proteins and that the regulatory elements are operably in the individual to whom they are administered.

Initiation codons and stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV40 polyadenylation signals and LTR polyadenylation signals. In particular, the SV40 polyadenylation signal which is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pCEP4 and pREP4 from Invitrogen (San Diego, Calif.) contain the Epstein Barr virus origin of replication and nuclear antigen EBNA-1 coding region which produces high copy episomal replication without integration.

In some preferred embodiments, the vector used is selected form those described in Example 46. In aspects of the invention relating to gene therapy, constructs with origins of replication including the necessary antigen for activation are preferred.

In some preferred embodiments related to immunization applications, the genetic construct contains nucleotide sequences that encode a target protein and further include genes for proteins which enhance the immune response against such target proteins. Examples of such genes are those which encode cytokines and lymphokines such as α-interferon, gamma-interferon, platelet derived growth factor (PDGF), GC-SF, GM-CSF, TNF, epidermal growth factor (EGF), IL-1, IL-2, IL-4, IL-6, IL-8, IL-10 and IL-12. In some embodiments, it is preferred that the gene for GM-CSF is included in genetic constructs used in immunizing compositions.

An additional element may be added which serves as a target for cell destruction if it is desirable to eliminate cells receiving the genetic construct for any reason. A herpes thymidine kinase (tk) gene in an expressible form can be included in the genetic construct. The drug gangcyclovir can be administered to the individual and that drug will cause the selective killing of any cell producing tk, thus, providing the means for the selective destruction of cells with the genetic construct.

In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs which are functional in the cells.

In order to test expression, genetic constructs can be tested for expression levels in vitro using tissue culture of cells of the same type as those to be administered. For example, if the genetic vaccine is to be administered into human muscle cells, muscle cells grown in culture such as solid muscle tumors cells of rhabdomyosarcoma may be used as an in vitro model to measure expression level.

The genetic constructs used in the present invention are not incorporated within retroviral particles. The genetic constructs are taken up by the cell without retroviral particle-mediated insertion such as that which occurs when retrovirus particles with retroviral RNA that is incorporated in retroviral particles infects a cell. As used herein, the term "free from retroviral particles" is meant to refer to genetic constructs that are not incorporated within retroviral particles. As used herein, "dissociated from an infectious agent" is meant to refer to genetic material which is not part of a viral, bacterial or eukaryotic vector, either active, inactivated, living or dead, that is capable of infecting a cell.

In some embodiments, the genetic constructs constitute less than a complete, replicatable viral genome such that upon introduction into the cell, the genetic construct possesses insufficient genetic information to direct production of infectious viral particles. As used herein, the term "incomplete viral genome" is meant to refer to a genetic construct which contains less than a complete genome such that incorporation of such a genetic construct into a cell does not constitute introduction of sufficient genetic information for the production of infectious virus.

In some embodiments, an attenuated viral vaccine may be delivered as a genetic construct which contains enough genetic material to allow for production of viral particles. Delivery of the attenuated vaccine as a genetic construct allows for an easier way to produce large quantities of safe, pure active immunizing product.

The genetic construct may be administered with or without the use microprojectiles. It is preferred that the genetic constructs of the present invention may be delivered to the cells of an individual free of solid particles. As used herein, the phrase "free of solid particles" is meant to refer to a liquid that does not contain any solid microprojectile used as a means to perforate, puncture or otherwise pierce the cell membrane of a cell in order to create a port of entry for genetic material into the cell.

The present invention may be used to immunize an individual against all pathogens such as viruses, prokaryote and pathogenic eukaryotic organisms such as unicellular pathogenic organisms and multicellular parasites. The present invention is particularly useful to immunize an individual against those pathogens which infect cells and which are not encapsulated such as viruses, and prokaryote such as gonorrhoea, listeria and shigella. In addition, the present invention is also useful to immunize an individual against protozoan pathogens which include a stage in the life cycle where they are intracellular pathogens. As used herein, the term "intracellular pathogen" is meant to refer to a virus or pathogenic organism that, at least part of its reproductive or life cycle, exists within a host cell and therein produces or causes to be produced, pathogen proteins. Table 1 provides a listing of some of the viral families and genera for which vaccines according to the present invention can be made. DNA constructs that comprise DNA sequences which encode the peptides that comprise at least an epitope identical or substantially similar to an epitope displayed on a pathogen antigen such as those antigens listed on the tables are useful in vaccines. Moreover, the present invention is also useful to immunize an individual against other pathogens including prokaryotic and eukaryotic protozoan pathogens as well as multicellular parasites such as those listed on Table 2.

In order to produce a genetic vaccine to protect against pathogen infection, genetic material which encodes immunogenic proteins against which a protective immune response can be mounted must be included in the genetic construct. Whether the pathogen infects intracellularly, for which the present invention is particularly useful, or extracellularly, it is unlikely that all pathogen antigens will elicit a protective response. Because DNA and RNA are both relatively small and can be produced relatively easily, the present invention provides the additional advantage of allowing for vaccination with multiple pathogen antigens. The genetic construct used in the genetic vaccine can include genetic material which encodes many pathogen antigens. For example, several viral genes may be included in a single construct thereby providing multiple targets. In addition, multiple inoculants which can be delivered to different cells in an individual can be prepared to collectively include, in some cases, a complete or, more preferably, an incomplete such as a near complete set of genes in the vaccine. For example, a complete set of viral genes may be administered using two constructs which each contain a different half of the genome which are administered at different sites. Thus, an immune response may be invoked against each antigen without the risk of an infectious virus being assembled. This allows for the introduction of more than a single antigen target and can eliminate the requirement that protective antigens be identified.

The ease of handling and inexpensive nature of DNA and RNA further allow for more efficient means of screening for protective antigens. Genes can be sorted and systematically tested much more easily than proteins. The pathogenic agents and organism for which the vaccine is being produced to protect against is selected and an immunogenic protein is identified. Tables 1 and 2 include lists of some of the pathogenic agents and organisms for which genetic vaccines can be prepared to protect an individual from infection by them. In some preferred embodiments, the methods of immunizing an individual against a pathogen are directed against HIV, HTLV or HBV.

Another aspect of the present invention provides a method of conferring a broad based protective immune response against hyperproliferating cells that are characteristic in hyperproliferative diseases and to a method of treating individuals suffering from hyperproliferative diseases. As used herein, the term "hyperproliferative diseases" is meant to refer to those diseases and disorders characterized by hyperproliferation of cells. Examples of hyperproliferative diseases include all forms of cancer and psoriasis.

It has been discovered that introduction of a genetic construct that includes a nucleotide sequence which encodes an immunogenic "hyperproliferating cell"-associated protein into the cells of an individual results in the production of those proteins in the vaccinated cells of an individual. As used herein, the term "hyperproliferative-associated protein" is meant to refer to proteins that are associated with a hyperproliferative disease. To immunize against hyperproliferative diseases, a genetic construct that includes a nucleotide sequence which encodes a protein that is associated with a hyperproliferative disease is administered to an individual.

In order for the hyperproliferative-associated protein to be an effective immunogenic target, it must be a protein that is produced exclusively or at higher levels in hyperproliferative cells as compared to normal cells. Target antigens include such proteins, fragments thereof and peptides which comprise at least an epitope found on such proteins. In some cases, a hyperproliferative-associated protein is the product of a mutation of a gene that encodes a protein. The mutated gene encodes a protein which is nearly identical to the normal protein except it has a slightly different amino acid sequence which results in a different epitope not found on the normal protein. Such target proteins include those which are proteins encoded by oncogenes such as myb, myc, fyn, and the translocation gene bcr/abl, ras, src, P53, neu, trk and EGRF. In addition to oncogene products as target antigens, target proteins for anti-cancer treatments and protective regimens include variable regions of antibodies made by B cell lymphomas and variable regions of T cell receptors of T cell lymphomas which, in some embodiments, are also used target antigens for autoimmune disease. Other tumor-associated proteins can be used as target proteins such as proteins which are found at higher levels in tumor cells including the protein recognized by monoclonal antibody 17-1A and folate binding proteins.

While the present invention may be used to immunize an individual against one or more of several forms of cancer, the present invention is particularly useful to prophylactically immunize an individual who is predisposed to develop a particular cancer or who has had cancer and is therefore susceptible to a relapse. Developments in genetics and technology as well as epidemiology allow for the determination of probability and risk assessment for the development of cancer in individual. Using genetic screening and/or family health histories, it is possible to predict the probability a particular individual has for developing any one of several types of cancer.

Similarly, those individuals who have already developed cancer and who have been treated to remove the cancer or are otherwise in remission are particularly susceptible to relapse and reoccurrence. As part of a treatment regimen, such individuals can be immunized against the cancer that they have been diagnosed as having had in order to combat a recurrence. Thus, once it is known that an individual has had a type of cancer and is at risk of a relapse, they can be immunized in order to prepare their immune system to combat any future appearance of the cancer.

The present invention provides a method of treating individuals suffering from hyperproliferative diseases. In such methods, the introduction of genetic constructs serves as an immunotherapeutic, directing and promoting the immune system of the individual to combat hyperproliferative cells that produce the target protein.

The present invention provides a method of treating individuals suffering from autoimmune diseases and disorders by conferring a broad based protective immune response against targets that are associated with autoimmunity including cell receptors and cells which produce "self"-directed antibodies.

T cell mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Vaccination against the variable region of the T cells would elicit an immune response including CTLs to eliminate those T cells.

In RA, several specific variable regions of T cell receptors (TCRs) which are involved in the disease have been characterized. These TCRs include Vβ-3, Vβ-14, Vβ-17 and Vα-17. Thus, vaccination with a DNA construct that encodes at least one of these proteins will elicit an immune response that will target T cells involved in RA. See: Howell, M. D., et al., 1991 *Proc. Natl. Acad. Sci. USA* 88:10921-10925; Paliard, X., et al., 1991 *Science* 253:325-329; Williams, W. V., et al., 1992 *J. Clin. Invest.* 90:326-333; each of which is incorporated herein by reference.

In MS, several specific variable regions of TCRs which are involved in the disease have been characterized. These TCRs include Vβ-7 and Vα-10. Thus, vaccination with a DNA construct that encodes at least one of these proteins will elicit an immune response that will target T cells involved in MS. See: Wucherpfennig, K. W., et al., 1990 *Science* 248:1016-1019; Oksenberg, J. R., et al., 1990 *Nature* 345:344-346; each of which is incorporated herein by reference.

In scleroderma, several specific variable regions of TCRs which are involved in the disease have been characterized. These TCRs include Vβ-6, Vβ-8, Vβ-14 and Vα-16, Vα-3C, Vα-7, Vα-14, Vα-15, Vα-16, Vα-28 and Vα-12. Thus, vaccination with a DNA construct that encodes at least one of these proteins will elicit an immune response that will target T cells involved in scleroderma.

In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Genetic vaccines can be prepared using this information.

B cell mediated autoimmune diseases include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies which bind to endogenous antigens and initiate the inflammatory cascade associated with autoimmune diseases. Vaccination against the variable region of antibodies would elicit an immune response including CTLs to eliminate those B cells that produce the antibody.

In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Genetic vaccines can be prepared using this information.

In the case of SLE, one antigen is believed to be DNA. Thus, in patients to be immunized against SLE, their sera can be screened for anti-DNA antibodies and a vaccine can be prepared which includes DNA constructs that encode the variable region of such anti-DNA antibodies found in the sera.

Common structural features among the variable regions of both TCRs and antibodies are well known. The DNA sequence encoding a particular TCR or antibody can generally be found following well known methods such as those described in Kabat, et al. 1987 *Sequence of Proteins of Immunological Interest* U.S. Department of Health and Human Services, Bethesda Md., which is incorporated herein by reference. In addition, a general method for cloning functional variable regions from antibodies can be found in Chaudhary, V. K., et al., 1990 *Proc. Natl. Acad. Sci. USA* 87:1066, which is incorporated herein by reference.

In some of the embodiments of the invention that relate to gene therapy, the gene constructs contain either compensating genes or genes that encode therapeutic proteins. Examples of compensating genes include a gene which encodes dystrophin or a functional fragment, a gene to compensate for the defective gene in patients suffering from cystic fibrosis, an insulin, a gene to compensate for the defective gene in patients suffering from ADA, and a gene encoding Factor VIII. Examples of genes encoding therapeutic proteins include genes which encodes erythropoietin, interferon, LDL receptor, GM-CSF, IL-2, IL-4 and TNF. Additionally, genetic constructs which encode single chain antibody components which specifically bind to toxic substances can be administered.

In some preferred embodiments, the dystrophin gene is provided as part of a mini-gene and used to treat individuals suffering from muscular dystrophy. In some preferred embodiments, a mini-gene which contains coding sequence for a partial dystrophin protein is provided. Dystrophin abnormalities are responsible for both the milder Becker's Muscular Dystrophy (BMD) and the severe Duchenne's Muscular Dystrophy (DMD). In BMD dystrophin is made, but it is abnormal in either size and/or amount. The patient is mild to moderately weak. In DMD no protein is made and the patient is chair-bound by age 13 and usually dies by age 20. In some patients, particularly those suffering from BMD, partial dystrophin protein produced by expression of a mini-gene delivered according to the present invention can provide improved muscle function.

In some preferred embodiments, genes encoding IL-2, IL-4, interferon or TNF are delivered to tumor cells which are either present or removed and then reintroduced into an individual. In some embodiments, a gene encoding gamma interferon is administered to an individual suffering from multiple sclerosis.

Antisense molecules and ribozymes may also be delivered to the cells of an individual by introducing genetic material which acts as a template for copies of such active agents. These agents inactivate or otherwise interfere with the expression of genes that encode proteins whose presence is undesirable. Constructs which contain sequences that encode antisense molecules can be used to inhibit or prevent production of proteins within cells. Thus, production proteins such as oncogene products can be eliminated or reduced. Similarly, ribozymes can disrupt gene expression by selectively destroying messenger RNA before it is translated into protein. In some embodiments, cells are treated according to the invention using constructs that encode antisense or ribozymes as part of a therapeutic regimen which involves administration of other therapeutics and procedures. Gene constructs encoding antisense molecules and ribozymes use similar vectors as those which are used when protein production is desired except that the coding sequence does not contain a start codon to initiate translation of RNA into protein. In some embodiments, it is preferred that the vectors described in Example 46, particularly those which contain an origin of replication and expressible form of the appropriate nuclear antigen.

Ribozymes are catalytic RNAs which are capable of self-cleavage or cleavage of another RNA molecule. Several different types of ribozymes, such as hammerhead, hairpin, Tetrahymena group I intron, axhead, and RNase P are known in the art. (S. Edgington, *Biotechnology* 1992 10, 256-262.) Hammerhead ribozymes have a catalytic site which has been mapped to a core of less than 40 nucleotides. Several ribozymes in plant viroids and satellite RNAs share a common secondary structure and certain conserved nucleotides. Although these ribozymes naturally serve as their own substrate, the enzyme domain can be targeted to another RNA substrate through base-pairing with sequences flanking the conserved cleavage site. This ability to custom design ribozymes has allowed them to be used for sequence-specific RNA cleavage (G. Paolella et al., *EMBO* 1992, 1913-1919.) It will therefore be within the scope of one skilled in the art to use different catalytic sequences from various types of ribozymes, such as the hammerhead catalytic sequence and design them in the manner disclosed herein. Ribozymes can be designed against a variety of targets including pathogen nucleotide sequences and oncogenic sequences. Certain preferred embodiments of the invention include sufficient complementarity to specifically target the abl-bcr fusion transcript while maintaining efficiency of the cleavage reaction.

According to some embodiments of the present invention, cells are treated with compounds that facilitate uptake of genetic constructs by the cells. According to some embodiments of the present invention, cells are treated with compounds that stimulate cell division and facilitate uptake of genetic constructs. Administration of compounds that facilitate uptake of genetic constructs by the cells including cell stimulating compounds results in a more effective immune response against the target protein encoded by the genetic construct.

According to some embodiments of the present invention, the genetic construct is administered to an individual using a needleless injection device. According to some embodiments of the present invention, the genetic construct is simultaneously administered to an individual intradermally, subcutaneously and intramuscularly using a needleless injection device. Needleless injection devices are well known and widely available. One having ordinary skill in the art can, following the teachings herein, use needleless injection devices to deliver genetic material to cells of an individual. Needleless injection devices are well suited to deliver genetic material to all tissue. They are particularly useful to deliver genetic material to skin and muscle cells. In some embodiments, a needleless injection device may be used to propel a liquid that contains DNA molecules toward the surface of the individual's skin. The liquid is propelled at a sufficient velocity such that upon impact with the skin the liquid penetrates the surface of the skin, permeates the skin and muscle tissue therebeneath. Thus, the genetic material is simultaneously administered intradermally, subcutaneously and intramuscularly. In some embodiments, a needleless injection device may be used to deliver genetic material to tissue of other organs in order to introduce a nucleic acid molecule to cells of that organ.

According to the invention, the genetic vaccine may be administered directly into the individual to be immunized or ex vivo into removed cells of the individual which are reimplanted after administration. By either route, the genetic material is introduced into cells which are present in the body of the individual. Routes of administration include, but are not limited to, intramuscular, intraperitoneal, intradermal, subcutaneous, intravenous, intraarterially, intraoccularly and oral as well as transdermally or by inhalation or suppository. Preferred routes of administration include intramuscular, intraperitoneal, intradermal and subcutaneous injection. Delivery of gene constructs which encode target proteins can confer mucosal immunity in individuals immunized by a mode of administration in which the material is presented in tissues associated with mucosal immunity. Thus, in some examples, the gene construct is delivered by administration in the buccal cavity within the mouth of an individual.

Genetic constructs may be administered by means including, but not limited to, traditional syringes, needleless injection devices, or "microprojectile bombardment gene guns". Alternatively, the genetic vaccine may be introduced by various means into cells that are removed from the individual. Such means include, for example, ex vivo transfection, electroporation, microinjection and microprojectile bombardment. After the genetic construct is taken up by the cells, they are reimplanted into the individual. It is contemplated that otherwise non-immunogenic cells that have genetic constructs incorporated therein can be implanted into the individual even if the vaccinated cells were originally taken from another individual.

The genetic vaccines according to the present invention comprise about 1 nanogram to about 1000 micrograms of DNA. In some preferred embodiments, the vaccines contain about 10 nanograms to about 800 micrograms of DNA. In some preferred embodiments, the vaccines contain about 0.1 to about 500 micrograms of DNA. In some preferred embodiments, the vaccines contain about 1 to about 350 micrograms of DNA. In some preferred embodiments, the vaccines contain about 25 to about 250 micrograms of DNA. In some preferred embodiments, the vaccines contain about 100 micrograms DNA.

The genetic vaccines according to the present invention are formulated according to the mode of administration to be used. One having ordinary skill in the art can readily formulate a genetic vaccine that comprises a genetic construct. In cases where intramuscular injection is the chosen mode of administration, an isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation. The pharmaceutical preparations according to the present invention are provided sterile and pyrogen free.

The genetic constructs of the invention are formulated with or administered in conjunction with a polynucleotide function enhancer. Preferred co-agents according to the present invention are selected from the group consisting of benzoic acid esters, anilides, amidines, urethans and the hydrochloride salts thereof such as those of the family of local anesthetics.

The PFE may be a compound having one of the following formulae:

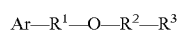

or

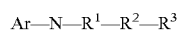

or $$R^4—N—R^5—R^6$$

or $$R^4—O—R^1—N—R^7$$

wherein:

Ar is benzene, p-aminobenzene, m-aminobenzene, o-aminobenzene, substituted benzene, substituted p-aminobenzene, substituted m-aminobenzene, substituted o-aminobenzene, wherein the amino group in the aminobenzene compounds can be amino, $C_1$-$C_5$ alkylamine, $C_1$-$C_5$, $C_1$-$C_5$ dialkylamine and substitutions in substituted compounds are halogen, $C_1$-$C_5$ alkyl and $C_1$-$C_5$ alkoxy;

$R^1$ is C=O;

$R^2$ is $C_1$-$C_{10}$ alkyl including branched alkyls;

$R^3$ is hydrogen, amine, $C_1$-$C_5$ alkylamine, $C_1$-$C_5$, $C_1$-$C_5$ dialkylamine;

$R^2$+$R^3$ can form a cyclic alkyl, a $C_1$-$C_{10}$ alkyl substituted cyclic alkyl, a cyclic aliphatic amine, a $C_1$-$C_{10}$ alkyl substituted cyclic aliphatic amine, a heterocycle, a $C_1$-$C_{10}$ alkyl substituted heterocycle including a $C_1$-$C_{10}$ alkyl N-substituted heterocycle;

$R^4$ is Ar, $R^2$ or $C_1$-$C_5$ alkoxy, a cyclic alkyl, a $C_1$-$C_{10}$ alkyl substituted cyclic alkyl, a cyclic aliphatic amine, a $C_1$-$C_{10}$ alkyl substituted cyclic aliphatic amine, a heterocycle, a $C_1$-$C_{10}$ alkyl substituted heterocycle and a $C_1$-$C_{10}$ alkoxy substituted heterocycle including a $C_1$-$C_{10}$ alkyl N-substituted heterocycle;

$R^5$ is C=NH;

$R^6$ is Ar, $R^2$ or $C_1$-$C_5$ alkoxy, a cyclic alkyl, a $C_1$-$C_{10}$ alkyl substituted cyclic alkyl, a cyclic aliphatic amine, a $C_1$-$C_{10}$ alkyl substituted cyclic aliphatic amine, a heterocycle, a $C_1$-$C_{10}$ alkyl substituted heterocycle and a $C_1$-$C_{10}$ alkoxy substituted heterocycle including a $C_1$-$C_{10}$ alkyl N-substituted heterocycle; and.

$R^7$ is Ar, $R^2$ or $C_1$-$C_5$ alkoxy, a cyclic alkyl, a $C_1$-$C_{10}$ alkyl substituted cyclic alkyl, a cyclic aliphatic amine, a $C_1$-$C_{10}$ alkyl substituted cyclic aliphatic amine, a heterocycle, a $C_1$-$C_{10}$ alkyl substituted heterocycle and a $C_1$-$C_{10}$ alkoxy substituted heterocycle including a $C_1$-$C_{10}$ alkyl N-substituted heterocycle.

Examples of esters include: benzoic acid esters such as piperocaine, meprylcaine and isobucaine; para-aminobenzoic acid esters such as procaine, tetracaine, butethamine, propoxycaine and chloroprocaine; meta-aminobenzoic acid esters including metabuthamine and primacaine; and para-ethoxybenzoic acid esters such as parethoxycaine. Examples of anilides include lidocaine, etidocaine, mepivacaine, bupivacaine, pyrrocaine and prilocaine. Other examples of such compounds include dibucaine, benzocaine, dyclonine, pramoxine, proparacaine, butacaine, benoxinate, carbocaine, methyl bupivacaine, butasin picrate, phenacaine, diothan, luccaine, intracaine, nupercaine, metabutoxycaine, piridocaine, biphenamine and the botanically-derived bicyclics such as cocaine, cinnamoylcocaine, truxilline and cocaethylene and all such compounds complexed with hydrochloride.

In preferred embodiments, the PFE is bupivacaine. The difference between bupivacaine and mepivacaine is that bupivacaine has a N-butyl group in place of an N-methyl group of mepivacaine. Compounds may have at that N, $C_1$-$C_{10}$. Compounds may be substituted by halogen such as procaine and chloroprocaine. The anilides are preferred.

Bupivacaine is administered prior to, simultaneously with or subsequent to the genetic construct. Bupivacaine and the genetic construct may be formulated in the same composition. Bupivacaine is particularly useful as a cell stimulating agent in view of its many properties and activities when administered to tissue. Bupivacaine promotes and facilitates the uptake of genetic material by the cell. As such, it is a transfecting agent. Administration of genetic constructs in conjunction with bupivacaine facilitates entry of the genetic constructs into cells. Bupivacaine is believed to disrupt or otherwise render the cell membrane more permeable. Cell division and replication is stimulated by bupivacaine. Accordingly, bupivacaine acts as a replicating agent. Administration of bupivacaine also irritates and damages the tissue. As such, it acts as an inflammatory agent which elicits migration and chemotaxis of immune cells to the site of administration. In addition to the cells normally present at the site of administration, the cells of the immune system which migrate to the site in response to the inflammatory agent can come into contact with the administered genetic material and the bupivacaine. Bupivacaine, acting as a transfection agent, is available to promote uptake of genetic material by such cells of the immune system as well.

Bupivacaine is related chemically and pharmacologically to the aminoacyl local anesthetics. It is a homologue of mepivacaine and related to lidocaine. Bupivacaine renders muscle tissue voltage sensitive to sodium challenge and effects ion concentration within the cells. A complete description of bupivacaine's pharmacological activities can be found in Ritchie, J. M. and N. M. Greene, *The Pharmacological Basis of Therapeutics*, Eds.: Gilman, A. G. et al, 8th Edition, Chapter 15:3111, which is incorporated herein by reference. Bupivacaine and compounds that display a functional similarity to bupivacaine are preferred in the method of the present invention.

Bupivacaine-HCl is chemically designated as 2-piperidinecarboxamide, 1-butyl-N-(2,6-dimethylphenyl)-monohydrochloride, monohydrate and is widely available commercially for pharmaceutical uses from many sources including from Astra Pharmaceutical Products Inc. (Westboro, Mass.) and Sanofi Winthrop Pharmaceuticals (New York, N.Y.), Eastman Kodak (Rochester, N.Y.). Bupivacaine is commercially formulated with and without methylparaben and with or without epinephrine. Any such formulation may be used. It is commercially available for pharmaceutical use in concentration of 0.25%, 0.5% and 0.75% which may be used on the invention. Alternative concentrations, particularly those between 0.05%-1.0% which elicit desirable effects may be prepared if desired. According to the present invention, about 250 µg to about 10 mg of bupivacaine is administered. In some embodiments, about 250 µg to about 7.5 mg is administered. In some embodiments, about 0.05 mg to about 5.0 mg is administered. In some embodiments, about 0.5 mg to about 3.0 mg is administered. In some embodiments about 5 to 50 µg is administered. For example, in some embodiments about 50 µl to about 2 ml, preferably 50 µg to about 1500 µg and more preferably about 1 ml of 0.5% bupivacaine-HCl and 0.1% methylparaben in an isotonic pharmaceutical carrier is administered at the same site as the vaccine before, simultaneously with or after the vaccine is administered. Similarly, in some embodiments, about 50 µg to about 2 ml, preferably 50 µg to about 1500 µl and more preferably about 1 ml of 0.5% bupivacaine-HCl in an isotonic pharmaceutical carrier is administered at the same site as the vaccine before, simultaneously with or after the vaccine is administered. Bupivacaine and any other similarly acting compounds, particularly those of the related family of local anesthetics may be administered at concentrations which provide the desired facilitation of uptake of genetic constructs by cells.

In some embodiments of the invention, the individual is first subject to bupivacaine injection prior to genetic vaccination by intramuscular injection. That is, up to, for example, up to a about a week to ten days prior to vaccination, the individual is first injected with bupivacaine. In some embodiments, prior to vaccination, the individual is injected with bupivacaine about 1 to 5 days before administration of the genetic construct. In some embodiments, prior to vaccination, the individual is injected with bupivacaine about 24 hrs before administration of the genetic construct. Alternatively, bupivacaine can be injected simultaneously, minutes before or after vaccination. Accordingly, bupivacaine and the genetic construct may be combined and injected simultaneously as a mixture. In some embodiments, the bupivacaine is administered after administration of the genetic construct. For example, up to about a week to ten days after administration of the genetic construct, the individual is injected with bupivacaine. In some embodiments, the individual is injected with bupivacaine about 24 hrs after vaccination. In some embodiments, the individual is injected with bupivacaine about 1 to 5 days after vaccination. In some embodiments, the individual is administered bupivacaine up to about a week to ten days after vaccination.

Other agents which may function transfecting agents and/or replicating agents and/or inflammatory agents and which may be co-administered with bupivacaine and similar acting compounds include lectins, growth factors, cytokines and lymphokines such as α-interferon, gamma-interferon, platelet derived growth factor (PDGF), GC-SF, GM-CSF, TNF, epidermal growth factor (EGF), IL-1, IL-2, IL-4, IL-6, IL-8, IL-10 and IL-12 as well as collagenase, fibroblast growth factor, estrogen, dexamethasone, saponins, surface active agents such as immune-stimulating complexes (ISCOMS), Freund's incomplete adjuvant, LPS analog-including monophosphoryl Lipid A (MPL), muramyl peptides, quinone analogs and vesicles such as squalene and squalene, hyaluronic acid and hyaluronidase may also be used administered in conjunction with the genetic construct. In some embodiments, combinations of these agents are administered in conjunction with bupivacaine and the genetic construct. For example, bupivacaine and either hyaluronic acid or hyaluronidase are co-administered with a genetic construct.

The genetic construct may be combined with collagen as an emulsion and delivered parenterally. The collagen emulsion provides a means for sustained release of DNA. 50 μl to 2 ml of collagen are used. About 100 μg DNA are combined with 1 ml of collagen in a preferred embodiment using this formulation. Other sustained release formulations such as those described in *Remington's Pharmaceutical Sciences*, A. Osol, a standard reference text in this field, which is incorporated herein by reference. Such formulations include aqueous suspensions, oil solutions and suspensions, emulsions and implants as well as reservoirs and transdermal devices. In some embodiments, time release formulations for genetic constructs are preferred. In some embodiments, it is preferred that the genetic construct is time released between 6-144 hours, preferably 12-96 hours, more preferably 18-72 hours.

In some embodiments of the invention, the genetic construct is injected with a needleless injection device. The needleless injection devices are particularly useful for simultaneous administration of the material intramuscularly, intradermally and subcutaneously.

In some embodiments of the invention, the genetic construct is administered with a PFE by means of a microprojectile particle bombardment procedure as taught by Sanford et al. in U.S. Pat. No. 4,945,050 issued Jul. 31, 1990, which is incorporated herein by reference.

In some embodiments of the invention, the genetic construct is administered as part of a liposome complex with a polynucleotide function enhancing agent.

In some embodiments of the invention, the individual is subject to a single vaccination to produce a full, broad immune response. In some embodiments of the invention, the individual is subject to a series of vaccinations to produce a full, broad immune response. According to some embodiments of the invention, at least two and preferably four to five injections are given over a period of time. The period of time between injections may include from 24 hours apart to two weeks or longer between injections, preferably one week apart. Alternatively, at least two and up to four separate injections are given simultaneously at different sites.

In some embodiments of the invention, a complete vaccination includes injection of a single inoculant which contains a genetic construct including sequences encoding one or more targeted epitopes.

In some embodiments of the invention, a complete vaccination includes injection of two or more different inoculants into different sites. For example, in an HIV vaccine according to the invention, the vaccine comprises two inoculants in which each one comprises genetic material encoding different viral proteins. This method of vaccination allows the introduction of as much as a complete set of viral genes into the individual without the risk of assembling an infectious viral particle. Thus, an immune response against most or all of the virus can be invoked in the vaccinated individual. Injection of each inoculant is performed at different sites, preferably at a distance to ensure no cells receive both genetic constructs. As a further safety precaution, some genes may be deleted or altered to further prevent the capability of infectious viral assembly. As used herein, the term "pharmaceutical kit" is meant to collectively refer to multiple inoculant used in the present invention. Such kits include separate containers containing different inoculants and/or cell stimulating agents. It is intended that these kits be provided to include a set of inoculants used in an immunizing method.

The methods of the present invention are useful in the fields of both human and veterinary medicine. Accordingly, the present invention relates to genetic immunization of mammals, birds and fish. The methods of the present invention can be particularly useful for mammalian species including human, bovine, ovine, porcine, equine, canine and feline species.

The Examples set out below include representative examples of aspects of the present invention. The Examples are not meant to limit the scope of the invention but rather serve exemplary purposes. In addition, various aspects of the invention can be summarized by the following description. However, this description is not meant to limit the scope of the invention but rather to highlight various aspects of the invention. One having ordinary skill in the art can readily appreciate additional aspects and embodiments of the invention.

EXAMPLES

Example 1

The present invention provides an HIV vaccine using direct genetic immunization. Genetic constructs are provided which, when delivered into the cells of an individual, are expressed to produce HIV proteins. According to some embodiments, the production of all viral structural proteins in the cells of the individual elicit a protective immune response which protects against HIV infection. The HIV vaccine of the present invention may be used to immunize uninfected individuals from HIV infection or serve as an immunotherapeutic for those individuals already infected. The HIV vaccine of the present invention invokes an immune response including CTLs which recognize and attack HIV infected cells and recognize the widest contingent of HIV protein. Thus, uninfected individuals are protected from HIV infection.

In some embodiments, the present invention relates to a method of immunizing an individual against HIV by administering two inoculants. These two inoculants comprise at least two and preferably more than two, a plurality or all of the genes of the HIV virus. However, the inoculants are not delivered together. Accordingly, an inoculated cell will not be administered a complete complement of genes. The vaccinated individual will receive at least two different and preferably more than two, more preferably a plurality or all of the viral genes. Immune responses can then be directed at the total complement of HIV protein target.

This strategy increases the probability that genetic material encoding the most effective target protein will be included in the vaccine and reduces the likelihood that a viral particle will escape detection by the immune response despite structural changes in one or more viral proteins which occur when the virus undergoes mutation. Accordingly, it is desirable to vaccinate an individual with multiple and preferably a nearly complete or complete complement of genes encoding viral proteins.

If a single cell is provided with a complete complement of viral genes, it is possible that a complete infectious virus can be assembled within the cell. Accordingly, a genetic construct according to the present invention is not provided with such a full complement of genes. Furthermore, two or more inoculants, each having an incomplete set of genes and combined having up to a full complement of viral genes, are administered to different cells, preferably at a distant site from each other to ensure that no vaccinated cell will inadvertently be exposed to a full set of genes. For example, a portion of the HIV genome may be inserted into a first construct and the remaining portion of the HIV genome is inserted in a second construct. The first construct is administered to an individual as a genetic vaccine in the muscle tissue of one arm while the second construct is administered to an individual as a genetic vaccine in the muscle tissue of the individual's other arm. The individual may be exposed to a full set of viral genes; thus essentially vaccinating against the whole virus but with no risk that an infectious viral particle will be assembled.

As an additional safety precaution, even when genetic material is delivered by two or more inoculants at distant parts of the individual's body, one or more essential genes can be deleted or intentionally altered to further ensure that an infectious viral particle cannot be formed. In such embodiments, the individual is not administered a complete functional set of viral genes.

A further safety precaution provides non-overlapping portions of the viral genome on the separate genetic constructs that make up the separate inoculants respectively. Accordingly, recombination between the two genetic constructs is prevented.

In some embodiments of the present invention, a full complement of structural genes are provided. The structural genes of HIV consist of gag, pol and env. These three genes are provided on two different DNA or RNA constructs. Accordingly, in one preferred embodiment, gag and pol are on one DNA or RNA construct and env is on another. In another preferred embodiment, gag is on one DNA or RNA construct and pol and env is on the other. In another preferred embodiment, gag and env are on one DNA or RNA construct and pol is on the other. In some preferred embodiments, constructs that contain rev have a splice acceptor upstream of the start codon for rev. In some preferred embodiments, constructs that contain gag have a splice donor upstream of the gag translational start codon. Optionally, in any of these combinations, HIV regulatory genes may also be present. The HIV regulatory genes are: vpr, vif, vpu, nef, tat and rev.

The DNA construct in a preferred embodiment consists of a promoter, an enhancer and a polyadenylation signal. The promoter may be selected from the group consisting of: HIV LTR, human Actin, human Myosin, CMV, RSV, Moloney, MMTV, human Hemoglobin, human muscle creatine and EBV. The enhancer may be selected from the group consisting of: human Actin, human Myosin, CMV, RSV, human Hemoglobin, human muscle creatine and EBV. The polyadenylation signal may be selected from the group consisting of: LTR polyadenylation signal and SV40 polyadenylation signal, particularly the SV40 minor polyadenylation signal among others.

In some embodiments, the two inoculant vaccine is administered intramuscularly at spatially segregated tissue of the individual, preferably in different appendages, such as for example in the right and left arms. Each inoculant of the present invention may contain from about 0.1 to about 1000 micrograms of DNA. Preferably, each inoculant contains about 1 to about 500 micrograms of DNA. More preferably, each inoculant contains about 25 to about 250 micrograms of DNA. Most preferably, each inoculant contains about 100 micrograms DNA.

The inoculant in some embodiments is in a sterile isotonic carrier, preferably phosphate buffered saline or saline solution.

In some embodiments, prior to vaccine administration, the tissue to be vaccinated is injected with a cell proliferating agent, preferably bupivacaine. Bupivacaine injections may be performed up to about 24 hours prior to vaccination. It is contemplated that bupivacaine injection will occur immediately before vaccination. About 50 µg to about 2 ml of 0.5% bupivacaine-HCl and 0.1% methylparaben in isotonic NaCl is administered to the site where the vaccine is to be administered, preferably, 50 µg to about 1500 µg, more preferably about 1 ml.

In other embodiments, a cell proliferating agent, preferably bupivacaine is included in the formulation together with the genetic construct. About 50 µg to about 2 ml of 0.5% bupivacaine-HCl and 0.1% methylparaben in isotonic NaCl is administered to the site where the vaccine is to be administered, preferably, 50 µl to about 1500 µl, more preferably about 1 ml.

Accordingly, some embodiments comprise a two inoculant vaccine: one inoculant comprising a DNA or RNA construct having two HIV structural genes, the other inoculant comprising a DNA or RNA construct having the third, remaining HIV structural gene such that the combined inoculants contain a full complement of HIV structural genes. The structural genes on each DNA construct are operably linked to a promoter, an enhancer and a polyadenylation signal. The same or different regulatory elements may control expression of the viral genes. When vaccinating an individual, the two inoculants are administered intramuscularly to different sites, preferably on different arms. In some embodiments of the invention, bupivacaine is first administered at the site where inoculant is to be administered. In some embodiments of the invention, bupivacaine is included in the formulations together with the genetic constructs.

In some embodiments, the vaccination procedure is repeated at least once and preferably two or three times. Each vaccination procedure is performed from 24 hours to two months apart.

In some embodiments, the vaccine is administered using a needleless injection device. In some embodiments, the vaccine is administered hypodermically using a needleless injection device thus providing intramuscular, intradermal, subcutaneous administration simultaneously while also administering the material interstitially.

Preferred genetic constructs include the following.

Plasmids and Cloning Strategies:

Two plasmids were constructed: one which contains HIV gag/pol and the other which contains HIV env.

The HIV-1 genomic clone pNL43 was obtained through the NIH AIDS Research and Reference Reagent Program (ARRRP), Division of AIDS, NIAID, NIH, from Dr. Malcolm Martin, and can be used as the starting material for HIV-1 viral genes for genetic constructs. Alternatively, any HIV molecular clone of infected cell can, through use of the polymerase chain technology, be modified sufficiently for construction including the HXB2 clone the MN clone as well as the SF or BAL-1 clone. The pNL43 clone is a construct that consists of HIV-1 proviral DNA plus 3 kb of host sequence from the site of integration cloned into pUC18.

Construction of pNL-puro-env⁻ Plasmid:

This plasmid was constructed for expression of gag pol. The StuI site within the non-HIV 5' flanking human DNA of pNL43 was destroyed by partial digestion with StuI followed by digestion of the free ends with $E.\ coli$ polymerase 1. The linear plasmid was filled and then self ligated, leaving a unique StuI site within the HIV genome. This plasmid, pNLDstu, was then digested with the blunting enzymes StuI and BsaBI which eliminated a large section of the coding sequence for gp120. The SV40 promoter and puromycin resistance coding region (puromycin acetyl transferase (PAC)) were isolated from pBABE-puro (Morgenstern and Land, 1990 $Nucl.\ Acids\ Res.$ 18(12):3587-3596, which is incorporated herein by reference, kindly provided by Dr. Hartmut Land of the Imperial Cancer Research Fund) using EcoRI and ClaI. This fragment was blunted, then cloned into the StuI/BsaBI-digested pNLDstu. A clone was selected with the SV40-puro fragment in the correct orientation so that the 3' LTR of HIV could provide poly A functions for the PAC message. This plasmid was designated pNLpuro.

Cloning Strategy for Deletion of vpr Regulatory Gene from the HIV Gag Pol Vector:

A region from just upstream of the unique PflMI site to just after the vif termination codon was amplified via PCR using primers that introduced a non-conservative amino acid change (glu→val) at amino acid 22 of vpr, a stop codon in the vpr reading frame immediately after amino acid 22, and an EcoRI site immediately following the new stop codon. This PCR fragment was substituted for the PflMI-EcoR I fragment of pNLpuro or pNL43. This substitution resulted in the deletion of 122 nucleotides of the open reading frame of vpr, thus eliminating the possibility of reversion that a point mutation strategy entails. The resulting plasmids, pNLpuroΔvpr, encode the first 21 natural amino acids of vpr plus a valine plus all other remaining HIV-1 genes and splice junctions in their native form. Such deletion strategy would also be applicable to nef, vif, and vpu and allow for structural gene expression but protect from the generation of a live recombinant virus.

Plasmid Construction for Envelope Expression:

The DNA segment encoding the envelope gene of HIV-1 HXB2 was cloned by the polymerase chain reaction (PCR) amplification technique utilizing the lambda cloned DNA obtained from the AIDS Research and Reference Reagent Program. The sequences of the 5' and 3' primers are 5'-AG-GCGTCTCGAGACAGAGGAGAGCAAGAAATG-3' (SEQ ID NO:1) with incorporation of XhoI site and 5'-TTTC-CCTCTAGATAAGCCATCCAATCACAC-3' (SEQ ID NO: 2) with incorporation of XbaI site, respectively, which encompass gp160, tat and rev coding region. Gene specific amplification was performed using Taq DNA polymerase according to the manufacturer's instructions (Perkin-Elmer Cetus Corp.). The PCR reaction products were treated with 0.5 µg/ml proteinase K at 37° C. for thirty minutes followed by a phenol/chloroform extraction and ethanol precipitation. Recovered DNA was then digested with XhoI and XbaI for two hours at 37° C. and subjected to agarose gel electrophoresis. The isolated and purified XhoI-XbaI PCR fragment was cloned into Bluescript plasmid (Stratagene Inc., La Jolla, Calif.) and then subcloned into the eukaryotic expression vector pMAMneoBlue (Clontech Laboratories, Inc., Palo Alto, Calif.). The resulting construct was designated as pM160 (FIG. 1A). The plasmid DNA was purified with CsCl gradient ultracentrifugation. The DNA construct pM160 encodes the HIV-1/HXB2 (Fisher, A. G., et al., (1985) $Nature$ 316:262-265) gp160 membrane bound glycoprotein under control of a RSV enhancer element with the MMTV LTR as a promoter.

An Alternative Envelope Expression Plasmid Construction called HIV-1 env-rev Plasmid:

The region encoding the two exons of rev and the vpu and envelope open reading frames of HIV-1 HXB2 was amplified via PCR and cloned into the expression vector pCNDA/neo (Invitrogen). This plasmid drives envelope production through the CMV promoter.

Production and Purification:

The plasmid in $E.\ coli$ (DH5 alpha) is grown up as follows: An LB plus ampicillin agar plate is streaked with the desired plasmid culture from frozen stock. The plate is incubated overnight (14-15 hours) at 37° C. A single colony is taken from the plate and inoculated into 15 ml of LB medium with a peptone preparation and 50 µg/ml ampicillin. This culture is grown at 37° C. while being shaken (ca. 175 rpm) for 8-10 hours. $OD_{600}$ readings should be at least 1.0. 1 liter of LB medium with peptone and 50 µg/ml ampicillin is inoculated with 1.0 OD of culture. These 1-2 liter cultures are grown overnight at 37° C. while being shaken (175 rpm).

Plasmid grown in $E.\ coli$ (strain DH5 alpha) are harvested and purified by the following methods. General procedures for the lysis of cells and purification of plasmid can be found in "Molecular Cloning: A Laboratory Manual", 2nd Edition, J. Sambrook, E. F. Fritsch, and T. Maniatis, Cold Spring Harbor Press, 1989. The cells are concentrated and washed with glucose-tris-EDTA pH 8.0 buffer. The concentrated cells are lysed by treatment with lysozyme and briefly treated with 0.2 N KOH, the pH is then adjusted 5.5 with potassium acetate/acetic acid buffer. Insoluble material is removed by centrifugation. To the supernatant is added 2-propanol to precipitate the plasmid. The plasmid is redissolved in tris-EDTA buffer and further purified by phenol/chloroform extraction and an additional precipitation with 2-propanol.

Endotoxin can optionally be removed by a variety of methods including the following: specific adsorption by immobilized materials such as polymyxin (Tani et al., $Biomater.\ Artif.\ Cells\ Immobilization\ Biotechnol.$ 20(2-4):457-62 (1992); Issekutz, $J.\ Immunol.\ Methods$ 61(3):275-81 (1983)); anti-endotoxin monoclonal antibodies, such as 8A1 and HA-1A™ (Centocor, Malvern, Pa.; Bogard et al. $J.\ Immunol.$ 150(10): 4438-4449 (1993); Rietschel et al., $Infect.\ Immunity$ page 3863 (1993)); positively charged depth filters (Hou et al., $J.\ Parenter.\ Sci.\ Technol.$ 44(4):204-9 (July-August 1990)); poly(gamma-methyl L-glutamate), Hirayama et al., $Chem.\ Pharm.\ Bull.$ (Tokyo) 40(8):2106-9 (1992)); histidine (Matsumae et al., $Biotechnol.\ Appl.\ Biochem.$ 12:(2):129-40 (1990)); hydrophobic interaction columns and membranes (Aida et al., *J. Immunol Methods* 132(2):191-5 (1990); Umeda et al., *Biomater Artif Cells Artif Organs* 18(4):491-7 (1990); Hou et al., *Biochem. Biophys. Acta* 1073(1):149-54 (1991); Sawada et al., *J. Hyg.* (London) 97(1):103-14 (1986)); specific hydrophobic resins useful for removing endotoxin including hydrophobic polystyrene/divinylbenzene or divinylbenzene resins such as Brownlee Polypore Resin (Applied Biosystems, Palo Alto, Calif.); XUS 40323.00 (Dow Chemical, Midland, Mich.); HP20, CHP20P (Mitsubishi Kasei, U.S.); Hamilton PRP-1, PRP-infinity (Hamilton, Reno, Nev.); Jordi Reversed-Phase DVB, Jordi Gel DVB, Polymer Labs PLgel™ (Alltech, Deerfield, Ill.); Vydac PLx™ (Separations Group, Hesperia, Calif.); other endotoxin removing materials and methods include Detoxi-Gel™ Endotoxin Removing Gel (Pierce Chemical, Rockford, Ill.); Application Note 206, (Pharmacia Biotech Inc, Piscataway, N.J.). See also generally, Sharma, *Biotech. App. Biochem.* 8:5-22 (1986). Preferred anti-endotoxin monoclonal antibodies bind to the conserved domains of endotoxin, preferably antibodies to lipid A, the most structurally conserved portion of the endotoxin molecule. Such anti-lipid A monoclonal antibodies include the high affinity murine IgG monoclonal antibody 8A1 and the human anti-lipid A IgM(k) monoclonal antibody HA-1A™. HA-1A™ was derived from a human B *E. coliJ* 5 vaccine. HA-1A™. HA-1A™ is reported to be broadly cross-reactive with a variety of bacterial endotoxins (lipopolysaccharides).

Example 2

In experiments designed to compare the immunogenic response elicited by genetic vaccination and protein vaccination, animal models were designed using tumor cells that specifically express a foreign target protein. Three immune competent mouse models have been developed which express foreign antigens. Three clonal tumor cell lines which are derived from the Balb/c mouse strain are used. The cell lines are: 1) a lymphoid cell line which does not metastasize significantly to other tissues but forms large palpable tumors which appear to kill the animal within an 8-12 week period; 2) a murine melanoma cell line with some ability to metastasize, mostly to the lung, and in which, following inoculation with 1 million cells, results in the development in the mice of large palpable tumors which similarly kill the animal within 10-12 weeks; and 3) a murine lung adenocarcinoma cell line which metastasizes to multiple tissues and kills the animal within 12 or more weeks. Subclones have been selected which can display foreign antigens in an unrecognized form. When transfected tumors are implanted into a parent mouse strain, unlike the majority of similar murine tumor lines, the animals do not make a protective immune response to the foreign antigens displayed and the tumors are accepted. These tumors then kill the animal with the same phenotype in the same time frame as the original untransfected tumor. Using these models, the immune response elicited by genetic vaccination against an antigen can be measured.

It was observed that mice vaccinated with a genetic vaccine comprising a genetic construct that resulted in production of the target protein by the cell's of the mouse elicited an immune response including a strong cytotoxic that completely eliminated tumors displaying the target protein but with no effect on tumors that did not. In mice inoculated with the target protein itself, the immune response elicited thereby was much less effective. The tumors were reduced in size but, due to an absence of a cytotoxic response, they were not eliminated. As controls, untransfected tumors were used in experiments comparing the immune response of animals vaccinated with the genetic vaccine, subunit vaccine and unvaccinated animals. These experiments clearly demonstrate that the genetic vaccine produced a broader, more effective immune response which was capable, by virtue of CTL's, of completely eliminating tumors. By contrast, immunization using intact target protein produced a more limited, less effective immune response.

Example 3

In another embodiment of the invention, a genetic vaccine against HIV has been designed. The viral protein gp160, which is processed into gp120 and gp41, is the target protein against which a genetic vaccine is produced. The genetic vaccine contains a DNA construct that comprises a DNA sequence encoding gp160 operably linked regulatory elements. When administered to an individual, the DNA construct of the genetic vaccine is incorporated into the cells of the individual and gp160 is produced. The immune response that is elicited by the protein is broad based and includes the humoral and both arms of the cellular immune response. The broad biological response provides superior protection to that achieved when the protein itself is administered.

Mice were injected intramuscularly with pM160, described in Example 1, and subsequently analyzed for anti-HIV immune responses. The antisera from animals immunized in this manner produce anti-HIV envelope glycoprotein immune responses as measured by enzyme linked immunosorbent assay (ELISA) and immunoprecipitation assays. The antisera neutralizes HIV-1 infection and inhibits HIV-1 induced syncytium formation.

The observed neutralization and anti-syncytial activity may be the result of reactivity of the elicited antibodies to functionally important regions of the HIV-1 envelope protein, such as the V3 loop of gp120, CD4 binding site and the N-terminal "immunodominant" region of gp41, among others.

In the genetic immunization procedure described herein, the quadriceps muscles of BALB/c mice were injected with 100 µl of 0.5% bupivacaine-HCl and 0.1% methylparaben in isotonic NaCl using a 27-gauge needle to stimulate muscle cell regeneration and facilitate uptake of the genetic construct. Twenty-four hours later, the same injection sites were then injected with either 100 µg of pM160 or with 100 µg of pMAMneoBlue as a control plasmid (FIG. 1A). The mice were boosted by injecting the same amount of DNA construct three times at two week intervals in the same manner but without pre-treatment with bupivacaine-HCl.

For the recombinant gp160 immunization, BALB/C mice were initially immunized with 1 µg of glycosylated recombinant (HIV-1/III$_B$) gp160 (MicroGeneSys Inc.) in complete Freund's adjuvant followed by three boosters of 1 µg of gp160 each in incomplete Freund's adjuvant at two week intervals. The production of antibody against HIV-1 gp160 was determined by testing the mouse sera for their ability to immunoprecipitate gp160. Immunoprecipitation was performed using 1×10$^6$ cpm of $^{125}$I labeled rgp160, mouse sera and protein-G agarose beads (GIBCO, Inc.) as previously described by Osther, K., et al., (1991) *Hybridoma* 10:673-683, which is incorporated herein by reference. The specific precipitations were analyzed by 10% SDS-PAGE. Lane 1 is 1 µg of preimmune mouse serum reacted with the $^{125}$I-gp160. Lane 2 is 1 µg of mouse serum immunized from the pM160 immunized mice. Lane 3 is 1 µg of 1:100 dilution of ID6 monoclonal anti-gp120 antibody (Ugen, K. E., et al., (1992) *Generation of Monoclonal Antibodies Against the Amino Region of gp*120 *Which Elicits Antibody Dependent Cellular*

*Cytotoxicity*, Cold Spring Harbor Laboratory) as a positive control. The arrow indicates the specifically immunoprecipitated $^{125}$I-gp160 envelope glycoprotein.

Figure 2:
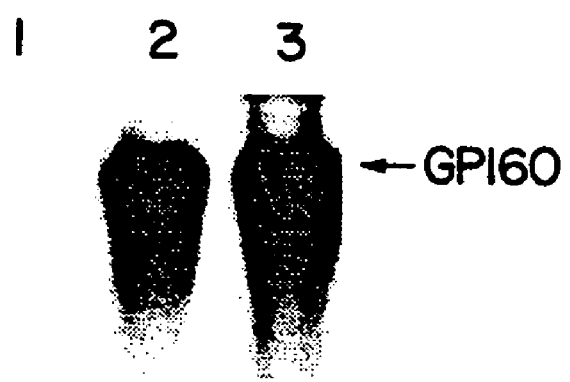
FIG. 2 is a photograph of an autoradiogram showing immunoprecipitations of serum antibodies binding to $^{125}$I-gp160.

$^{125}$I-labelled gp160 was specifically immunoprecipitated with antisera derived from the pM160-immunized animals (FIG. 2, lane 2) as well as the positive control anti-gp120 monoclonal antibody, ID6 (FIG. 2, lane 3). In contrast, the preimmune sera (FIG. 2, lane 1) only showed minimal activity in the same assay.

Eight of ten mice immunized with the pM160 construct were positive for reactivity against gp160 as determined by ELISA and the immune responses from the animal with the highest anti-gp160 titer was analyzed in detail. Four mice immunized with the control vector all showed a similar negative reactivity to gp160 in ELISA and one of these sera was used as the control for subsequent experiments.

It has been shown that HIV neutralizing antibodies are specifically targeted to several epitopes in gp120 and gp41, which include the V3 loop in gp120 (Goudsmit, J. et al., (1988) *AIDS* 2:157-164; and Putney, S. D., et al., (1989) *Development Of An HIV Subunit Vaccine*, Montreal), the CD4 binding site near the carboxy terminus of gp120 (Lasky, L. A., et al., (1987) *Cell* 50:975-985) as well as the immunodominant loop of gp41 just downstream of the N-terminal fusion region (Schrier, R. D., et al., (1988) *J. Virol.* 62:2531-2536).

Figure 3A:
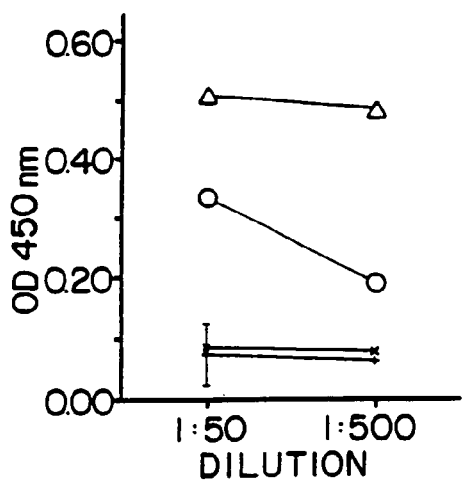
FIGS. 3A-3E are graphs showing ELISA results binding different sera to various proteins immobilized on microtiter plates.
Figure 3B:
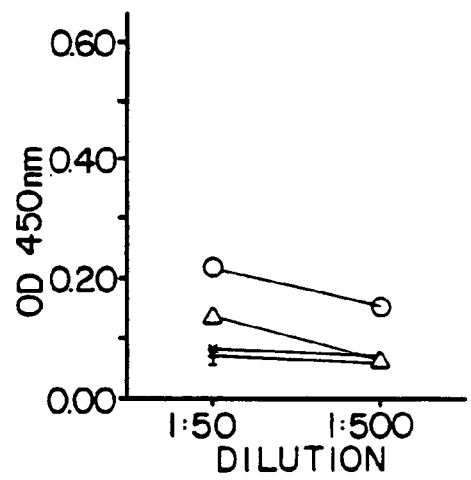
Figure 3C:
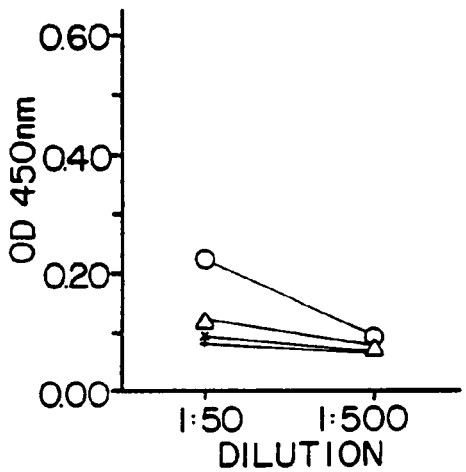
Figure 3D:
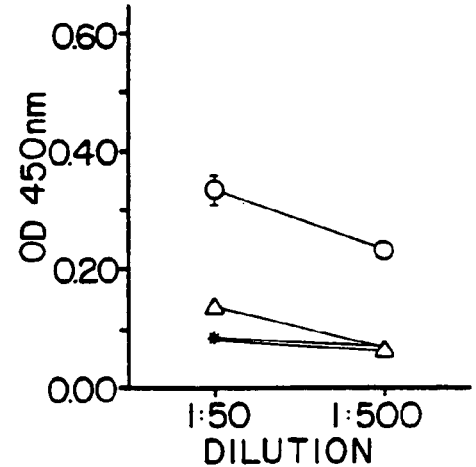
Figure 3E:
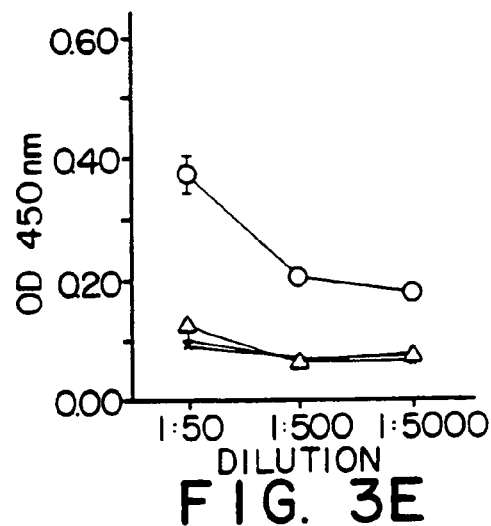

To determine whether the anti-gp160 antibodies elicited in these mice are reactive to these important regions of the envelope glycoproteins, peptides for the BRU/V3 loop, peptides for the MN/V3 loop, peptides for the HXB2/gp41 N-terminus or peptides for HXB2/CD4 binding site were absorbed to microtiter plates and specific reactivities of the mouse antisera determined in ELISA assays. One µg/ml of gp160 or 10 µg/ml of each peptide was coated to microtiter plates in 0.1M bicarbonate buffer (pH 9.5) overnight at 4° C., blocked with 2% bovine serum albumin in PBS, and reacted with goat anti-mouse IgG conjugated with HRPO (Fisher) for one hour at 37° C. and developed with TMB substrate (Sigma) for 10-30 minutes at room temperature in the dark. Results are reported in FIG. 3. Antisera were as follows: (-+-) is preimmune sera, (-x-) is the pMAMneoBlue vector immunized sera, (-O-) is the pM160 immunized sera, (-Δ-) is from mice immunized with the rgp160 protein. FIG. 3A shows results using a rgp160 protein coated plate. FIG. 3B shows results using a BRU/V3 loop peptides (CNTRKRIRIQRG-PGRAFVTIGK (SEQ ID NO:11)) coated plate. FIG. 3C shows results using a plate coated with MN/V loop peptides (YNKRKRIHIQRGPGRAFYTTKNIIC (SEQ ID NO:12)) with the QR sequence from HIV-1/III$_B$ in bold-faced type. FIG. 3D shows the results using a HXB2/CD4 binding site peptides (CRIKQFINMWQEVGKAMYAPPISGIRC (SEQ ID NO:13)) coated plate. FIG. 3E shows the results using a BRU/gp41 immunodominant region peptides (RILAVERY-IKDQQLLGIWGCSGKLIC (SEQ ID NO:14)) coated plate.

FIG. 3 shows that antiserum from the pM160 construct immunized mouse has significantly higher reactivity to the BRU and MN/V3 loop peptides, the CD4 binding site peptide and the immunodominant gp41 peptide than the recombinant gp160 protein (rgp160) immunized serum. The antiserum from the rgp160 immunized mouse had much higher titer against the rgp160 than the pM160 immunized antiserum, but lower activity against the three specific neutralization epitopes of gp160 tested.

To determine whether the antisera generated by DNA immunization possessed antiviral activity, the ability of the antisera to neutralize HIV-1 infection was examined. Cell-free HIV-1/III$_B$ virus at 100 TCID$_{50}$ was incubated with serial dilutions of the antisera before being used to infect MT-2 target cells (Montefiori, D. C., (1988) *J. Clin., Microbio.* 26:231-235).

One hundred TCID$_{50}$HIV-1/III$_B$ cell-free virus was preincubated with serial dilutions of antisera for one hour at 37° C. Following incubation the pretreated virus was then plated on the 4×10$^4$ of target cell line, MT-2 for one hour at 37° C., following infection the MT-2 cells were washed three times and then incubated at 37° C. at 5% CO$_2$. Fusion was evaluated three days later quantitatively by visually counting the number of syncytia per well in triplicate experiments under a phase contrast microscope.

The results are reported in FIG. 4. FIG. 4A shows the results using vector-immunized mouse sera compared with FIG. 4B which shows the results using pM160 immunized sera. Neutralization values ($V_n/V_o$) versus the dilution factors (Nara, P., (1989) *Techniques In HIV Research* eds. Aldovini, A. & Walkter, B. D., 77-86 M Stockton Press) are illustrated in FIG. 4C. The control serum (-x) was from pMAMneoBlue vector immunized mice. The test sera (0) were from pM160 immunized mice.

Figure 4A:
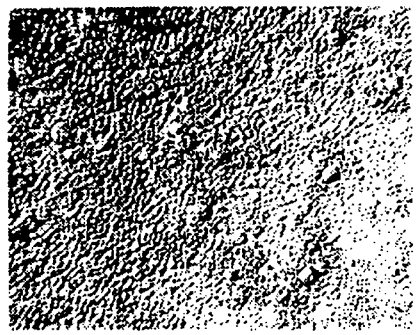
FIGS. 4A and 4B are photographs of MT-2 cells infected with $TCID_{50}HIV-1/III_B$ cell-free virus that was preincubated with serial dilutions of antisera.
Figure 4B:
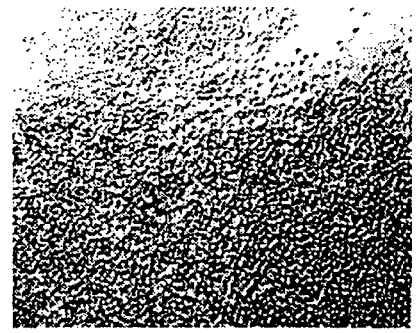
Figure 4C:
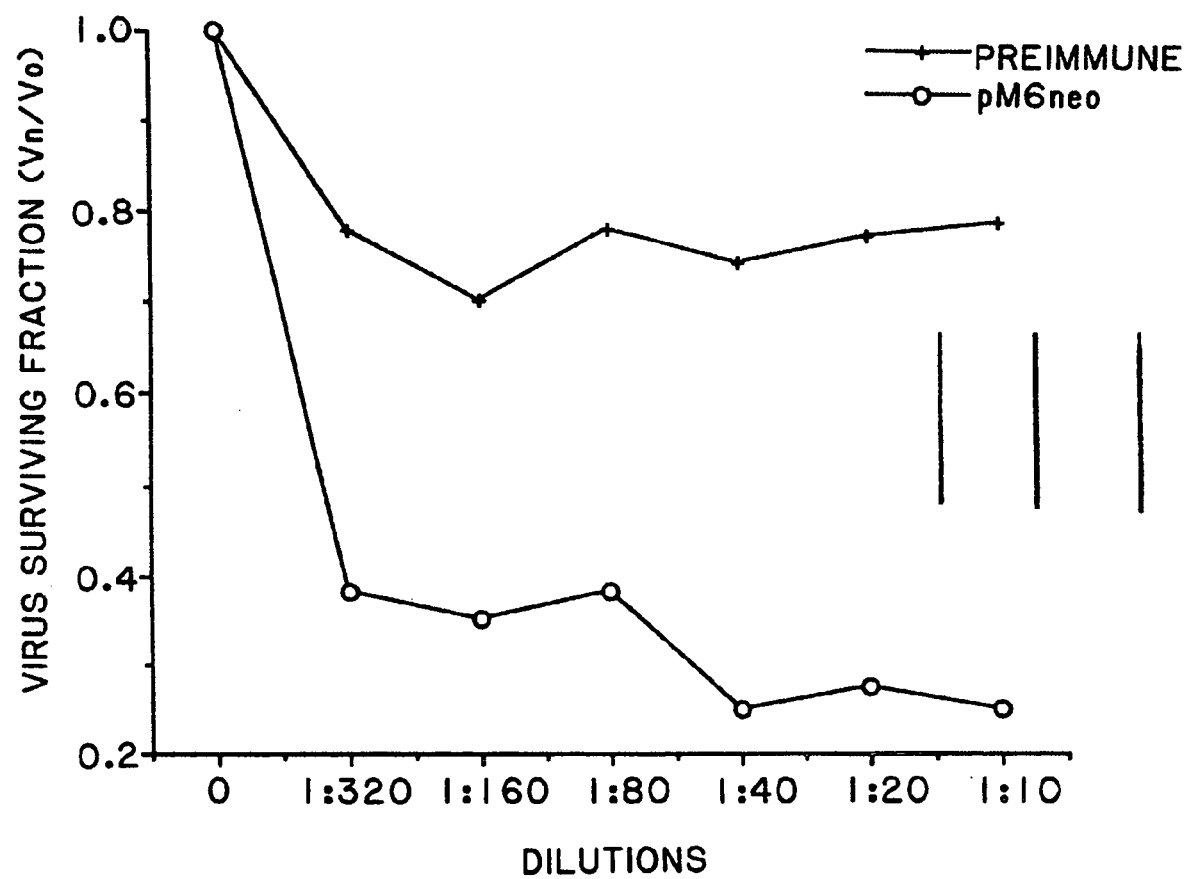
FIG. 4C is a graph illustrating the neutralization values $(V_n/V_o)$ versus the dilution factors from results using control serum (x=pMAMneoBlue vector-immunized mice) and test sera (O=pM160-immunized mice).
Figure 4D:
FIGS. 4D-4G are photographs of H9/$III_B$ cells used in experiments to examine syncytial inhibition using sera from immunized and control animals.
Figure 4E:
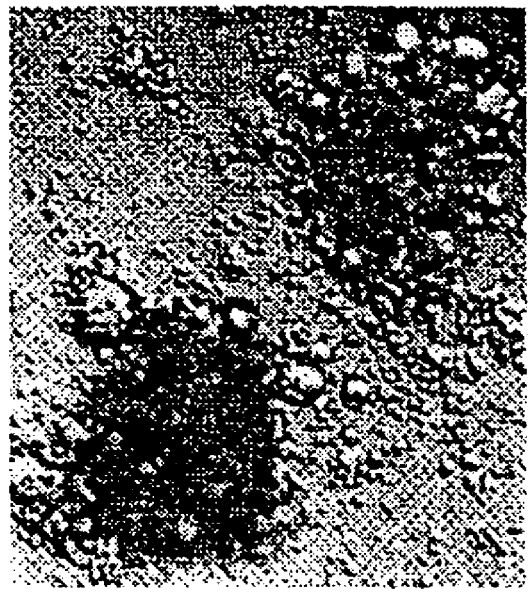
Figure 4F:
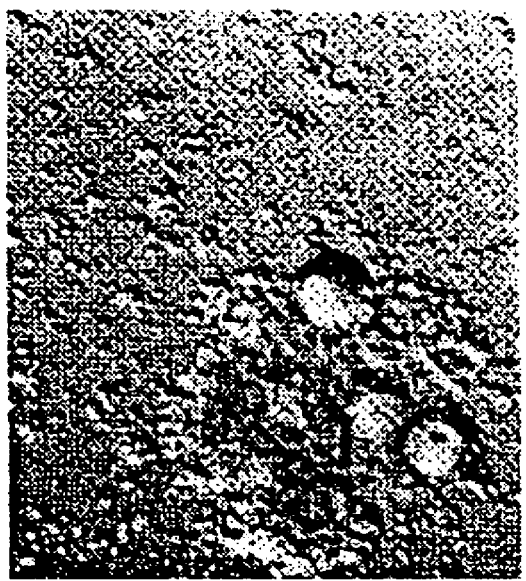
Figure 4G:
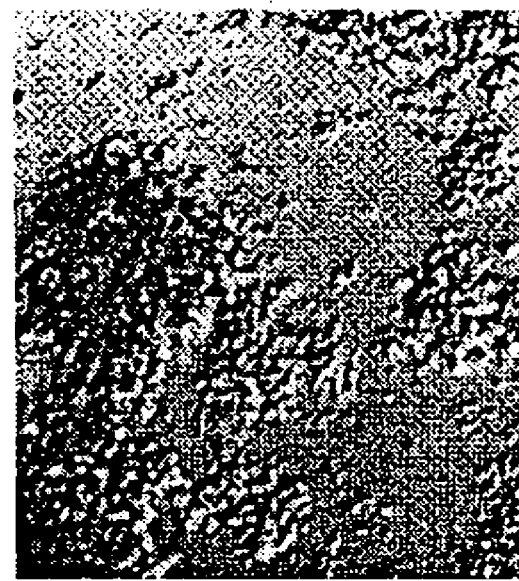
Figure 5:
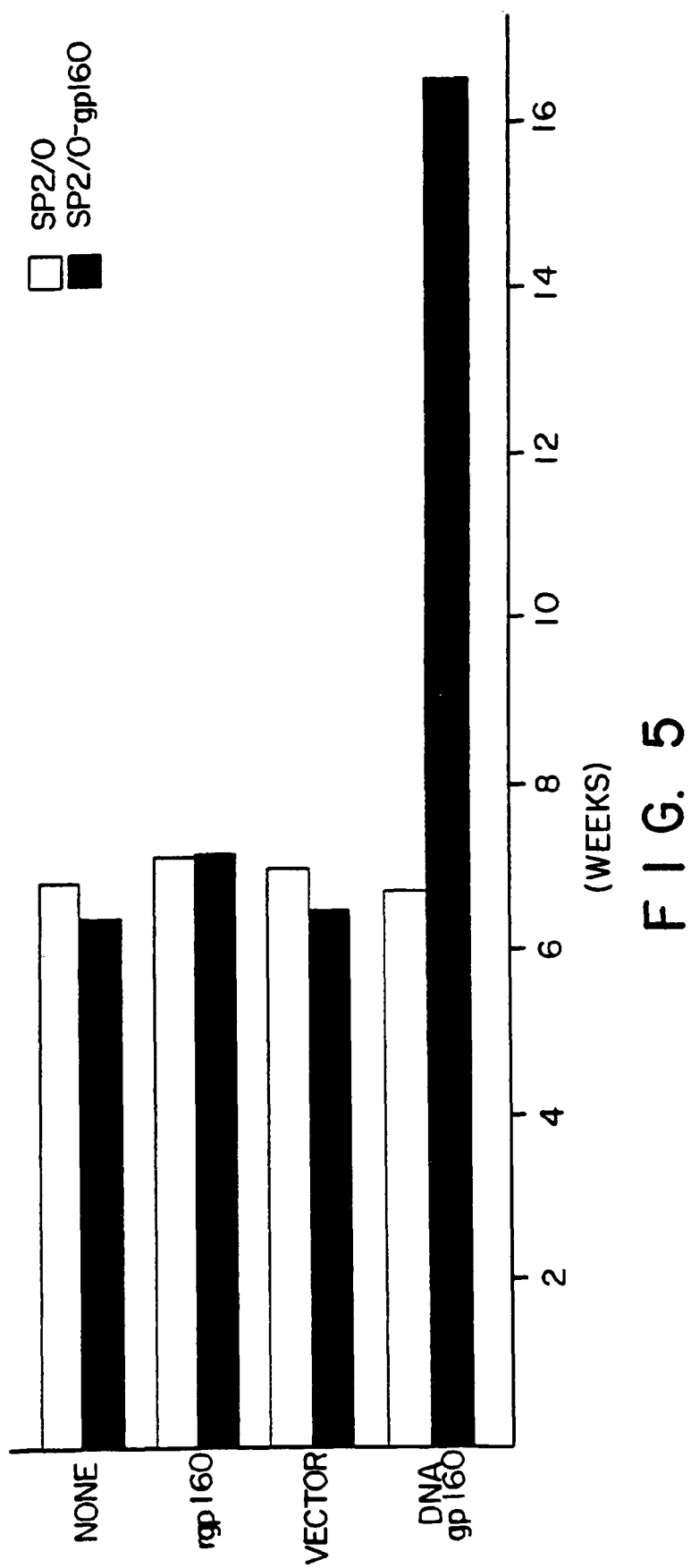
FIG. 5 is a chart depicting the survival of immunized and non-immunized mice challenged with HIV gp160-labelled and unlabelled tumor cells. Mice were immunized with recombinant gp160 protein, vector DNA only or recombinant vector comprising DNA encoding gp160. SP2/0 tumor cells or SP2/0-gp160 (SP2/0-cells transfected with DNA encoding gp160 and expressing gp160) tumor cells were introduced into the mice.
Figure 6:
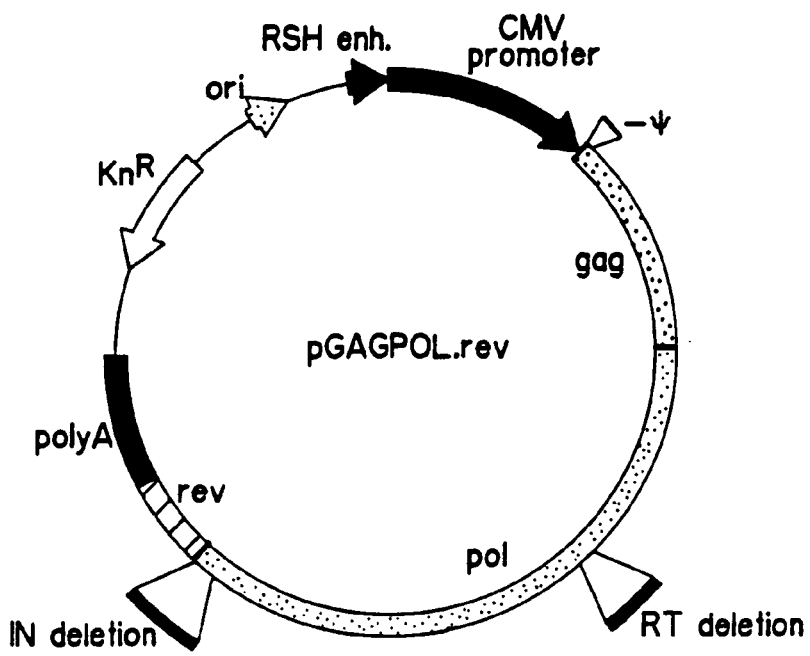
FIG. 6 is a plasmid map of pGAGPOL.rev.
Figure 7:
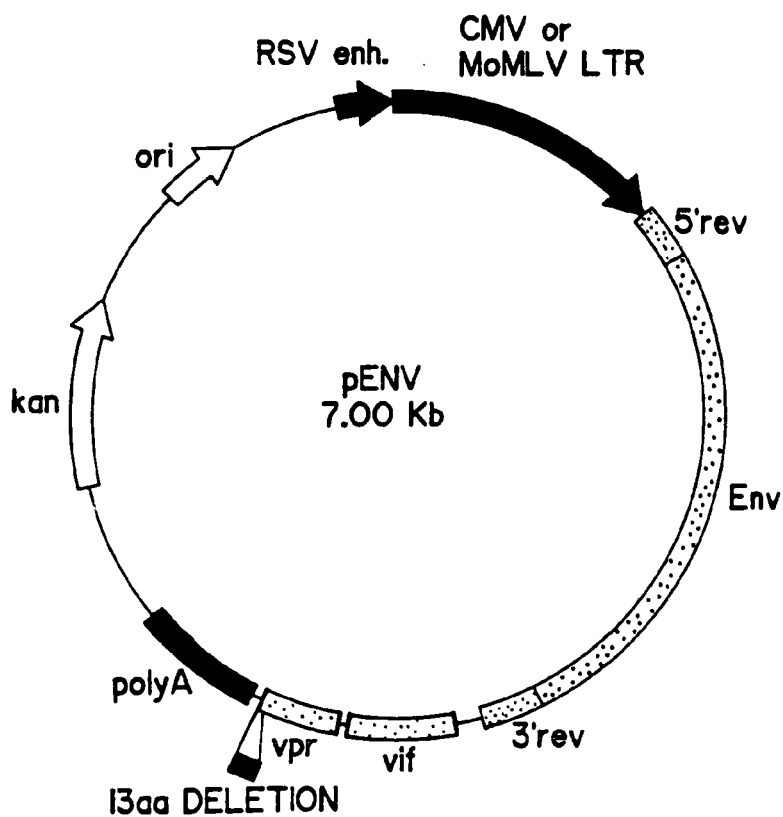
FIG. 7 is a plasmid map of pENV.
Figure 8A:
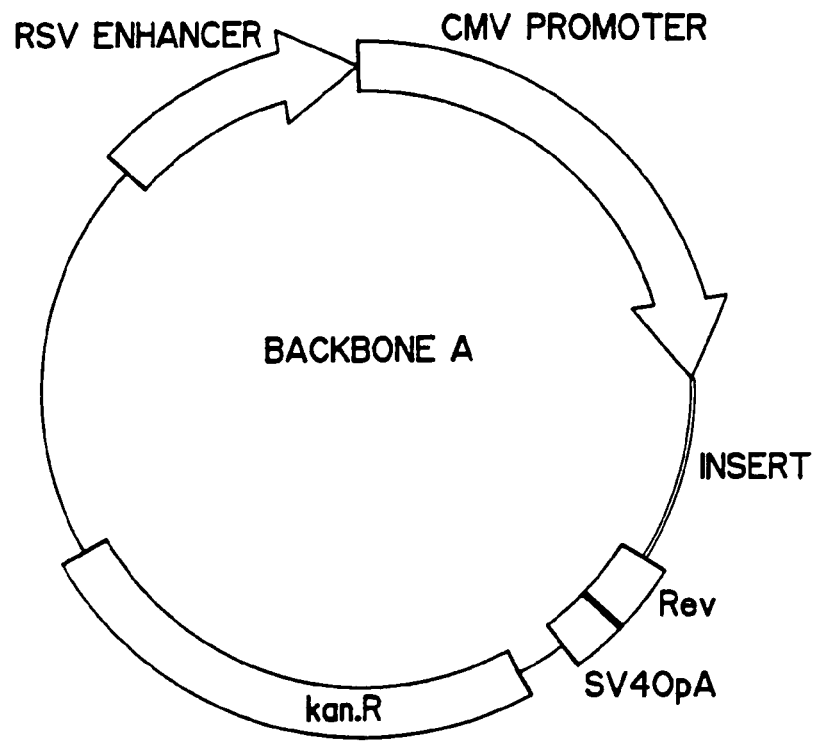
FIG. 8 is shows four backbones, A, B, C and D, used to prepare genetic construct.
Figure 8B:
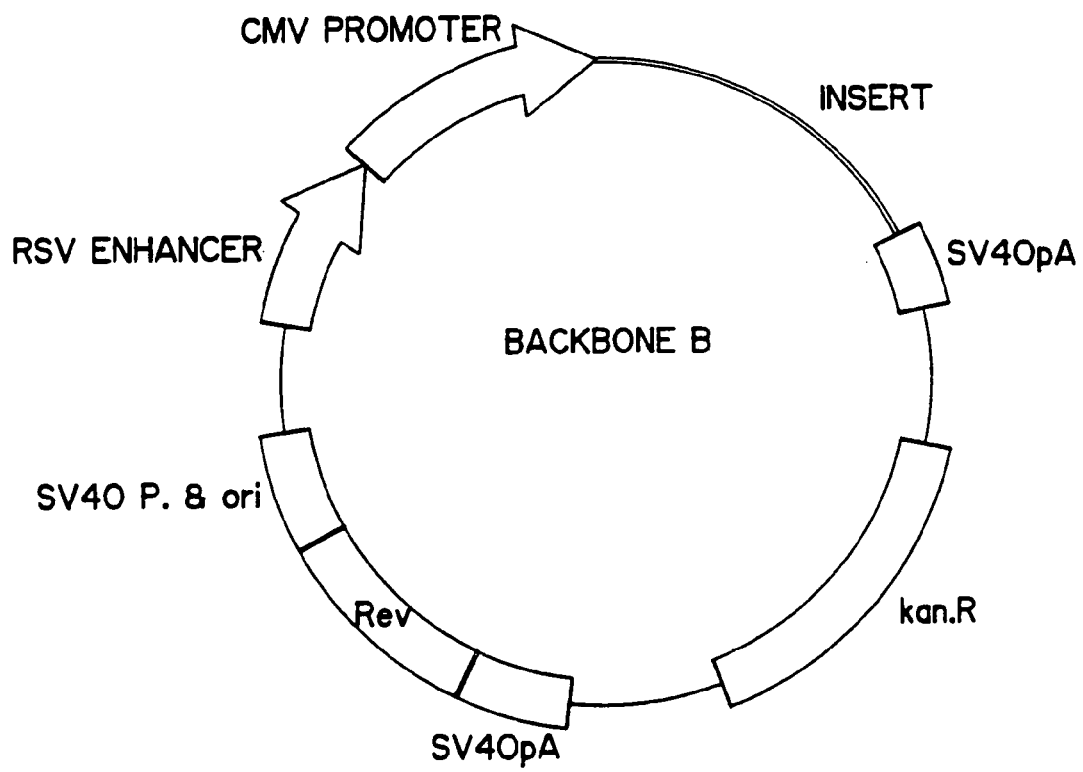
Figure 8C:
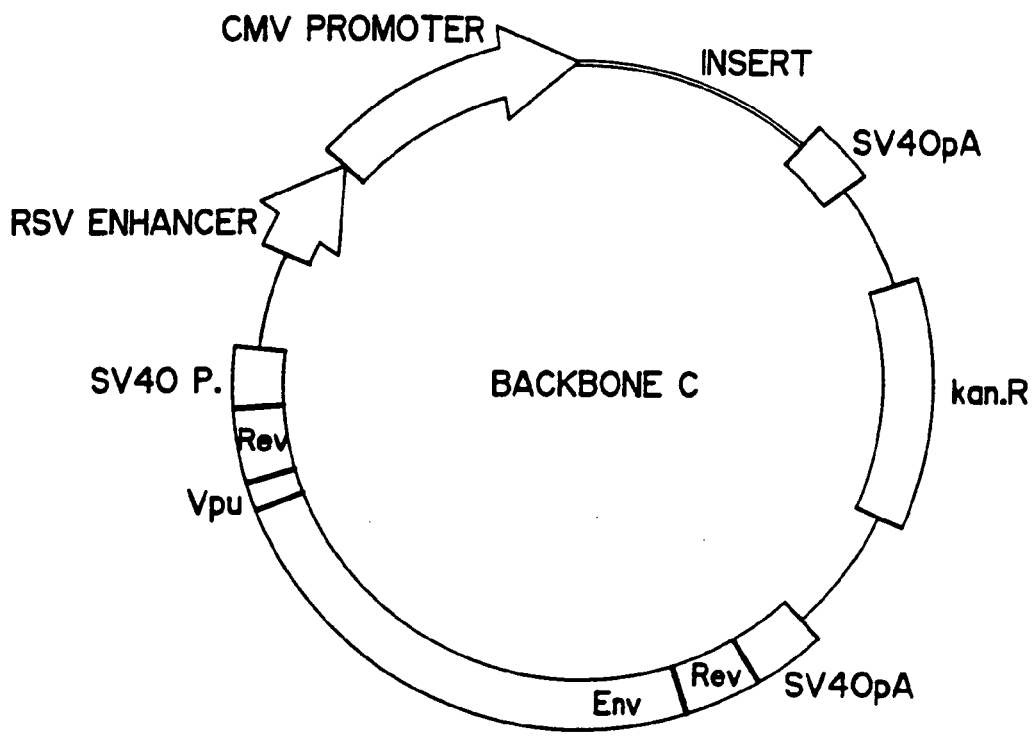
Figure 8D:
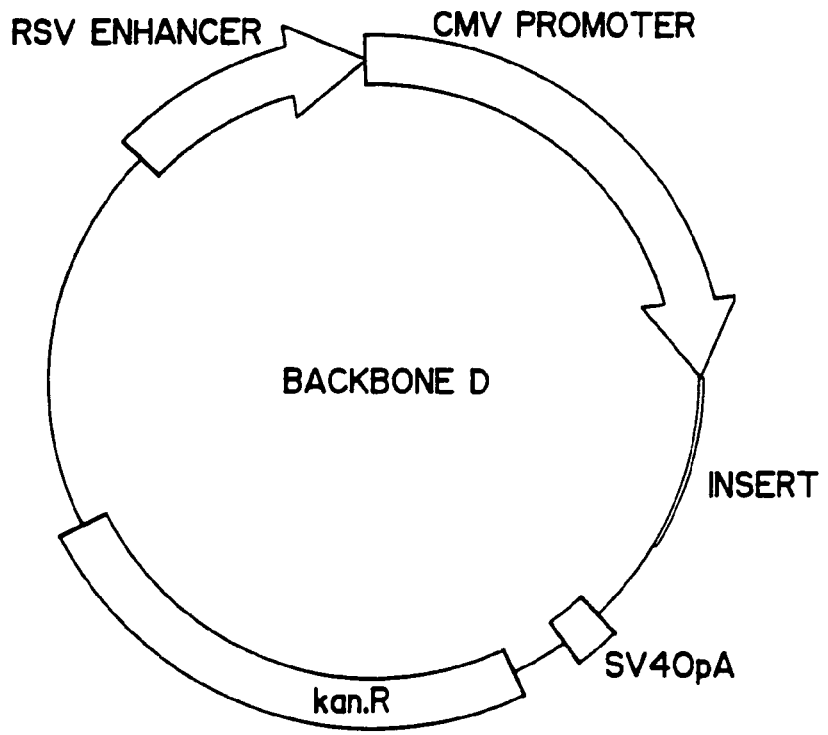
Figure 9:
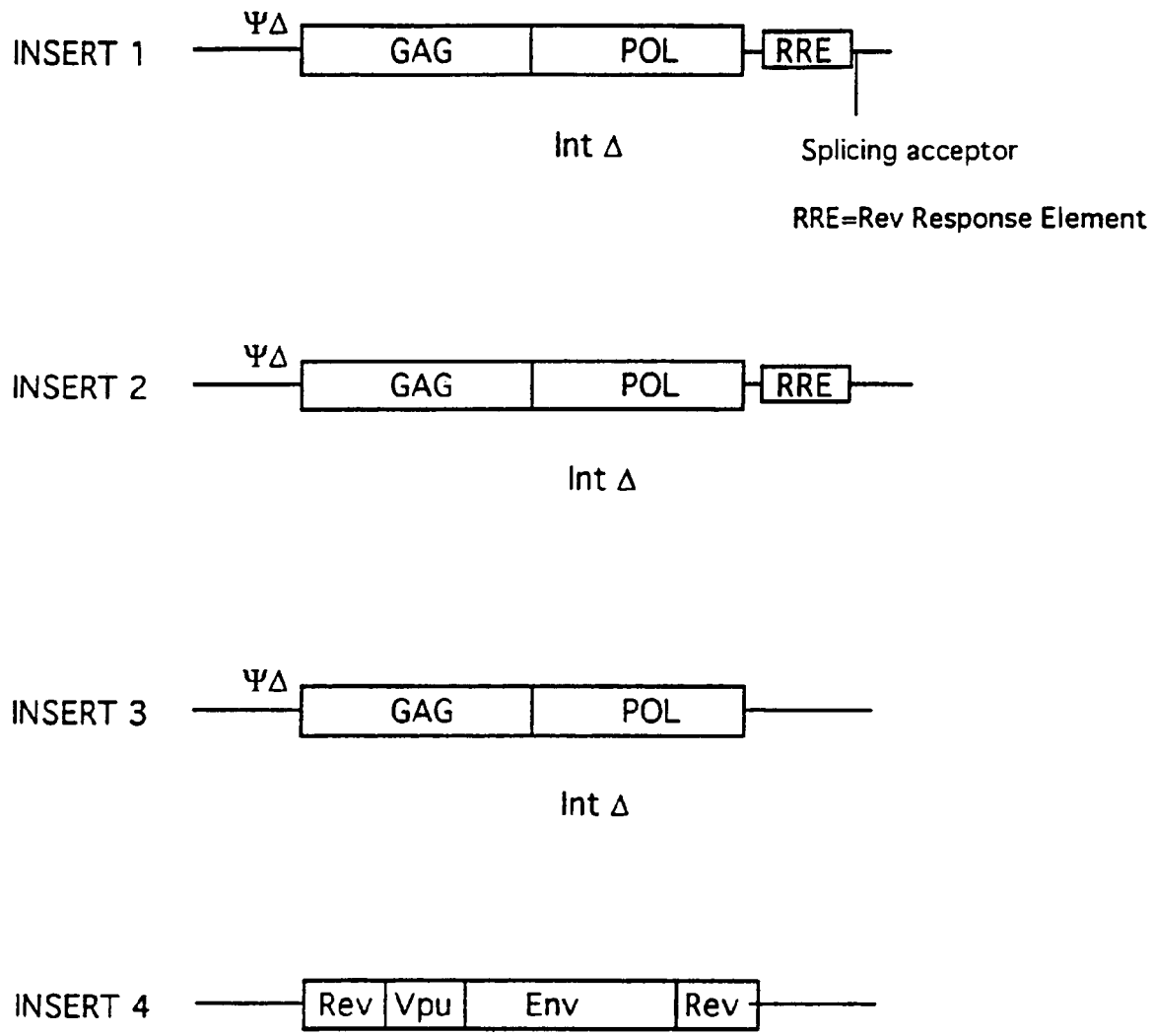
FIG. 9 shows four inserts, 1, 2, 3 and 4 which are inserted into backbones to produce genetic constructs.

Syncytia inhibition was performed as described by Osther, K., et al., (1991) *Hybridoma* 10:673-683. The H9/III$_B$ cell line was pre-incubated with serial dilutions (1:100, 1:200, and 1:400) of antisera were made in 96 well plates in a total volume of 50 µl for thirty minutes at 37° C. at 5% CO$_2$. Fusion was evaluated three days later quantitatively by visually counting the number of syncytia per well under a phase construct microscope. FIG. 4D is the target cells co-cultivated with HIV-1/III$_B$ cell line treated with preimmune serum. FIG. 4E is the same as FIG. 4D but treated with vector control immunized serum. FIG. 4F is the same as FIG. 4D but treated with rgp160 immunized serum. FIG. 4G is the same as FIG. 4D but treated with pM160 immunized serum. FIGS. 4D to 4G show that inhibition of syncytia was apparent at dilution at 1:200 in these assays. MT-2 cells were infected with cell-free HIV-1/III$_B$ which had been preincubated with vector-immunized antiserum readily formed syncytia (FIG. 4A). In comparison, preincubation with pM160 immunized mouse serum prevented syncytium formation (FIG. 4B). The neutralization kinetics were determined by $V_n/V_o$ versus serial dilutions of antisera (Nara, P., (1989) *Techniques In HIV Research, eds.* Aldovini, A. & Walker, B. D., 77-86, M Stockton Press) (FIG. 4C). The serum from the pM160 immunized mouse had biologically active neutralizing activity at dilutions of up to 1:320 while control antisera did not show similar activity.

To determine if the antiserum from the pM160 immunized mouse could inhibit envelope-mediated virus spread through direct cell-to-cell fusion, syncytium inhibition assays were performed. Antiserum from the pM160 immunized mouse inhibits HIV-1 induced syncytium formation at 1:200 dilutions (FIG. 4G). In contrast, the preimmune sera (FIG. 4D), antisera from the rgp160 immunized mice (FIG. 4F) and antisera from the control vector-immunized animals (FIG. 4E) failed to inhibit syncytium formation at the same dilutions.

Observations from the neutralization (FIGS. 4A-C) and syncytium inhibition assays (Figures D-G) of these sera correlates with the observed ELISA reactivities (FIG. 3). The antiserum from the pM160 immunized mouse which showed a high level of binding to neutralizing epitopes likewise demonstrated high level anti-viral activities; conversely, sera with little binding to these epitopes including the antiserum from rgp160 immunized mice have low anti-viral activity.

To test whether the antisera from pM160 immunized mice can inhibit gp120 binding to CD4-bearing T-cells, a direct inhibition assay monitored by fluorocytometry was employed (Chen, Y. H., et al., (1992) *AIDS* 6:533-539. It was observed that serum from the pM160 construct-immunized mouse was able to block the binding of gp120 to CD4-bearing T-cells: a 1:15 dilution of immune serum inhibited FITC-gp120 binding to CD4$^+$SupT1 cells by 22%±2% in replicate experiments as evaluated by flow cytometry. This indicates that this region for HIV entry into target cells can also be functionally inhibited by this antiserum. These data are consistent with observed ELISA reactivity of the antiserum to the CD4 binding site peptides (FIG. 3c).

Immunoglobulin isotyping studies were performed by using a commercial murine monoclonal antibody isotyping kit (Sigma). Of the anti-gp160 specific antibodies elicited by pM160 immunization, 19% are IgG1, 51% are IgG2, 16% are IgG3, 10% are IgM and 5% are IgA. The predominance of IgG isotypes indicates that a secondary immune response has taken place, and further suggests that helper T-cells can be elicited by genetic immunization.

pM160 and pMAMneoBlue DNAs were coated onto microtiter plates and specific binding was determined by ELISA using sera all immunized animals. No significant binding to plasmid DNA was observed. Thus, using genetic material for inoculation into muscle tissue appears unlikely to produce an anti-plasmid DNA response.

Introducing construct DNA into mouse muscle by needle injection may cause inconsistent results, as this technique does not provide a means to control DNA uptake by muscle cells. Injection of construct DNA alone (n≈4) with bupivacaine pretreated animals (n≈4) was compared. The immune responses observed in the two groups were dissimilar, with 25% and 75% animals responding in ELISA assays respectively. Increased efficiency may be achieved by use of a direct DNA delivery system such as particle bombardment (Klein, T. M. et al., (1992) *Bio/technology* 10:286-291.

Evidence of neutralization, syncytia inhibition, inhibition of CD4-gp120 binding, and specific binding to several important regions on the gp160 demonstrate that introduction of a DNA construct encoding HIV gp160 membrane-bound glycoprotein directly into muscle cells of living animals can elicit specific humoral responses, and generate biologically relevant anti-viral antibodies.

To test whether the vaccine is capable of eliciting a protective immune response, the animal model described above was used. Tumor cells were transfected with DNA encoding p160, confirmed to express the protein and implanted into the animal. Controls included untransfected tumor lines.

Genetically immunized animals were vaccinated with plasmid pm160. Controls included unvaccinated animals, animals vaccinated with vector DNA only and animals administered the gp160 protein.

Results demonstrate that the immune response of genetically vaccinated mice was sufficient to completely eliminate the transfected tumors while having no effect on untranslated tumors. gp160 protein vaccination led to some reduction in tumor size in transfected tumors as compared to untransfected tumors but had no effect on mortality. Unvaccinated animals showed similar mortality for both transfected and untransfected tumors.

Example 4

The following is a list of constructs which may be used in the methods of the present invention. The vector pBabe.puro, which is used as a starting material to produce many of the below listed constructs, was originally constructed and reported by Morgenstern, J. P. and H. Land, 1990 *Nucl. Acids Res.* 18(12):3587-3596, which is incorporated herein by reference. The pBabe.puro plasmid is particularly useful for expression of exogenous genes in mammalian cells. DNA sequences to be expressed are inserted at cloning sites under the control of the Moloney murine leukemia virus (Mo MuLV) long terminal repeat (LTR) promoter. The plasmid contains the selectable marker for puromycin resistance.

Example 5

Plasmid pBa.Vα3 is a 7.8 kb plasmid that contains a 2.7 kb EcoRI genomic fragment encoding the T cell receptor Vα3 region containing the L, V and J segments cloned into the EcoRI site of pBabe.puro. The T cell receptor-derived target protein is useful in the immunization against and treatment of T cell mediated autoimmune disease and clonotypic T cell lymphoma and leukemia.

Example 6

Plasmid pBa.gagpol-vpr is a 9.88 kb plasmid that contains the gag/pol and vif genes from HIV/MN cloned into pBabe.puro. The vpr gene is deleted. The plasmid which contains these HIV viral genes, which encode HIV target proteins, is useful in the immunization against and treatment of HIV infection and AIDS. The HIV DNA sequence is published in Reiz, M. S., 1992 *AIDS Res. Human Retro.* 8:1549, which is incorporated herein by reference. The sequence is accessible from Genbank No.: M17449, which is incorporated herein by reference.

Example 7

Plasmid pM160 is an 11.0 kb plasmid that contains the 2.3 kb PCR fragment encoding the HIV-I/3B envelope protein and rev/tat genes cloned into pMAMneoBlue. The nef region is deleted. The plasmid which contains these HIV viral genes, which encode HIV target proteins, is useful in the immunization against and treatment of HIV infection and AIDS. The DNA sequence of HIV-1/3B is published in Fisher, A., 1985 *Nature* 316:262, which is incorporated herein by reference. The sequence is accessible from Genbank No.: K03455, which is incorporated herein by reference.

Example 8

Plasmid pBa.VL is a 5.4 kb plasmid that contains PCR fragment encoding the VL region of an anti-DNA antibody cloned into pBabe.puro at the XbaI and EcoRI sites. The antibody-derived target protein is an example of a target protein useful in the immunization against and treatment of B cell mediated autoimmune disease and clonotypic B cell lymphoma and leukemia. A general method for cloning functional variable regions from antibodies can be found in Chaudhary, V. K., et al., 1990 *Proc. Natl. Acad. Sci. USA* 87:1066, which is incorporated herein by reference.

Example 9

Plasmid pOspA.B is a 6.84 kb plasmid which contains the coding regions encoding the OspA and OspB antigens of the *Borrelia burgdorferi*, the spirochete responsible for Lyme's disease cloned into pBabe.puro at the BamHI and SalI sites. The PCR primers used to generate the OspA and OspB fragments are 5'-GAAGGATCCATGAAAAAATATTTAT-TGGG-3' (SEQ ID NO:3) and 5'-ACTGTCGACTTATTT-TAAAGCGTTTTTAAG-3' (SEQ ID NO: 4). See: Williams, W. V., et al. 1992 *DNA and Cell. Biol.* 11(3):207, which is incorporated herein by reference. The plasmid which contains these pathogen genes, which encode target proteins, is useful in the immunization against Lyme's disease.

Example 10

Plasmid pBa.Rb-G is a 7.10 kb plasmid which contains a PCR generated fragment encoding the rabies G protein cloned into pBabe.puro at the BamHI site. The plasmid which contains this pathogen gene, which encodes the rabies G protein, is useful in the immunization against Rabies. The DNA sequence is disclosed in Genebank No.: M32751, which is incorporated herein by reference. See also: Anilionis, A., et al., 1981 *Nature* 294:275, which is incorporated herein by reference.

Example 11

Plasmid pBa.HPV-L1 is a 6.80 kb plasmid which contains a PCR generated fragment encoding the L1 capsid protein of the human papillomavirus (HPV) including HPV strains 16, 18, 31 and 33 cloned into pBabe.puro at the BamHI and EcoRI sites. The plasmid is useful in the immunization against HPV infection and the cancer caused thereby. The DNA sequence is disclosed in Genebank No.: M15781, which is incorporated herein by reference. See also: Howley, P., 1990 *Fields Virology*, Volume 2, Eds.: Channock, R. M. et al. Chapter 58:1625; and Shah, K. and P. Howley, 1990 *Fields Virology*, Volume 2, Eds.: Channock, R. M. et al. Chapter 59; both of which are incorporated herein by reference.

Example 12

Plasmid pBa.HPV-L2 is a 6.80 kb plasmid which contains a PCR generated fragment encoding the L2 capsid protein of the human papillomavirus (HPV) including HPV strains 16, 18, 31 and 33 cloned into pBabe.puro at the BamHI and EcoRI sites. The plasmid is useful in the immunization against HPV infection and the cancer caused thereby. The DNA sequence is disclosed in Genebank No.: M15781, which is incorporated herein by reference. See also: Howley, P., 1990 *Fields Virology*, Volume 2, Eds.: Channock, R. M. et al. Chapter 58:1625; and Shah, K. and P. Howley, 1990 *Fields Virology*, Volume 2, Eds.: Channock, R. M. et al. Chapter 59; both of which are incorporated herein by reference.

Example 13

Plasmid pBa.MNp7 is a 5.24 kb plasmid which contains a PCR generated fragment encoding the p7 coding region including the HIV MN gag (core protein) sequence cloned into pBabe.puro at the BamHI site. The plasmid which contains these HIV viral genes, which encode HIV target proteins, is useful in the immunization against and treatment of HIV infection and AIDS. Reiz, M. S., 1992 *AIDS Res. Human Retro.* 8:1549, which is incorporated herein by reference. The sequence is accessible from Genbank No.: M17449, which is incorporated herein by reference.

Example 14

Plasmid pGA733-2 is a 6.3 kb plasmid that contains the GA733-2 tumor surface antigen cloned from the colorectal carcinoma cell line SW948 into pCDM8 vector (Seed, B. and A. Aruffo, 1987 *Proc. Natl. Acad. Sci. USA* 84:3365, which is incorporated herein by reference) at BstXI site. The tumor-associated target protein is an example of a target protein useful in the immunization against and treatment of hyperproliferative disease such as cancer. The GA733-2 antigen is a useful target antigen against colon cancer. The GA733 antigen is reported in Szala, S. et al., 1990 *Proc. Natl. Acad. Sci. USA* 87:3542-3546, which is incorporated herein by reference.

Example 15

Plasmid pT4-pMV7 is a 11.15 kb plasmid that contains cDNA which encodes human CD4 receptor cloned into pMV7 vector at the EcoRI site. The CD4 target protein is useful in the immunization against and treatment of T cell lymphoma. Plasmid pT4-pMV7 is available from the AIDS Repository, Catalog No. 158.

Example 16

Plasmid pDJGA733 is a 5.1 kb plasmid that contains the GA733 tumor surface antigen cloned into pBabe.puro at the BamHI site. The tumor-associated target protein is an example of a target protein useful in the immunization against and treatment of hyperproliferative disease such as cancer. The GA733 antigen is a useful target antigen against colon cancer.

Example 17

Plasmid pBa.RAS is a 6.8 kb plasmid that contains the ras coding region that was first subcloned from pZIPneoRAS and cloned into pBabe.puro at the BamHI site. The ras target protein is an example of a cytoplasmic signalling molecule. The method of cloning ras is reported in Weinberg 1984 *Mol. Cell. Biol.* 4:1577, which is incorporated herein by reference. Ras encoding plasmid are useful for the immunization against and treatment of hyperproliferative disease such as cancer; in particular, ras related cancer such as bladder, muscle, lung, brain and bone cancer.

Example 18

Plasmid pBa.MNp55 is a 6.38 kb plasmid which contains a PCR generated fragment encoding the p55 coding region including the HIV MN gag precursor (core protein) sequence cloned into pBabe.puro at the BamHI site. The plasmid which contains these HIV viral genes, which encode HIV target proteins, is useful in the immunization against and treatment of HIV infection and AIDS. Reiz, M. S., 1992 *AIDS Res. Human Retro.* 8:1549, which is incorporated herein by reference. The sequence is accessible from Genbank No.: M17449, which is incorporated herein by reference.

Example 19

Plasmid pBa.MNp24 is a 5.78 kb plasmid which contains a PCR generated fragment from the pMN-SF1 template encoding the p24 coding region including the whole HIV MN gag coding region cloned into pBabe.puro at the BamHI and EcoRI sites. The plasmid which contains these HIV viral genes, which encode HIV target proteins, is useful in the immunization against and treatment of HIV infection and AIDS. Reiz, M. S., 1992 *AIDS Res. Human Retro.* 8:1549, which is incorporated herein by reference. The sequence is accessible from Genbank No.: M17449, which is incorporated herein by reference.

Example 20

Plasmid pBa.MNp17 is a 5.5 kb plasmid which contains a PCR generated fragment encoding the p17 coding region including the HIV MN gag (core protein) sequence cloned into pBabe.puro at the BamHI and EcoRI sites. The plasmid which contains these HIV viral genes, which encode HIV target proteins, is useful in the immunization against and treatment of HIV infection and AIDS. Reiz, M. S., 1992 *AIDS Res. Human Retro.* 8:1549, which is incorporated herein by reference. The sequence is accessible from Genbank No.: M17449, which is incorporated herein by reference.

Example 21

Plasmid pBa.SIVenv is a 7.8 kb plasmid which contains a 2.71 PCR generated fragment amplified from a construct containing SIV 239 in pBR322 cloned into pBabe.puro at the BamHI and EcoRI sites. The primers used are 5'-GC-CAGTTTTGGATCCTTAAAAAAGGCTTGG-3' (SEQ ID NO:5) and 5'-TTGTGAGGGACAGAATTCCAATCAGGG-3' (SEQ ID NO:6). The plasmid is available from the AIDS Research and Reference Reagent Program; Catalog No. 210.

Example 22

Plasmid pcTSP/ATK.env is a 8.92 kb plasmid which contains a PCR generated fragment encoding the complete HTLV envelope coding region from HTLV-1/TSP and/ATK isolates subcloned into the pcDNA1/neo vector. The primers used are 5'-CAGTGATATCCCGGGAGACTCCTC-3' (SEQ ID NO:7) and 5'-GAATAGAAGAACTCCTCTAGAATTC-3' (SEQ ID NO:8). Plasmid pcTSP/ATK.env is reported in 1988 *Proc. Natl. Acad. Sci. USA* 85:3599, which is incorporated herein by reference. The HTLV env target protein is useful in the immunization against and treatment of infection by HTLV and T cell lymphoma.

Example 23

Plasmid pBa.MNgp160 is a 7.9 kb plasmid which contains a 2.8 kb PCR generated fragment amplified from a construct containing MNenv in pSP72 and cloned into pBabe.puro at the BamHI and EcoRI sites. The primers used are 5'-GCCT-TAGGCGGATCCTATGGCAGGAAG-3' (SEQ ID NO:9) and 5'-TAAGATGGGTGGCCATGGTGAATT-3' (SEQ ID NO:10). Reiz, M. S., 1992 *AIDS Res. Human Retro.* 8:1549, which is incorporated herein by reference. The sequence is accessible from Genbank No.:M17449, which is incorporated herein by reference. The plasmid which contains these HIV viral genes, which encode HIV target proteins, is useful in the immunization against and treatment of HIV infection and AIDS.

Example 24

Plasmid pC.MNp55 is a 11.8 kb plasmid which contains a 1.4 kb PCR generated fragment amplified from the gag region of MN isolate and cloned into the pCEP4 vector. The plasmid which contains these HIV viral genes, which encode HIV target proteins, is useful in the immunization against and treatment of HIV infection and AIDS. Reiz, M. S., 1992 *AIDS Res. Human Retro.* 8:1549, which is incorporated herein by reference. The sequence is accessible from Genbank No.: M17449, which is incorporated herein by reference.

Example 25

Plasmid pC.Neu is a 14.2 kb plasmid that contains a 3.8 kb DNA fragment containing the human neu oncogene coding region that was cut out from the LTR-2/erbB-2 construct and subcloned into the pCEP4 vector. The pC.Neu plasmid is reported in DiFiore 1987 *Science* 237:178, which is incorporated herein by reference. The neu oncogene target protein is an example of a growth factor receptor useful as a target protein for the immunization against and treatment of hyperproliferative disease such as cancer; in particular, colon, breast, lung and brain cancer.

Example 26

Plasmid pC.RAS is a 11.7 kb plasmid that contains a 1.4 kb DNA fragment containing the ras oncogene coding region that was first subcloned from pZIPneoRAS and subcloned into pCEP4 at the BamHI site. The pC.RAS plasmid is reported in Weinberg 1984 *Mol. Cell. Biol.* 4:1577, which is incorporated herein by reference. The ras target protein is an example of a cytoplasmic signalling molecule. Ras encoding plasmid are useful for the immunization against and treatment of hyperproliferative disease such as cancer; in particular, ras related cancer such as bladder, muscle, lung, brain and bone cancer.

Example 27

Plasmid pNLpuro is a 15 kb plasmid which contains HIV gag/pol and SV40-puro insertion. The plasmid which contains these HIV viral genes which encode HIV target proteins, is useful in the immunization against and treatment of HIV infection and AIDS.

Example 28

A DNA construct was designed to test the effectiveness of a genetic vaccine against human CD4 in mice. These experiments were designed to test the ability of a vaccine to protect against a T lymphoma antigen. In T cell lymphoma, CD4 is a tumor specific antigen. Accordingly, this model demonstrates the ability of the genetic vaccine to protect against T lymphoma. Further, these experiments tested the effectiveness against a member of the immunoglobulin superfamily of molecules. CD4 is highly conserved between human and murine species.

The animal model used was described above. Tumor cells were transfected with DNA encoding CD4, confirmed to express the protein and implanted into the animal. Controls included untransfected tumor lines. Although the animals were immunocompetent, an immune response was not directed against the implanted, CD4-labelled tumors in unvaccinated animals.

Genetically immunized animals were vaccinated with plasmid pT4-pMV7, described in Example 15. Controls included unvaccinated animals and animals administered the CD4 protein.

In the genetic immunization procedure described herein, the quadriceps muscles of BALB/c mice were injected with 100 µg of 0.5% bupivacaine-HCl and 0.1% methylparaben in isotonic NaCl using a 27-gauge needle to stimulate muscle cell regeneration to facilitate uptake of the genetic construct. Twenty-four hours later, the same injection sites were then injected with either 100 µg of pT4-pMV7 or with 100 µg of pMV7 as a control plasmid. The mice were boosted by injecting the same amount of DNA construct three times at two week intervals in the same manner but without pre-treatment with bupivacaine-HCl.

Animals received 1,000,000 CD4-labelled tumor cells. In non-vaccinated animals, large tumors formed and death resulted after about 7-10 weeks. Vaccinated animals did not develop similar deadly tumors.

Results demonstrate that the immune response of genetically vaccinated mice was sufficient to completely eliminate the transfected tumors while having no effect on untransfected tumors. CD4 protein vaccination led to some reduction in tumor size in transfected tumors as compared to untransfected tumors but had no effect on mortality. Unvaccinated animals showed similar mortality for both transfected and untransfected tumors.

Example 29

A DNA construct was designed to test the effectiveness of a genetic vaccine against human GA733 in mice. These experiments were designed to test the ability of a vaccine to protect against GA733 associated cancer such as colon cancer. The animal model used was described above. Tumor cells were transfected with DNA encoding GA733, confirmed to express the protein and implanted into the animal. Controls included untransfected tumor lines.

Genetically immunized animals were vaccinated with plasmid pGA733-2, described in Example 14, following the method described above. Controls included unvaccinated animals and animals administered the GA733 protein.

Results demonstrate that the immune response of genetically vaccinated mice was sufficient to completely eliminate the transfected tumors while having no effect on untranslated tumors. GA733 protein vaccination led to some reduction in tumor size in transfected tumors as compared to untransfected tumors but had no effect on mortality. Unvaccinated animals showed similar mortality for both transfected and untransfected tumors.

Example 30

A DNA construct was designed to test the effectiveness of a genetic vaccine against human p185neu in mice. These experiments were designed to test the ability of a vaccine to protect against p185neu associated cancer such as breast, lung and brain cancer. The animal model used was described above. Tumor cells were transfected with DNA encoding neu, confirmed to express the protein and implanted into the animal. Controls included untransfected tumor lines.

Genetically immunized animals were vaccinated with plasmid pLTR-2/erbB-2, a 14.3 kb plasmid that contains the human neu oncogene coding region cloned into the LTR-2 vector at the XhoI site following the method described above. The 5'LTR and 3'LTR are from Moloney-MuLV LTR. Controls included unvaccinated animals and animals administered the p185neu protein.

Results demonstrate that the immune response of genetically vaccinated mice was sufficient to completely eliminate the transfected tumors while having no effect on untranslated tumors. p185 protein vaccination led to some reduction in tumor size in transfected tumors as compared to untransfected tumors but had no effect on mortality. Unvaccinated animals showed similar mortality for both transfected and untransfected tumors.

Example 31

A DNA construct was designed to test the effectiveness of a genetic vaccine against human Ras in mice. These experiments were designed to test the ability of a vaccine to protect against Ras associated cancer such as bladder, muscle, lung, brain and bone cancer. The animal model used was described above. Tumor cells were transfected with DNA encoding Ras, confirmed to express the protein and implanted into the animal. Controls included untransfected tumor lines.

Genetically immunized animals were vaccinated with plasmid pBa.RAS, described in Example 17 following the vaccination method described above. The ras target protein is an example of a cytoplasmic signalling molecule. The method of cloning ras is reported in Weinberg 1984 *Mol. Cell. Biol.* 4:1577, which is incorporated herein by reference. Controls included unvaccinated animals and animals administered the Ras protein.

Example 32

A DNA construct was designed to test the effectiveness of a genetic vaccine against human rabies G protein antigen in mice. The animal model used was described above. Tumor cells were transfected with DNA encoding rabies G protein, confirmed to express the protein and implanted into the animal. Controls included untransfected tumor lines.

Genetically immunized animals were vaccinated with plasmid pBa.Rb-G which is described in Example 10, following the vaccination method described above. The rabies G target protein is an example of a pathogen antigen. The DNA sequence is disclosed in Genebank No.: M32751. Controls included unvaccinated animals and animals administered the G protein.

Example 33

A DNA construct was designed to test the effectiveness of a genetic vaccine against Lyme's disease antigen in mice. The animal model used was described above. Tumor cells were transfected with DNA encoding OspA and Osp B, confirmed to express the protein and implanted into the animal. Controls included untransfected tumor lines.

Genetically immunized animals were vaccinated with plasmid pOspA.B which is described in Example 9. Controls included unvaccinated animals and animals administered OspA and OspB proteins.

Example 34

A DNA construct was designed to test the effectiveness of a genetic vaccine against a human T cell receptor variable region in mice. These experiments were designed to test the ability of a vaccine to protect against a T cell receptor derived protein associated cancer such as T cell lymphoma and T cell mediated autoimmune disease. The animal model used was described above. Tumor cells were transfected with DNA encoding Ras, confirmed to express the protein and implanted into the animal. Controls included untransfected tumor lines.

Genetically immunized animals were vaccinated with plasmid pBa.Vα3 which is described in Example 5 following the vaccination method described above.

Example 35

The plasmid pM160 can be used as a starting material for several plasmids useful to express one or more genes from the env portion of HIV. Construction os pM160 is described above. The plasmid encompasses gp160, tat and rev coding region. The net gene is absent.

The promoter controlling gp160/rev/tat gene expression is MMTV LTR. The promoter may be deleted and replaced with Actin promoter, myosin promoter, HIV LTR promoter and CMV promoter.

The gene conferring ampicillin resistance may be deleted or otherwise inactivated. The gene conferring neomycin resistance may be placed under the control of a bacterial promoter.

The Rous sarcoma virus enhancer may be deleted from the plasmid. The RSV enhancer may be replaced with the muscle creatine enhancer.

The gp160/rev/tat genes overlap and share the same nucleotide sequences in different reading frames. The rev gene may be deleted by changing its initiation codon to a different codon. Similarly, the tat gene may be eliminated by the same means. In each plasmid except those using the HIV LTR promoter to control gp160/rev/tat, either rev, tat, or both rev and tat may be eliminated. In plasmids using the HIV LTR promoter, tat must be present.

The following Table lists pM160-modified plasmids. Each plasmid has an inactivated ampicillin gene. Each has deleted the RSV enhancer. Some have no enhancer (no); some have creatine muscle enhancer (CME). Some have the HIV rev gene (yes) while it is deleted in others (no). Some have the HIV tat gene (yes) while it is deleted in others (no).

| Construct | Promoter | enhancer | rev | tat |
|---|---|---|---|---|
| RA-1 | Actin | no | yes | yes |
| RA-2 | Actin | no | yes | no |
| RA-3 | Actin | no | no | yes |
| RA-4 | Actin | CME | yes | yes |
| RA-5 | Actin | CME | yes | no |
| RA-6 | Actin | CME | no | yes |
| RA-7 | CMV | no | yes | yes |
| RA-8 | CMV | no | yes | no |
| RA-9 | CMV | no | no | yes |
| RA-10 | CMV | CME | yes | yes |
| RA-11 | CMV | CME | yes | no |
| RA-12 | CMV | CME | no | yes |
| RA-13 | MMTV | no | yes | yes |
| RA-14 | MMTV | no | yes | no |
| RA-15 | MMTV | no | no | yes |
| RA-16 | MMTV | CME | yes | yes |
| RA-17 | MMTV | CME | yes | no |
| RA-18 | MMTV | CME | no | yes |
| RA-19 | Myosin | no | yes | yes |
| RA-20 | Myosin | no | yes | no |
| RA-21 | Myosin | no | no | yes |
| RA-22 | Myosin | CME | yes | yes |
| RA-23 | Myosin | CME | yes | no |
| RA-24 | Myosin | CME | no | yes |
| RA-25 | HIV-1 LTR | no | yes | yes |
| RA-26 | HIV-1 LTR | no | no | yes |
| RA-27 | HIV-1 LTR | CME | yes | yes |
| RA-28 | HIV-1 LTR | LTRCME | no | yes |

Constructions RA-29 to RA-56 are identical to RA-1 to RA-32 respectively except in each case the promoter controlling the neomycin gene is a bacterial promoter.

Example 36

The plasmid pNLpuro may be used as a starting material to produce several different plasmids which express the HIV gag/pol genes. As described above, pNLpuro was constructed for expression of gag pol. The plasmid pNLpuroΔvpr, which is described above, was designed to delete the vpr regulatory gene from the HIV gag pol vector in order to eliminate a necessary regulatory protein from the set of genes to be introduced by vaccination. In addition to vpr, other changes may be made by those having ordinary skill in the art to plasmid pNL43puro using standard molecular biology techniques and widely available starting material.

The human flanking sequences 5' and 3' of the HIV sequences can be removed by several methods. For example, using PCR, only HIV, SV40-puro, and pUC18 sequences can be amplified and reconstructed.

The psi region of HIV, which is important in the packaging of the virus, can be deleted from pNL43puro-based plasmids. In order to delete the psi region, the pNLpuro plasmid is cut with SacI and SpeI. This digestion removes the psi region as well as the 5' LTR which is upstream and portion of the gag/pol region which is downstream of psi. In order to reinsert the deleted non-psi sequences, PCR amplification is performed to regenerate those sequences. Primers are designed which regenerate the portions of the HIV sequence 5' and 3' to psi without regenerating psi. The primers reform the SacI site at the portion of the plasmid 5' of the 5' LTR. Primers go downstream from a site upstream of the SacI site to a site just 3' of the 5' end of the psi region, generating an AatI site at the 3' end. Primers starting just 5' of the psi region also generate an AatI site and, starting 3' of the SpeI site, regenerate that site. The PCR generated fragments are digested with SacI, AatI and SpeI and ligated together with the SacI/SpeI digested pNLpuro-psi fragment. The HIV 5'LTR promoter can be deleted and replaced with Moloney virus promoter, MMTV LTR, Actin promoter, myosin promoter and CMV promoter.

The HIV 3'LTR polyadenylation site can be deleted and replaced with SV40 polyadenylation site.

The gene conferring ampicillin resistance may be deleted or otherwise inactivated.

The following is a list of pNLpuro-based constructions in which HIV psi and vpr regions are deleted and human flanking regions 5' and 3' of the HIV sequences are deleted.

| Construct | Promoter | poly(A) | Amp$^r$ |
|---|---|---|---|
| LA-1 | Moloney | HIV 3'LTR | yes |
| LA-2 | Moloney | SV40 | yes |
| LA-3 | Moloney | HIV 3'LTR | no |
| LA-4 | Moloney | SV40 | no |
| LA-5 | CMV | HIV 3'LTR | yes |
| LA-6 | CMV | SV40 | yes |
| LA-7 | CMV | HIV 3'LTR | no |
| LA-8 | CMV | SV40 | no |
| LA-9 | MMTV | HIV 3'LTR | yes |
| LA-10 | MMTV | SV40 | yes |
| LA-11 | MMTV | HIV 3'LTR | no |
| LA-12 | MMTV | SV40 | no |
| LA-13 | HIV 5' LTR | HIV 3'LTR | yes |
| LA-14 | HIV 5' LTR | SV40 | yes |
| LA-15 | HIV 5' LTR | HIV 3'LTR | no |
| LA-16 | HIV 5' LTR | SV40 | no |

Constructions LA-17 to LA-32 are identical to LA-1 to LA-16 respectively except in each case at least one of the human flanking sequence remains.

Example 37

In another construction for expressing the env gene, that region of HIV may be inserted into the commercially available plasmid pCEP4 (Invitrogen). The pCEP4 plasmid is particularly useful since it contains the Epstein Barr virus origin of replication and nuclear antigen EBNA-1 coding region which produces high copy episomal replication without integration. pCEP4 also contains the hygromycin marker under the regulatory control of the thymidine kinase promoter and polyadenylation site. The HIV env coding region is placed under the regulatory control of the CMV promoter and SV40 polyadenylation site. The HIV env coding region was obtained as a 2.3 kb PCR fragment form HIV/3B, Genebank sequence K03455. The resulting pCEP4-based plasmid, pRA-100, is maintained extrachromosomally and produces gp160 protein.

Example 38

In another construction for expressing the env gene, that region of HIV may be inserted into the commercially available plasmid pREP4 (Invitrogen). The pREP4 plasmid is particularly useful since it contains the Epstein Barr virus origin of replication and nuclear antigen EBNA-1 coding region which produces high copy episomal replication without integration. pREP4 also contains the hygromycin marker under the regulatory control of the thymidine kinase promoter and polyadenylation site. The HIV env coding region is placed under the regulatory control of the RSV promoter and SV40 polyadenylation site. The HIV env coding region was obtained as a 2.3 kb PCR fragment form HIV/3B, Genebank sequence K03455. The resulting pCEP4-based plasmid, pRA-101, is maintained extrachromosomally and produces gp160 protein.

Example 39

In another construction for expressing the gag/pol genes, that region of HIV may be inserted into the commercially available plasmid pCEP4 (Invitrogen). The pCEP4 plasmid is particularly useful since it contains the Epstein Barr virus origin of replication and nuclear antigen EBNA-1 coding region which produces high copy episomal replication without integration. pCEP4 also contains the hygromycin marker under the regulatory control of the thymidine kinase promoter and polyadenylation site. The HIV gag/pol coding region is placed under the regulatory control of the CMV promoter and SV40 polyadenylation site. The HIV gag/pol coding region was obtained from HIV MN, Genebank sequence MI7449, and includes the vif gene. The vpr gene is not included. The resulting pCEP4-based plasmid, pLA-100, is maintained extrachromosomally and produces GAG55, reverse transcriptase, protease and integrase proteins.

Example 40

In another construction for expressing the gag/pol genes, that region of HIV may be inserted into the commercially available plasmid pREP4 (Invitrogen). The pREP4 plasmid is particularly useful since it contains the Epstein Barr virus origin of replication and nuclear antigen EBNA-1 coding region which produces high copy episomal replication without integration. pREP4 also contains the hygromycin marker under the regulatory control of the thymidine kinase promoter and polyadenylation site. The HIV gag/pol coding region is placed under the regulatory control of the CMV promoter and SV40 polyadenylation site. The HIV gag/pol coding region was obtained from HIV MN, Genebank sequence MI7449, and includes the vif gene. The vpr gene is not included. The resulting pREP4-based plasmid, pLA-101, is maintained extrachromosomally and produces GAG55, reverse transcriptase, protease and integrase proteins.

Example 41

The following construction, referred to herein as pGAGPOL.rev, is useful to express HIV gag/pol genes.

The plasmid includes a Kanamycin resistance gene and a pBR322 origin of DNA replication. The sequences provided for transcription regulation include: a cytomegalovirus promoter; a Rous sarcoma virus enhancer; and an SV40 polyadenylation signal. The HIV-1 sequences included in pGAGPOL.rev include a sequence that encodes p17, p24, and p15 of the gag open reading frame; a sequence that encodes protease, a sequence that encodes reverse transcriptase which contains a small deletion and a sequence that encodes the inactive amino terminus of integrase of the pol open reading frame; and a sequence that encodes rev. Each of the HIV sequences are derived from HIV-1 strain HXB2.

Several safety features are included in pGAGPOL.rev. These include use of the CMV promoter and a non-retroviral poly(A) site. Furthermore, deletion of the ψ sequence limits the ability to package viral RNA. In addition, multiple mutations of the reverse transcriptase yield an enzymatically inactive product. Moreover, a large deletion of integrase yields an inactive product and a Kanamycin resistance marker is used for stabilizing bacterial transformants.

Plasmid pGAGPOL.rev is constructed as follows.

Step 1. A subclone of part of the HIV-1 (HXB2) genome that is cloned into Bluescript (Stratagene) is used. The subclone of HIV-1 contains the complete 5'LTR and the rest of the HIV-1 genome to nucleotide 5795 (Genebank numbering). The HIV-1 sequences are obtained from the HXB2D plasmid (AIDS Repository).

Step 2. PCR part of gag from the open reading frame HXB2D plasmid (AIDS Repository). Cut PCR fragment with NotI and SpeI and ligate with HIV-1 subclone described above restricted with NotI and SpeI.

Step 3. PCR gag/pol junction and part of pol-encoding sequences from the HXB2D plasmid (AIDS Repository) with primers SEQ ID NO:15 and SEQ ID NO:16. Cut PCR product with ClaI and ligate together. Cut ligated fragments with BclI and SalI and ligate with plasmid from Step 2 digested with BclI and SalI.

Step 4. Cut plasmid from Step 3 with BspMI and EcoRI and religate with adapters formed by annealing linkers SEQ ID NO:17 and SEQ ID NO:18.

Step 5. Cut plasmid from Step 4 with NotI and SalI and ligate with plasmid from either 4a or 4b in description written for PENV (below). Cut also with NotI and SalI.

Step 6. Restrict plasmid from Step 5 with SalI and MluI and ligate with PCR product obtained by PCR of rev with primers SEQ ID NO:19 and SEQ ID NO:20.

Step 7. Cut plasmid from Step 6 with NotI and ligate with product obtained by PCR of the rev responsive element in the HXB2D plasmid (AIDS Repository) with primers SEQ ID NO:21 and SEQ ID NO:22.

Steps 6 and 7 are optional.

Example 42

The following construction, referred to herein as pENV, is useful to express HIV env genes.

The plasmid includes a Kanamycin resistance gene and a pBR322 origin of DNA replication. The sequences provided for transcription regulation include: a cytomegalovirus promoter; a Rous sarcoma virus enhancer; and an SV40 polyadenylation signal. The HIV-1 sequences included in pENV include a sequence that encodes vpu; a sequence that encodes rev; a sequence that encodes gp160; a sequence that encodes 50% of nef; a sequence that encodes vif; and, a sequence that encodes vpr with a 13 amino acid carboxy-end deletion. The vpu, rev, gp160 and nef sequences are derived from HIV-1 strain MN. The vif and vpr sequences are derived from HIV-1 strain HXB2.

Several safety features are included in pGAGPOL.rev. These include use of the CMV promoter and a non-retroviral poly(A) site. Furthermore, tat has been deleted and a 50% deletion of nef yields an "inactive" nef product. In addition, vif and vpr are placed out of normal sequence and a partial deletion of vpr further ensures an inactive vpr product.

Plasmid pENV is constructed as follows.

Step 1. Start with pUC18 digested with HindIII and EcoRI. The resulting fragment that contains the ColE1 origin of replication and the laci gene should be ligated with the EcoRI/HindIII fragment from pMAMneoBlue that contains the our sarcoma virus enhancer. The resulting plasmid or pMAMneo-Blue from Clontech (Palo Alto, Calif.) can then be digested with HindIII and BgII. Using standard techniques, ligate with fragment containing kan gene obtained by PCR of geneblock plasmid (Pharmacia).

Step 2. If pMAMneo-Blue used as starting plasmid, digest with MluI and EcoRI, fill in the ends with Klenow fragment of Polymerase I and religate.

Step 3. Them, with either pMAMneo-Blue or pUC18-derived plasmid, digest with HindIII and ligate with the SV40 polyA site and early splicing region obtained by PCR of pCEP4 (Invitrogen, San Diego Calif.) with primers SEQ ID NO:23 and SEQ ID NO:24.

Step 4a. Digest with BamHI and ligate with the CMV promoter obtained by PCR of pCEP4 (Invitrogen, San Diego Calif.) with primers SEQ ID NO:25 and SEQ ID NO:26.

Step 4b. Digest with BamHI and ligate with the MoMLV LTR obtained by PCR with primers SEQ ID NO:27 and SEQ ID NO:28.

Step 5. Digest with NotI and MluI and ligate with GP160 coding region obtained by PCR of pMN-ST1 with primers SEQ ID NO:29 and SEQ ID NO:30.

Step 6. Digest with MluI and ligate with sequences that encode vif in its entirety and vpr with a 13aa carboxy-end deletion by CPR of HXB2D plasmid (AIDS Repository) with primers SEQ ID NO:31 and SEQ ID NO:32.

Example 43

An immunization system is provided which comprises:

a pharmaceutical composition comprising about 100 µg of pGAGPOL. rev in an isotonic, pharmaceutically acceptable solution; and, a pharmaceutical preparation comprising 100 µg of pENV in an isotonic, pharmaceutically acceptable solution. In addition, the immunization system preferably comprises a pharmaceutical composition comprising about 1 ml of 0.5% bupivacaine-HCl and 0.1% methylparaben in an isotonic pharmaceutical carrier.

In such a preferred immunization system, a first set of administrations is performed in which bupivacaine and one of the two pharmaceutical compositions are administered intramuscularly to an individual, preferably into a muscle of an arm or buttock. Bupivacaine and the other of the two pharmaceutical compositions are administered intramuscularly to the individual at a different site, preferably remote from the site of the administration of the one pharmaceutical composition, preferably into a muscle of the other arm or buttock. Subsequence sets of administrations may be performed later in time, preferably 48 hours to two weeks or more later.

The immunization system may be used to vaccinate an individual in order to protect that individual from HIV infection or to treat an HIV infected individual with an immunotherapeutic.

Example 44

In some embodiments, the present invention relates to a method of immunizing an individual against HIV by administering a single inoculant. This inoculant includes a genetic construct that comprises at least one, preferably two, more preferably more than two or a plurality of the genes of the HIV virus or all of the structural genes. However, the inoculant does not contain a complete complement of all HIV genes. If a single cell is provided with a complete complement of viral genes, it is possible that a complete infectious virus can be assembled within the cell. Accordingly, a genetic construct according to the present invention is not provided with such a full complement of genes. As a safety precaution, one or more essential genes can be deleted or intentionally altered to further ensure that an infectious viral particle cannot be formed.

In some embodiments of the present invention, at least portions of one, two or all HIV structural genes are provided. The structural genes of HIV consist of gag, pol and env. Portions of at least one of these three genes are provided on a genetic construct. Accordingly, in some embodiments, at least a portion of each of gag and pol are provided on a genetic construct; in some embodiments, at least a portion of env is provided on a genetic construct; in some embodiments, at least a portion of gag is provided on a genetic construct; in some embodiments at least a portion of each of pol and env are provided on a genetic construct; in some embodiments, at least a portion of each of gag and env are provided on a genetic construct; in some embodiments at least a portion of pol is provided on a genetic construct. Optionally, the entire gene is provided. Optionally, in any of these constructs, HIV regulatory genes may also be present. The HIV regulatory genes are: vpr, vif, vpu, nef, tat and rev.

Example 45

As used herein, the term "expression unit" is meant to refer to a nucleic acid sequence which comprises a promoter operably linked to a coding sequence operably linked to a polyadenylation signal. The coding sequence may encode one or more proteins or fragments thereof. In preferred embodiments, a expression unit is within a plasmid.

As used herein, the term "HIV expression unit" is meant to refer to a nucleic acid sequence which comprises a promoter operably linked to a coding sequence operably linked to a polyadenylation signal in which the coding sequence encodes a peptide that comprises an epitope that is identical or substantially similar to an epitope found on an HIV protein. "Substantially similar epitope" is meant to refer to an epitope that has a structure which is not identical to an epitope of an HIV protein but nonetheless invokes an cellular or humoral immune response which cross reacts to an HIV protein. In preferred embodiments, the HIV expression unit comprises a coding sequence which encodes one or more HIV proteins or fragments thereof. In preferred embodiments, an HIV expression unit is within a plasmid.

In some embodiments of the present invention, a single genetic construct is provided that has a single HIV expression unit which contains DNA sequences that encode one or more HIV proteins or fragments thereof. As used herein, the term "single HIV expression unit construct" is meant to refer to a single genetic construct that contains a single HIV expression unit. In preferred embodiments, a single HIV expression unit construct is in the form of a plasmid.

In some embodiments of the present invention, a single genetic construct is provided that has more than one HIV expression units in which each contain DNA sequences that encode one or more HIV proteins or fragments thereof. As used herein, the term "multiple HIV expression unit genetic construct" is meant to refer to a single plasmid that contains more than one HIV expression units. In preferred embodiments, a multiple HIV expression unit construct is in the form of a plasmid.

In some embodiments of the present invention, a single genetic construct is provided that has two HIV expression units in which each contain DNA sequences that encode one or more HIV proteins or fragments thereof. As used herein, the term "two HIV expression unit genetic construct" is meant to refer to a single plasmid that contains two HIV expression units, i.e a multiple HIV expression unit genetic construct that contains two HIV expression unit genetic expression units. In a two HIV expression unit genetic construct, it is preferred that one HIV expression unit operates in the opposite direction of the other HIV expression unit. In preferred embodiments, a two HIV expression unit construct is in the form of a plasmid.

In some embodiments of the present invention, an HIV genetic vaccine is provided which contains a single genetic construct. The single genetic construct may be a single HIV expression unit genetic construct, a two HIV expression unit genetic construct or a multiple HIV expression unit genetic construct which contains more than two HIV expression units.

In some embodiments of the present invention, an HIV genetic vaccine is provided which contains more than one genetic construct in a single inoculant.

In some embodiments of the present invention, an HIV genetic vaccine is provided which contains more than one genetic construct in more than one inoculant. As used herein, the term "multiple inoculant" is meant to refer to a genetic vaccine which comprises more than one genetic construct, each of which is administered separately. In some embodiments of the present invention, an HIV genetic vaccine is provided which contains two genetic constructs. Each genetic construct may be, independently, a single HIV expression unit genetic construct, a two HIV expression unit genetic construct or a multiple HIV expression unit genetic construct which contains more than two HIV expression units. In some embodiments, both genetic constructs are single HIV expression unit genetic constructs. In some embodiments, both genetic constructs are two HIV expression unit genetic constructs. In some embodiments, both genetic constructs are multiple HIV expression unit genetic constructs. In some embodiments, one genetic construct is a single HIV expression unit genetic construct and the other is a two HIV expression unit genetic construct. One having ordinary skill in the art can readily recognize and appreciate the many variations depending upon the number of genetic constructs used in a genetic vaccine and the number of HIV expression units that may be present on each genetic construct.

It is preferred that the genetic constructs of the present invention do not contain certain HIV sequences, particularly, those which play a role in the HIV genome integrating into the chromosomal material of the cell into which it is introduced. It is preferred that the genetic constructs of the present invention do not contain LTRs from HIV. Similarly, it is preferred that the genetic constructs of the present invention do not contain a psi site from HIV. Further, it is preferred that the reverse transcriptase gene is deleted and the integrase gene is deleted. Deletions include deletion of only some of the codons or replacing some of the codons in order to essentially-delete the gene. For example, the initiation codon may be deleted or changed or shifted out of frame to result in a nucleotide sequence that encodes an incomplete and non-functioning.

It is also preferred that the genetic constructs of the present invention do not contain a transcribable tat gene from HIV. The tat gene, which overlaps the rev gene may be completely deleted by substituting the codons that encode rev with other codons that encode the same amino acid for rev but which does not encode the required tat amino acid in the reading frame in which tat is encoded. Alternatively, only some of the codons are switched to either change, i.e. essentially delete, the initiation codon for tat and/or change, i.e. essentially delete, sufficient codons to result in a nucleotide sequence that encodes an incomplete and non-functioning tat.

It is preferred that a genetic construct comprises coding sequences that encode peptides which have at least an epitope identical to or substantially similar to an epitope from HIV gag, pol, env or rev proteins. It is more preferred that a genetic construct comprises coding sequences that encode at least one of HIV gag, pol, env or rev proteins or fragments thereof. It is preferred that a genetic construct comprises coding sequences that encode peptides which have more than one epitopes identical to or substantially similar to an epitope from HIV gag, pol, env or rev proteins. It is more preferred that a genetic construct comprises coding sequences that encode more than one of HIV gag, pol, env or rev proteins or fragments thereof.

In some embodiments, a genetic construct comprises coding sequences that encode peptides which have at least an epitope identical to or substantially similar to an epitope from HIV vif, vpr, vpu or nef proteins. In some embodiments, a genetic construct comprises coding sequences that encode at least one of HIV vif, vpr, vpu or nef proteins or fragments thereof.

A single HIV expression unit genetic construct may comprise coding regions for one or more peptides which share at least one epitope with an HIV protein or fragment thereof in a single expression unit under the regulatory control of single promoter and polyadenylation signal. It is preferred that genetic constructs encode more than one HIV protein or fragment thereof. The promoter may be any promoter functional in a human cell. It is preferred that the promoter is an SV40 promoter or a CMV promoter, preferably a CMV immediate early promoter. The polyadenylation signal may be any polyadenylation signal functional in a human cell. It is preferred that the polyadenylation signal is an SV40 polyadenylation signal, preferably the SV40 minor polyadenylation signal. If more than one coding region is provided in a single expression unit, they may be immediately adjacent to each other or separated by non-coding regions. In order to be properly expressed, a coding region must have an initiation codon and a termination codon.

A two HIV expression unit genetic construct may comprise coding regions for one or more peptides which share at least one epitope with an HIV protein or fragment thereof on each of the two expression units. Each expression unit is under the regulatory control of single promoter and polyadenylation signal. In some embodiments, it is preferred that genetic constructs encode more than one HIV protein or fragment thereof. In some embodiments, it is preferred that nucleotide sequences encoding gag and pol are present on one expression unit and nucleotide sequences encoding env and rev are present on the other. The promoter may be any promoter functional in a human cell. It is preferred that the promoter is an SV40 promoter or a CMV promoter, preferably a immediate early CMV promoter. The polyadenylation signal may be any polyadenylation signal functional in a human cell. It is preferred that the polyadenylation signal is an SV40 polyadenylation signal, preferably the SV40 minor polyadenylation signal. If more than one coding region is provided in a expression unit, they may be immediately adjacent to each other or separated by non-coding regions. In order to be properly expressed, a coding region must have an initiation codon and a termination codon.

According to some embodiments of the present invention, the MHC Class II crossreactive epitope in env is deleted and replaced with the analogous region from HIV II.

When a genetic construct contains gag and/or pol, it is generally important that rev is also present. In addition to rev, a rev response element may be provided with gag and pol for increased expression of those genes.

When genetic constructs are produced that it is preferred that the env gene used in plasmid 1 is derived from MN or MN-like isolates including clinical isolates resembling MN, preferably non-syncytial inducing clinical isolates, preferably those that are macrophage tropic from early stage clinical isolates.

Multiple proteins may be produced from a single expression unit by alternative splicing. Splicing signals are provided tp allow alternative splicing which produces different messages encoding different proteins.

Example 46

FIG. 8 shows four backbones, A, B, C and D. FIG. 9 shows 4 inserts, 1, 2, 3 and 4. Insert 1 supports expression of gag and pol; the rev response element was cloned in a manner to conserve the HIV splice acceptor. Insert 2 is similar to insert 1 as it too supports expression of gag and pol except the rev response element was cloned without conserving the HIV splice acceptor Insert 3 supports expression of gag and pol, includes a deletion of the integrase gene and does not include the presence of the cis acting rev response element. Insert 4 supports expression of rev, vpu and env. The env may have the MHC class II cross reactive epitope altered to eliminate cross-reactivity and the V3 loop may be altered to eliminate the possibility of syncytia formation.

In some embodiments, backbone A is used with insert 1. Such constructs optionally contain the SV40 origin of replication. Plasmid pA1ori+ is backbone A with insert 1 and the SV40 origin of replication. Plasmid pA1ori− is backbone A with insert 1 without the SV40 origin of replication. Additionally, either pA1ori+ or pA1ori− may include integrase yielding pA1ori+int+ and pA1ori−int+, respectively. Plasmids pA1ori+, pA1ori−, pA1ori+int+ and pA1ori−int+ may be further modified by functionally deleing the reverse transcriptase (RT) gene yielding pA1ori+RT−, pA1ori−RT−, pA1ori+int+RT− and pA1ori−int+RT−, respectively.

In some embodiments, backbone A is used with insert 2. Such constructs optionally the SV40 origin of replication. Plasmid pA2ori+ is backbone A with insert 2 and the SV40 origin of replication. Plasmid pA2ori− is backbone A with insert 1 without the SV40 origin of replication. Additionally, either pA2ori+ or pA2ori− may include integrase yielding pA2ori+int+ and pA2ori−int+, respectively. Plasmids pA2ori+, pA2ori−, pA2ori+int+ and pA2ori−int+ may be further modified by functionally deleing the reverse transcriptase (RT) gene yielding pA2ori+RT−, pA2ori−RT−, pA2ori+int+RT− and pA2ori−int+RT−, respectively.

In some embodiments, backbone B is used with insert 1. Such constructs optionally the SV40 origin of replication. Plasmid pB1ori+ is backbone B with insert 1 and the SV40 origin of replication. Plasmid pB1ori− is backbone B with insert 1 without the SV40 origin of replication. Additionally, either pB1ori+ or pB1ori− may include integrase yielding pB1ori+int+ and pB1ori−int+, respectively. Plasmids pB1ori+, pB1ori−, pB1ori+int+ and pB1ori−int+ may be further modified by functionally deleting the reverse transcriptase (RT) gene yielding pB1ori+RT−, pB1ori−RT−, pB1ori+int+RT− and pB1ori−int+RT−, respectively.

In some embodiments, backbone B is used with insert 2. Such constructs optionally the SV40 origin of replication. Plasmid pB2ori+ is backbone B with insert 2 and the SV40 origin of replication. Plasmid pB2ori− is backbone B with insert 1 without the SV40 origin of replication. Additionally, either pB2ori+ or pB2ori− may include integrase yielding pB2ori+int+ and pB2ori−int+, respectively. Plasmids pB2ori+, pB2ori−, pB2ori+int+ and pB2ori−int+ may be further modified by functionally deleing the reverse transcriptase (RT) gene yielding pB2ori+RT−, pB2ori−RT−, pB2ori+int+RT− and pB2ori−int+RT−, respectively.

In some embodiments, backbone A minus rev is used with insert 3. Such constructs optionally the SV40 origin of replication. Plasmid pA/r-3ori+ is backbone A with insert 2 and the SV40 origin of replication. Plasmid pA/r-3ori− is backbone A minus rev with insert 3 without the SV40 origin of replication. Additionally, either pA/r-3ori+ or pA/r-3ori− may include integrase yielding pA/r-3ori+int+ and pA/r-3ori− int+, respectively. Plasmids pA/r-3ori+, pA/r-3ori−, pA/r-3ori+int+ and pA/r-3ori−int+ may be further modified by functionally deleing the reverse transcriptase (RT) gene yielding pA/r-3ori+RT−, pA/r-3ori−RT−, pA/r-3ori+int+RT− and pA/r-3ori−int+RT−, respectively.

In some embodiments, backbone C is used with insert 1. Such constructs optionally the SV40 origin of replication. Plasmid pC1ori+ is backbone C with insert 1 and the SV40 origin of replication. Plasmid pC1ori− is backbone C with insert 1 without the SV40 origin of replication. Additionally, either pC1ori+ or pC1ori− may include integrase yielding pC1ori+int+ and pC1ori−int+, respectively. Plasmids pC1ori+, pC1ori−, pC1ori+int+ and pC1ori−int+ may be further modified by functionally deleing the reverse transcriptase (RT) gene yielding pC1ori+RT−, pC1ori−RT−, pC1ori+int+RT− and pC1ori−int+RT−, respectively.

In some embodiments, backbone C is used with insert 2. Such constructs optionally the SV40 origin of replication. Plasmid. pC2ori+ is backbone C with insert 2 and the SV40 origin of replication. Plasmid pC2ori− is backbone C with insert 2 without the SV40 origin of replication. Additionally, either pC2ori+ or pC2ori− may include integrase yielding pC2ori+int+ and pC2ori−int+, respectively. Plasmids pC2ori+, pC2ori−, pC2ori+int+ and pC2ori−int+ may be further modified by functionally deleing the reverse transcriptase (RT) gene yielding pC2ori+RT−, pC2ori−RT−, pC2ori+int+RT− and pC2ori−int+RT−, respectively.

In some embodiments, backbone C is used with insert 3. Such constructs optionally the SV40 origin of replication. Plasmid pC3ori+ is backbone C with insert 3 and the SV40 origin of replication. Plasmid pC3ori− is backbone C with insert 3 without the SV40 origin of replication. Additionally, either pC3ori+ or pC3ori− may include integrase yielding pC3ori+int+ and pC3ori−int+, respectively. Plasmids pC3ori+, pC3ori−, pC3ori+int+ and pC3ori−int+ may be further modified by functionally deleing the reverse transcriptase (RT) gene yielding pC3ori+RT−, pC3ori−RT−, pC3ori+int+RT− and pC3ori−int+RT−, respectively.

In some embodiments, backbone D is used with insert 4. Such constructs optionally the SV40 origin of replication.

Plasmid pD4ori+ is backbone D with insert 4 and the SV40 origin of replication. Plasmid pD4ori− is backbone D with insert 4 without the SV40 origin of replication.

Example 47

In some embodiments, a single expression unit/single inoculant genetic vaccine is provided which comprises a genetic construct that includes a coding sequence which encodes a peptide that has at least one epitope which is an identical to or substantially similar to epitopes of HIV proteins. The coding sequence is under the regulatory control of the CNV immediate early promoter and the SV40 minor polyadenylation signal.

In some embodiments, a single expression unit/single inoculant genetic vaccine is provided which comprises a genetic construct that includes a coding sequence which encodes at least one HIV protein or a fragment thereof. The coding sequence is under the regulatory control of the CMV immediate early promoter and the SV40 minor polyadenylation signal. The HIV protein is selected from the group consisting of gag, pol, env and rev. In some embodiments it is preferred that the genetic vaccine is provided which comprises a genetic construct that includes a coding sequence which encodes at least two HIV proteins or a fragments thereof selected from the group consisting of gag, pol, env and rev or fragments thereof. In some embodiments, it is preferred that the genetic vaccine is provided which comprises a genetic construct that includes a coding sequence which encodes at least three HIV proteins or a fragments thereof selected from the group consisting of gag, pol, env and rev or fragments thereof. In some embodiments, it is preferred that the genetic vaccine is provided which comprises a genetic construct that includes a coding sequence which encodes gag, pol, env and rev or fragments thereof.

In some embodiments, a dual expression unit/single inoculant genetic vaccine is provided which comprises a genetic construct that includes two expression units each of which comprises a coding sequence which encodes a peptide that has at least one epitope which is an identical to or substantially similar to epitopes of HIV proteins. The coding sequence is under the regulatory control of the CMV immediate early promoter and the SV40 minor polyadenylation signal. The two expression units are encoded in opposite directions of each other.

In some embodiments, a dual expression unit/single inoculant genetic vaccine is provided which comprises a genetic construct that includes two expression units each of which comprises a coding sequence which encodes at least one HIV protein or a fragment thereof. Each expression unit comprises a coding sequence that is under the regulatory control of the CMV immediate early promoter and the SV40 minor polyadenylation signal. The HIV protein is selected from the group consisting of gag, pol, env and rev. In some embodiments it is preferred that the genetic vaccine is provided which comprises a genetic construct that includes two expression units, at least one of which comprises a coding which encodes at least two HIV proteins or a fragments thereof selected from the group consisting of gag, pol, env and rev or fragments thereof and the other comprises at least one HIV proteins or a fragments thereof selected from the group consisting of gag, pol, env and rev or fragments thereof. In some embodiments, it is preferred that the genetic vaccine is provided which comprises a genetic construct that includes two expression units, at least one of which comprises a coding sequence which encodes at least three HIV proteins or a fragments thereof selected from the group consisting of gag, pol, env and rev or fragments thereof and the other comprises at least one HIV proteins or a fragments thereof selected from the group consisting of gag, pol, env and rev or fragments thereof. In some embodiments, it is preferred that the genetic vaccine is provided which comprises a genetic construct that comprises two expression units and includes a coding sequence which encodes gag, pol, env and rev or fragments thereof.

Example 48

A genetic construct, plasmid pCMN160Δ16 was made for use in an anti-HIV pharmaceutical kit or pharmaceutical composition. pCMN160Δ16 was constructed as follows:

Step 1: Primers SEQ ID NO:35 and SEQ ID NO:34 were used a PCR fragment from HIV/MN genomic DNA.

Step 2: Primers SEQ ID NO:33 and SEQ ID NO:36 were used a PCR fragment from HIV/MN genomic DNA.

Step 3: Primers SEQ ID NO:35 and SEQ ID NO:36 were combined with 2 μg of reaction material from Steps 1 and 2.

Step 4: Reaction-product from Step 3 was cut with Not1 and Mlu1 and inserted into Backbone A described in Example 46 cut with Not1 and Mlu1.

Plasmid pCMN160Δ16 is thereby formed which contains as an insert to Backbone A a coding region which encodes the MN strain ENV Protein with the rev region and half of net having HLA-DB region changes to HIV-2.

Example 49

The plasmid pGAGPOL.rev2 was made as follows. First the backbone was made. Then an insert with HIV gag and pol was generated and inserted into the backbone.

The backbone was prepared as follows.

Step 1. Digest pMAMneo (Clonetech) with Bgl1. Fill-in with Klenow fragment of Polymerase I. Cut with HindIII. Gel purify 1763 bp fragment.

Step 2. Amplify $Kan^R$ gene from plasmid pJ4Ωkan$^+$ (Kanmycin resistance gene obtained from Pharmacia Inc. cloned into pJ4Ω obtained as a gift from the Imperial Cancer Research Fund UK; pJ4Ω was originally constructed and reported by Morgenstern, J. P. and H. Land, *Nucl. Acids Res.* 18(4):1068, which is incorporated herein by reference) with oligos SEQ ID NO:37 and SEQ ID NO:38. Blunt off PCR product. Cut with HindIII. Gel purify PCR fragment.

Step 3. Ligate the vector backbone generated from pMAMneo and described in step #1 with the PCR product encoding the $Kan^R$ gene and described in step #2. Isolate plasmid containing the $Kan^R$ gene and the bacterial origin of replication.

Step 4. Digest resulting plasmid with MluI, fill-in with Klenow fragment of DNA polymerase I. Ligate with SacII linker (New England Biolabs).

Step 5. Digest plasmid obtained in step 4 with AseI and SspI.

Step 6. PCR part of the $Kan^R$ gene from the plasmid described in step 3 using primers SEQ ID NO:39 and SEQ ID NO:40. Cut PCR product with SspI and AseI.

Step 7. Ligate largest fragment obtained in step 5 with PCR product obtained in step 6.

Step 8. Cut ligation product/plasmid obtained in step 7 with HindIII. Blunt off with the Klenow fragment of DNA polymerase I.

Step 9. Cut pCEP4 (Invitrogen) with SalI to release a DNA fragment containing the CMV promoter, polylinker, and SV40 poly A site. Purify this fragment and blunt-off with the Klenow fragment of DNA Polymerase I.

Step 10. Ligate the plasmid obtained in step 8 and the fragment obtained in step 9. Isolate plasmid containing the bacterial origin of replication, the Kan$^R$ gene, the RSV enhancer, the CMV promoter, polylinker, and the SV40 poly A site.

Step 11. Cut plasmid obtained in step 10 with BamHI and NheI.

Step 12. Anneal oligonucleotides SEQ ID NO:41 and SEQ ID NO:42.

Step 13. Ligate the plasmid obtained in step 10 with the annealed oligonucleotides obtained in step 12. Isolate plasmid containing the adapter contained in step. 12.

Step 14. Digest plasmid obtained in step 13 with SalI and MluI.

Step 15. PCR amplify the rev open reading frame using BBG35 (RD Systems Inc. Minneapolis, Minn.; which contains the coding region for rev from HIV strain HX3B in pUC19) as a template and primers SEQ ID NO:43 and SEQ ID NO:44. Digest the PCR product with SalI and MluI.

Step 16. Ligate the plasmid obtained in step 14 with the PCR product produced in step 15. Isolate plasmid containing the rev coding region.

Preparation of gag/pol Insert.

Step 1. A subclone of part of the HIV-I (HXB2) genome that was cloned into Bluescript (Stratagene). The subclone of HIV-1 contains the complete 5'LTR and the rest of the HIV-1 genome to nucleotide 5795 (Genbank numbering) cloned into the XbaI and SalI sites of Bluescript. The HIV-1 sequences are obtained from the HXB2D plasmid (AIDS Repository).

Step 2. PCR part of the gag coding region from the open reading frame of the plasmid described in step 1 (the subclone of part of the HIV-1HXB2 genome that is cloned into Bluescript) using primers SEQ ID NO:45 and SEQ ID NO:46:

Step 3. Digest plasmid described in step 1 (the subclone of part of the HIV-1 HXB2 genome that is cloned into Bluescript) with EcoRI. Purify the plasmid that contains the pBluescript backbone, the 5' HIV-1 LTR, the gag coding region and part of the pol coding region and religate.

Step 4. Cut the plasmid obtained in step 3 with NotI and SpeI and ligate with the PCR fragment described in Step 2 after it is digested with NotI and SpeI. Isolate plasmid that contain the PCR fragment instead of the original NotI/SpeI fragment which contains the 5' HIV-1 LTR.

Step 5. Digest the plasmid obtained in step 4 with EcoR1 and SalI.

Step 6. Anneal oligonucleotides SEQ ID NO:47 and SEQ ID NO:48.

Step 7. Ligate the plasmid obtained in step 5 with the adapter obtained in step 6. Isolate plasmid containing the adapter cloned into the EcoRI/SalI sites.

Step 8. Digest the plasmid obtained in step 7 with NdeI and EcoRI.

Step 9. PCR amplify the Rev Response Element (RRE) from a plasmid containing the RRE sequence from HIV-1 strain HXB2 using primers SEQ ID NO:49 and SEQ ID NO:50. Digest the PCR product with NdeI and EcoRI.

Step 10. Ligate the plasmid obtained in step 8 with the PCR product obtained in step 9. Isolate plasmid containing the insert with the RRE sequence.

Step 11. Digest the plasmid obtained in step 10 with NotI and SalI and isolate the fragment containing the gag coding region, the modified pol coding region, and the RRE sequence.

Step 12. Digest the plasmid obtained in step 16 of the protocol for preparing the backbone which is described above with NotI and SalI.

Step 13. Ligate the plasmid obtained in step 12 with the insert obtained in step 11. Isolate plasmids that contain the insert containing the gag coding region, the modified pol coding region, and the RRE sequence.

Step 14. Digest plasmid obtained in step 13 with XbaI and NheI, Blunt-off ends and religate. Isolate the plasmid that is lacking the KpnI site that is present between the XbaI and NheI sites in the plasmid obtained in step 13.

Step 15. Digest the plasmid obtained in step 14 with KpnI and isolate the largest fragment.

Step 16. Anneal oligonucelotides SEQ ID NO:51 and SEQ ID NO:52.

Step 17. Ligate the purified plasmid fragment obtained in step 15 with the adapter obtained in step 16. Isolate plasmid containing the adapter inserted at the KpnI site of the plasmid obtained in step 15.

Example 50

Genetic Immunization with Genes for Regulatory Proteins

Part of the difficulty of combatting HIV arises from the extraordinary variability of the virus and its ability to quickly mutate into new forms. Not only is there substantial protein sequence variation among HIV isolates found in the human population as a whole, but the virus mutates so quickly that every HIV-infected individual actually harbors a number of related HIV microvariants. Such HIV isolates exhibit differences in replication efficiency, tropism, susceptibility to neutralization, and drug resistance. As drug-resistant mutants appear, the benefits of drug therapy fade. With AZT, drug resistance typically arises within the first year of therapy. This constant generation of escape mutants may play a part in the ability of HIV to finally overwhelm host defenses after a long period in which the virus appears to be held in check.

This mutational drift has been reported in various regions of the gp120 envelope glycoprotein, including the principal neutralizing domain of the V3 loop, and in the HIV core proteins as well. HIV regulatory proteins are much more highly conserved than the structural proteins and also exhibit less mutational drift over time. Regulatory proteins therefore present attractive targets for antiviral attack.

HIV exhibits a remarkable temporal regulation of expression of regulatory vs structural proteins. In the early phase of viral replication, mRNAs encoding the regulatory proteins Tat, Rev and Nef predominate, whereas in the late phase, there is greater expression of mRNAs encoding structural proteins, including Gag, Pol, and Env precursors, and many accessory proteins. This shift from early to late phase is triggered when the Rev protein reaches a particular level. The predominance of Tat, Rev and Nef early in the viral replication cycle also makes these proteins favorable targets for antiviral attack. This is especially true for tat and rev, which play absolutely essential roles in transcriptional and post-translational regulation of HIV gene expression, and predominate early in the viral replication cycle, before transcription of viral structural proteins and production of infectious viral particles.

In contrast to tat and rev, which clearly play essential roles in HIV replication, other regulatory proteins such as nef, vpr, vif, and vpu are sometimes referred to as "accessory" proteins. Their functions are less well understood, and the degree to which viral replication is attenuated by loss of a particular function varies considerably and may depend on the host cell being infected. Nevertheless, the strong conservation of such functions among widely diverse HIV isolates, as well as other primate immunodeficiency viruses, suggests the importance of these "accessory" functions in the natural infection process. (See in general, Terwilliger, E. F., (1992) *AIDS Research Reviews* 2:3-27, W. C. Koff, F. Wong-Staal, and R. C. Kennedy, eds. (New York: Marcel Dekker, Inc.). In fact, primate recombinant viruses deleted in either vpr, nef or vif are non-pathogenic in vivo, further demonstrating the importance of these accessory genes in the life cycle of the virus.

There is some evidence that higher level, more protective immune responses against HIV could be achieved by presenting a select few regulatory and/or enzymatic proteins, rather than the entire complement of HIV genes. Accordingly, a focused immunization strategy may desirably involve genetic immunization using coding sequences for one or more regulatory, non-structural HIV proteins, including tat, rev, vpr, nef, vpu or vif. Only vpr has been found to be associated with viral particles, whereas other regulatory proteins, including tat, rev, net, vif and vpu, are not virion associated.

In some embodiments of genetic immunization against HIV using regulatory genes, the one or more of tat, rev, net, vif and vpu genes are inserted into backbone A which is described in Example 46. It is preferred that tat and/or rev is used. In some embodiments, tat or rev are inserted into backbone A which is described in Example 46. In some embodiments, Next in descending order of desirability as targets are net, vpr, vif, and vpu. Preferably, more than one regulatory gene will be employed, including tat and rev; tat, rev, and net; tat, rev, net, and vpr; tat, rev, net, vpr, and vif; tat, rev, net, vpr, vif, and vpu; as well as combinations thereof; and, optionally, such additional regulatory genes as tev.

The Tat protein is a transactivator of LTR-directed gene expression. It is absolutely essential for HIV replication. Tat is produced early in the viral replication cycle and functional Tat is required for expression of Gag, Pol, Env and Vpr. The predominant form of Tat is an 86-amino acid protein derived from two exon mRNAs. The amino-terminal 58 amino acids are sufficient for transactivation, although with reduced activity. Tat acts on a cis-acting sequence termed tar, to produce a dramatic increase in LTR-driven gene expression. Tat may act in part through increased RNA synthesis and in part by increasing the amount of protein synthesized per RNA transcript. Until recently, Tat was thought to act only on the HIV-1 LTR. However, Tat-activated expression from the JC virus late promoter has also been reported. Tat may also stimulate cell proliferation as an exogenous factor, and may play a contributory role in promoting the growth of Kaposi's Sarcoma in HIV-infected individuals. Because of such potentially detrimental effects in both HIV-infected and -noninfected individuals, preferred tat constructs employed for genetic immunization are modified to express only non-functional Tat. Mutations capable of inactivating Tat or Rev can in addition act as transdominant mutations, thereby potentially inactivating any functional Tat being produced in an HIV-infected individual.

Rev is a second regulatory protein of HIV that is essential for viral replication. It is a 19 kD (116 amino acid) protein which is expressed from two coding exons found in a variety of multiply spliced mRNAs. Two distinct domains have been identified, a basic region involved in binding to RRE (Rev-response-element) containing transcripts and an "activation" domain that induces nuclear exports of such transcripts as a result of binding. In the course of natural viral infection, Rev is required for expression of the HIV structural proteins Gag, Pol, and Env, as well as Vpr.

Vpr is a 15 kD protein (96 amino acids) in most HIV-1 strains, although the Vpr open reading frame is extensively truncated in many viral strains extensively passaged in cell culture. The vpr open reading frame is also present in HIV-2 and most SIV isolates. Vpr is the first retroviral regulatory protein found to be associated with HIV viral particles. Its presence in the HIV virion suggests it may serve a function at some early point in the viral replication cycle. Vpr accelerates HIV replication, especially early in infection. Vpr increases the level of expression of reporter genes linked to the HIV LTR by about three fold. Moreover, Vpr and Tat appear to act synergistically with respect to LTR-linked genes. Vpr can be isolated from the serum of HIV-infected individuals and appears to increase the ability of the virus to infect new cells. Vpr has also been found to inhibit cell proliferations and to induce cell differentiation (Levy, D. N. et al., *Cell* (1993) 72:1-20), a finding that may be significant in view of reports that primary monocyte/macrophages are infectible in vitro only while undergoing differentiation (Schuitemaker, H. et al., (1992) *J. Clin. Invest.* 89:1154-1160. Even cells that are unable to support HIV replication may be disregulated by the effects of Vpr. For example, Vpr may be responsible for the muscle wasting frequently observed in AIDS patients. Because of the potentially detrimental activity of Vpr, genetic immunization should preferably be carried out with a modified vpr construct which will express a non-functional Vpr protein.

Nef (also called 3' orf in older literature) is a 25-27 kD protein. It has been suggested that Nef may be involved in the downregulation of CD4+T lymphocytes. In addition, Nef may play a role in cell signaling. Nef appears to be important for the establishment of HIV infection in vivo. Nef-specific CTLs are believed to be important in controlling HIV infection in vivo.

Vif is a 23 kD cytoplasmic protein designated "viral infectivity factor". Although Vif-defective mutant viruses are not compromised with respect to cell-to-cell transmission, they exhibit a profound decrease in ability to infect many CD4+ cell lines. Without Vif, there is decreased budding of virus, and decreased infectivity. In primate studies, Vif deletion mutants exhibit a severely diminished ability to establish infection in vivo. These studies support a clinical role for Vif in virus replication in the host.

Vpu is a 15-20 kD (81 amino acid) protein. Although Vpu(+) and Vpu(−) viruses produce the same amount of viral protein, the latter exhibit increased intracellular accumulation of viral proteins together with decreased extracellular virus. This suggests that Vpu may be involved in the assembly and/or release of viral particles.

Simple retroviruses, such as murine and avian viruses, lack proteins analogous to the HIV-1, HIV-2, and SIV regulatory proteins. In such animals retroviral infection tends to be self-limiting, with clearance of virus and decreased pathogenicity. Similarly, HTLV-1, which includes only Tax (which acts much like Tat and also exhibits vpr-like activity) and Rex (which acts much like Rev) is cleared in many individuals. Genetic immunization with regulatory genes is considered relevant not only for HIV, but also for viruses such as HBV (X gene product) and HCV, and HTLV-1 (Tax) and (Rex). In all of these viruses the regulatory genes are believed to play a critical role in the virus life cycle and the establishment of infection.

Example 51

Construction of KIV-1 Regulatory Plasmid, pREG

The pREG plasmid is constructed in a stepwise fashion, and each intermediate can be tested for protein expression before construction is continued. An expression vector supporting the expression of tat and rev is constructed via two steps. First, an amplification product containing a 5' NheI site, the HIV-1 major splice donor site, the majority of the tat coding region, the region encoding the amino terminal region of the rev protein and an AvaII site is amplified from a synthetic template. This synthetic template is generated using the published sequences of HXB2 strain of HIV-1 obtained from the GenBank Database, and is altered to mutate the cysteine residues at positions 22 and 30 of the tat protein. These mutations have been shown to render tat non-functional (Kuppuswamy, et al. (1989) *Nucleic Acids Research* 17(9): 3551-3561).

The PCR product is ligated into a vector that is digested with NheI and AvaII and which contains a kanamycin resistance gene and a pBR322 origin of replication. In addition, this plasmid contains a cytomegalovirus promoter, a Rous sarcoma virus enhancer, the rev coding region and a SV40 polyadenylation signal. The rev sequence present in the plasmid is derived from the proviral clone of HIV-1 III$_B$. This will generate an expression vector containing a complete, but mutated, tat coding region and a complete rev coding region.

The subsequent step is performed to generate a PCR product containing an AvaII site at its 5' end, a mutation at amino acid position 81 of rev, approximately 30% of the rev coding region, approximately 30% of the nef coding region, and a MluI site at the 3' end. The amino acid change at position 81 has been shown to eliminate rev function, and therefore, the resulting plasmid will lead to production of non-functional rev protein (Bogard, H. and Greene, W. C. (1993) *J. Virol.* 67(5):2496-2502). It is assumed that the major deletion of the nef coding region will result in production of a non-functional nef protein. The 5' AvaII site and the mutation at amino acid position 81 of the rev protein are introduced on the 5' PCR primer which is complementary to the coding region of rev containing both the AvaII site and the nucleotide encoding amino acid 81. A stop codon causing termination of Nef at amino acid position 63 and the 3' coding cloning site, MluI, will be introduced by the 3' PCR primer. The template for this PCR amplification is a plasmid or synthetic template containing the rev and nef coding regions from the MN strain of HIV-1. The resulting PCR product will be digested with AvaII and MluI, and used to replace the smaller AvaII-MluI fragment which results after digestion of the tat-rev plasmid described in the preceding paragraph with AvaII and MluI.

Optionally, vpr can be added to this plasmid in one of two sites. In one approach, vpr can be amplified using a 5' PCR primer containing MluI site upstream of sequences which span the vpr translational start codon and a 3' PCR primer complementary to the vpr stop codon and sequences that flank it which also contain a MluI cloning site. Sequences upstream of the start codon contain a splice acceptor. The PCR product can be digested with MluI and inserted into the tat rev nef plasmid described above after its digestion with MluI.

Alternatively, the vpr amplification can be performed in analogous manner, however, the PCR primers would contain restriction sites compatible with cloning into another vector so that it is expressed under the control of a second eukaryotic promoter. The cassette derived from this plasmid, containing the second promoter followed by the vpr coding region, followed by the a polyA sequence, could be released by digestion with restriction enzymes that flank the cassette, but do not cut within it. The resulting DNA fragment would be cloned into a unique site of the tat, rev, vpr plasmid that falls outside of the region necessary for the expression of tat rev vpr. In this way, a plasmid having two expression units is formed.

Example 52

Construction of HCV and HTLV-1 Plasmids

A similar approach can be used to generate a plasmid expressing HTLV-1 or HCV encoded proteins having enzymatic functions required for the viral life cycle and/or for the regulatory proteins of these viruses. For HTLV-1, a plasmid encoding the regulatory protein, TAX, is generated using the a plasmid backbone and a cloning strategy similar to those described above. Such HCV genes that encode enzymatic proteins include the RNA-dependent RNA-polymerase, a protein having helicase/protease function. The sequences necessary are published and available through GenBank. The viral organization of HTLV-1 and HCV are published in Cann, A. J. and Chen, I. S. Y. *Virology* 2nd Edition, edited by B. N. Fiddr, Raven Press, Ltd., New York, 1990 and Bradley, D. W. *Transfusion Medicine Reviews*, 1(2):93-102, 1992, respectively.

Example 53

Genetic Immunization with Enzymatic Genes

Genetic immunization with genes encoding proteins with enzymatic functions, such as the HIV pol gene can also be an important antiviral strategy since enzymes such as Pol are necessary for the production of live virus. Without polymerase or any of its component functions, HIV is non-pathogenic and non-infectious. Similarly, the enzymatic genes of other viruses, such as the HBV polymerase, are attractive targets for genetic immunization. See, e.g., Radziwill et al., Mutational Analysis of the Hepatitis B Virus P Gene Product: Domain Structure and RNase H Activity, *J. Virol.* 64 (2): 613-620 (1990).

One reason for the attractiveness of viral enzymes as an immunological target is the limited ability of such enzymes to mutate their amino acid sequence and still maintain their enzymatic functions. For example, with HIV-1, Pol exhibits a limited number of "escape" mutations that are associated with resistance to nucleotide analogs such as AZT. However, the vast majority of immunological targets within the protein are preserved even in the drug escape mutants.

Example 54

Construction of RBV Polymerase Plasmid

Experiments reported in the literature indicate that HBV polymerase expression has been achieved in tissue culture cells when both the core and polymerase open reading frames are present in a mRNA molecule. It has also been demonstrated that in this situation, mutation of the core ATG did not influence polymerase expression.

The HBV genome is amplified from a plasmid containing a head-to-tail dimer of the ADW HBV strain. Because expression of polymerase only, and not core is desired, the 5' PCR primer is designed to mutate the precore and core translation initiation codons. In addition, this primer also introduces a mutant DR1 sequence to eliminate the possibility of the generation of a replication-competent HBV genomic RNA. This PCR product is placed into a plasmid containing a kanamycin resistance gene and a pBR322 origin of replication. In addition, this plasmid contains a cytomegalovirus promoter, a Rous sarcoma virus enhancer, and a SV40 polyadenylation signal. The translation initiation codons for surface antigen and the product of the X coding region are mutated to prevent the expression of the HBS and X gene products.

According to another approach to achieve expression of the HBV polymerase, a PCR product encoding the entire polymerase coding region is amplified and cloned into a vector containing a kanamycin resistance gene and a pBR322 origin of replication. In addition, this plasmid contains a cytomegalovirus promoter, a Rous sarcoma-virus enhancer, and a SV40 polyadenylation signal. The 5' PCR primer for this amplification contains a cloning site and spans the translational initiation codon of the polymerase gene. The 3' PCR product contains a restriction site for cloning the insert into the expression vector and also is complementary to the traditional stop codon of the HBV polymerase gene and sequences that flank this stop codon. After ligation of this PCR product into a plasmid containing the kanamycin resistance gene, a pBR322 origin of replication, a cytomegalovirus promoter, a Rous sarcoma virus enhancer, and a SV40 polyadenylation signal, the translation initiation codons for the Hepatitis B surface antigen and X genes are mutated to prevent expression of these gene products. An alternative strategy is used similar to that described above, however, the 3' PCR primer in this case includes the HBVpolyA signal and sequences which flank this signal. This 3' primer is used in the case that sequences including and/or surrounding the HBV polyA signal are important for expression. A mutational analysis has demonstrated that the function of the HBV polymerase gene product can be eliminated by particular nucleotide changes (Radziwell, G. et al. (1990) *J. Virol.* 64(2):613-620). Before utilizing a plasmid constructed as described above, the expressed polymerase can be mutated by the introduction of one of these mutations or others that are analogous.

Example 55

Granulocyte-macrophage colony stimulating factor (GM-CSF) exhibits stimulatory effects on a variety of cell lineages including neutrophils, monocyte/macrophages and eosinophils. The effects of GM-CSF make it an attractive therapeutic model. GM-CSF has been approved by the FDA for use in the autologous bone marrow transplantation and clinical trials have been initiated to test the efficacy in the treatment of various neutropenias. Presently, GM-CSF is administered as a protein which usually requires that it be administered in multiple doses. Proteins must be produced and purified.

An alternative approach to the use of GM-CSF protein is the direct administration of a gene construct which contains a gene encoding GM-CSF in conjunction with the administration of bupivacaine. The genetic construct is constructed by PCR of a GM-CSF gene including signal sequence. The genetic construct preferably contains a kanamycin resistance gene (aminoglycoside 3'-phosphotransferase gene), a bacterial origin of replication, sequences that support expression of the GM-CSF coding region in the cells that the plasmid is introduced into such as the vectors described as backbones in Example 46. The plasmid preferably contains a mammalian origin of replication induced by the cellular replication associated with bupivacaine administration. If the EBV origin of replication is used, the sequence that encodes the nuclear antigen EBNA-1 is also included with the appropriate regulatory sequences. The primers for PCR amplification of the insert contain restriction enzyme sites to allow cloning into the expression vector and are complementary to the 5' and 3' ends of the GM-CSF coding sequences. The PCR reaction is performed with a cDNA clone as described in Lee et al. *Proc. Natl. Acad. Sci., USA* 82:4360-4364.

Example 56

Chronic myelogenous leukemia (CML) is a clonal myeloproliferative disorder of the hematopoietic stem cells associated with the Philadelphia chromosome; a chromosome abnormality resulting from translocation between chromosomes 9 and 22. The breakpoints on chromosome 22 are clustered in a 6 kb region termed the breakpoint cluster region (BCR), while on chromosome 9, the breakpoints are scattered throughout a 90 kb region upstream from c-abl exon 2. The various 9:22 translocations that result can be subdivided into two types: K28 translocations and L6 translocations. Transcription through the bcr-abl translocation results in the generation of fusion mRNAs. Antisense targeted to the bcr-abl junction of the mRNAs has been demonstrated to decrease the ability of hematopoietic cells obtained from CML patients to form colonies.

A genetic construction that encodes the antisense is administered together with bupivacaine to the cells of an individual suffering from CML ex vivo. The treated cells are then reintroduced into the individual.

Example 57

Gene constructs useful in pharmaceutical kits and compositions for vaccination against and treatment for HBV are constructed with vectors described as backbones in Example 46. The plasmids contain HBV structural genes, particularly genes that encode HBV surface antigen and/or HBV core antigen core and/or HBV precore antigen.

Example 58

Gene constructs useful in pharmaceutical kits and compositions for vaccination against and treatment for HCV are constructed with vectors described as backbones in Example 46. The plasmids contain HCV structural genes, particularly genes that encode HCV core protein and/or HCV envelope protein.

Example 59

The gene construct pREV was designed which contains a nucleotide sequence that encodes HIV rev as the sole target protein. The coding sequence of rev is cloned into Backbone A described in Example 46 from BBG35 (RD Sytems Inc. Minneapolis, Minn.) which contains the coding region of rev from HIV strain HX3B in pUC19.

TABLE 1

| | |
|---|---|
| Picornavirus Family | |
| Genera: | Rhinoviruses: (Medical) responsible for ~50% cases of the common cold. Etheroviruses: (Medical) includes polioviruses, coxsackieviruses, echoviruses, and human enteroviruses such as hepatitis A virus. Apthoviruses: (Veterinary) these are the foot and mouth disease viruses. |
| Target antigens: | VP1, VP2, VP3, VP4, VPG |
| Calcivirus Family | |
| Genera: | Norwalk Group of Viruses: (Medical) these viruses are an important causative agent of epidemic gastroenteritis. |

TABLE 1-continued

Togavirus Family
    Genera:    Alphaviruses: (Medical and Veterinary) examples include Senilis viruses, RossRiver virus and Eastern & Western Equine encephalitis.
        Reovirus: (Medical) Rubella virus.
Flariviridue Family
        Examples include: (Medical) dengue, yellow fever, Japanese encephalitis, St. Louis encephalitis and tick borne encephalitis viruses.
Hepatitis C Virus: (Medical) these viruses are not placed in a family yet but are believed to be either a togavirus or a flavivirus. Most similarity is with togavirus family.
Coronavirus Family: (Medical and Veterinary)
        Infectious bronchitis virus (poultry)
        Porcine transmissible gastroenteric virus (pig)
        Porcine hemagglutinating encephalomyelitis virus (pig)
        Feline infectious peritonitis virus (cats)
        Feline enteric coronavirus (cat)
        Canine coronavirus (dog)
        The human respiratory coronaviruses cause ~40 cases of common cold. EX. 224E, 0C43
        Note - coronaviruses may cause non-A, B or C hepatitis
    Target antigens:
        E1 - also called M or matrix protein
        E2 - also called S or Spike protein
        E3 - also called HE or hemagglutin-elterose glycoprotein (not present in all coronaviruses)
        N - nucleocapsid
Rhabdovirus Family
    Genera:    Vesiliovirus
        Lyssavirus: (medical and veterinary) rabies
    Target antigen:    G protein
        N protein
Filoviridue Family: (Medical)
        Hemorrhagic fever viruses such as Marburg and Ebola virus
Paramyxovirus Family:
    Genera:    Paramyxovirus: (Medical and Veterinary) Mumps virus, New Castle disease virus (important pathogen in chickens)
        Morbillivirus: (Medical and Veterinary) Measles, canine distemper
        Pneuminvirus: (Medical and Veterinary) Respiratory syncytial virus
Orthomyxovirus Family (Medical)
        The Influenza virus
Bungavirus Family
    Genera:    Bungavirus: (Medical) California encephalitis, LA Crosse
        Phlebovirus: (Medical) Rift Valley Fever
        Hantavirus: Puremala is a hemahagin fever virus
        Nairvirus (Veterinary) Nairobi sheep disease
        Also many unassigned bungaviruses
Arenavirus Family (Medical)
        LCM, Lassa fever virus
Reovirus Family
    Genera:    Reovirus: a possible human pathogen
        Rotavirus: acute gastroenteritis in children
        Orbiviruses: (Medical and Veterinary) Colorado Tick fever, Lebombo (humans) equine encephalosis, blue tongue
Retrovirus Family
    Sub-Family:
        Oncorivirinal: (Veterinary) (Medical) feline leukemia virus, HTLVI and HTLVII
        Lentivirinal: (Medical and Veterinary) HIV, feline immunodeficiency virus, equine infections, anemia virus
        Spumavirinal
Papovavirus Family
    Sub-Family:
        Polyomaviruses: (Medical) BKU and JCU viruses
    Sub-Family:
        Papillomavirus: (Medical) many viral types associated with cancers or malignant progression of papilloma
Adenovirus (Medical)
        EX AD7, ARD., O.B. - cause respiratory disease - some adenoviruses such as 275 cause enteritis
Parvovirus Family (Veterinary)
        Feline parvovirus: causes feline enteritis
        Feline panleucopeniavirus
        Canine parvovirus
        Porcine parvovirus
Herpesvirus Family
    Sub-Family:    alphaherpesviridue
    Genera:    Simplexvirus (Medical)
        HSVI, HSVII
        Varicellovirus: (Medical - Veterinary) pseudorabies - varicella zoster
    Sub-Family -    betaherpesviridue
    Genera:    Cytomegalovirus (Medical)
        HCMV
        Muromegalovirus
    Sub-Family:    Gammaherpesviridue
    Genera:    Lymphocryptovirus (Medical)
        EBV - (Burkitts lympho)
        Rhadinovirus
Poxvirus Family
    Sub-Family:    Chordopoxviridue (Medical - Veterinary)
    Genera:    Variola (Smallpox)
        Vaccinia (Cowpox)
        Parapoxivirus - Veterinary
        Auipoxvirus - Veterinary
        Capripoxvirus
        Leporipoxvirus
        Suipoxvirus
    Sub-Family:    Entemopoxviridue
Hepadnavirus Family
        Hepatitis B virus
Unclassified
        Hepatitis delta virus

TABLE 2

Bacterial pathogens
    Pathogenic gram-positive cocci include: pneumococcal; staphylococcal; and streptococcal.
    Pathogenic gram-negative cocci include: meningococcal; and gonococcal.
    Pathogenic enteric gram-negative bacilli include: enterobacteriaceae; *pseudomonas*, acinetobacteria and *eikenella*; melioidosis; *salmonella*; shigellosis; hemophilus; chancroid; brucellosis; tularemia; *yersinia (pasteurella)*; *streptobacillus moniliformis* and *spirillum*; *listeria monocytogenes*; *erysipelothrix rhusiopathiae*; diphtheria; cholera; anthrax; donovanosis (granuloma inguinale); and bartonellosis.
    Pathogenic anaerobic bacteria include: tetanus; botulism; other *clostridia*; tuberculosis; leprosy; and other *mycobacteria*. Pathogenic spirochetal diseases include: syphilis; treponematoses: yaws, pinta and endemic syphilis; and leptospirosis.
    Other infections caused by higher pathogen bacteria and pathogenic fungi include: actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis.
    Rickettsial infections include rickettsial and rickettsioses.

| TABLE 2-continued |
|---|
| Examples of mycoplasma and chlamydial infections include: mycoplasma pneumoniae; lymphogranuloma venereum; psittacosis; and perinatal chlamydial infections.<br>Pathogenic eukaryotes<br>  Pathogenic protozoans and helminths and infections thereby include: amebiasis; malaria; leishmaniasis; trypanosomiasis; toxoplasmosis; pneumocystis carinii; babesiosis; giardiasis; trichinosis; filariasis; schistosomiasis; nematodes; trematodes or flukes; and cestode (tapeworm) infections. |

The invention claimed is:

1. A method of inducing an immune response against an antigen in an individual comprising the step of:
injecting into tissue of said individual at a site on said individual's body, a) a polynucleotide function enhancer and b) DNA molecules that comprise DNA sequences that encode said antigen and are operably linked to regulatory sequences which are functional in cells of said individual, wherein said DNA molecules are taken up by cells in said tissue and said antigen is produced by expression of said DNA sequence in said cells;
wherein said polynucleotide function enhancer is a compound having a formula selected from the group consisting of:

Ar—R$^1$—O—R$^2$—R$^3$,

Ar—N—R$^1$—R$^2$—R$^3$,

R$^4$—N—R$^5$—R$^6$, and

R$^4$—O—R$^1$—R$^7$ wherein:
Ar is benzene, p-aminobenzene, m-aminobenzene, o-aminobenzene, substituted benzene, substituted p-aminobenzene, substituted m-aminobenzene, substituted o-aminobenzene, wherein the amino group in the aminobenzene compounds can be amino, $C_1$-$C_5$ alkylamine, $C_1$-$C_5$, $C_1$-$C_5$ dialkylamine and substitutions in substituted compounds are halogen, $C_1$-$C_5$ alkyl and $C_1$-$C_5$ alkoxy;
R1 is C=O;
R2 is C1-C10 alkyl including branched alkyls;
R3 is hydrogen, amine, C1-C5 alkylamine, C1-C5, C1-C5 dialkylamine;
R2 and R3 can form a cyclic alkyl, a C1-C10 alkyl substituted cyclic alkyl, a cyclic aliphatic amine, a C1-C10 alkyl substituted cyclic aliphatic amine, a heterocycle, a C1-C10 alkyl substituted heterocycle including a C1-C10 alkyl N-substituted heterocycle;
R4 is Ar, R2 or C1-C5 alkoxy, a cyclic alkyl, a C1-C10 alkyl substituted cyclic alkyl, a cyclic aliphatic amine, a C1-C10 alkyl substituted cyclic aliphatic amine, a heterocycle, a C1-C10 alkyl substituted heterocycle and a C1-C10 alkoxy substituted heterocycle including a C1-C10 alkyl N-substituted heterocycle;
R5 is C=NH;
R6 is Ar, R2 or C1-C5 alkoxy, a cyclic alkyl, a C1-C10 alkyl substituted cyclic alkyl, a cyclic aliphatic amine, a C1-C10 alkyl substituted cyclic aliphatic amine, a heterocycle, a C1-C10 alkyl substituted heterocycle and a C1-C10 alkoxy substituted heterocycle including a C1-C10 alkyl N-substituted heterocycle; and,
R7 is Ar, R2 or C1-C5 alkoxy, a cyclic alkyl, a C1-C10 alkyl substituted cyclic alkyl, a cyclic aliphatic amine, a C1-C10 alkyl substituted cyclic aliphatic amine, a heterocycle, a C1-C10 alkyl substituted heterocycle and a C1-C10 alkoxy substituted heterocycle including a C1-C10 alkyl N-substituted heterocycle.

2. The method of claim 1 wherein said DNA molecules are plasmids.

3. The method of claim 1 wherein said tissue includes skin and muscle.

4. The method of claim 1 wherein said tissue is skin.

5. The method of claim 1 wherein said tissue is muscle.

6. The method of claim 5 wherein said tissue is skeletal muscle.

7. The method of claim 1 wherein said polynucleotide function enhancer is a compound having the formula Ar—R$^1$—O—R$^2$—R$^3$.

8. The method of claim 7 wherein said DNA molecule comprises a DNA sequence that encodes a protein, said DNA sequence being operatively linked to regulatory sequences which control the expression of said DNA sequence.

9. The method of claim 7 wherein said DNA molecules are plasmids.

10. The method of claim 7 wherein said tissue includes skin and muscle.

11. The method of claim 7 wherein said tissue is skin.

12. The method of claim 7 wherein said tissue is muscle.

13. The method of claim 12 wherein said tissue is skeletal muscle.

14. The method of claim 1 wherein said polynucleotide function enhancer is a compound having the formula Ar—R$^1$—O—R$^2$—R$^3$ or Ar—N—R$^1$—R$^2$—R$^3$.

15. The method of claim 1 wherein said antigen is an intracellular pathogen antigen.

16. The method of claim 1 wherein said antigen is a viral antigen.

17. The method of claim 15 wherein said antigen is of a virus selected from the group consisting of: human immunodeficiency virus, HIV; Human T cell leukemia virus, HTLV; influenza virus; hepatitis A virus; hepatitis B virus; hepatitis C virus; human papilloma virus, HPV; Herpes simplex 1 virus, HSV1; Herpes simplex 2 virus, HSV2; Cytomegalovirus, CMV; Epstein-Barr virus, EBR; rhinovirus; and, coronavirus.

18. The method of claim 1 wherein said immune response comprises inducing antibodies against said antigen in said individual.

19. The method of claim 18 wherein said polynucleotide function enhancer is a compound having the formula $Ar-R^1-O-R^2-R^3$.

20. The method of claim 18 wherein said DNA molecules are plasmids.

21. The method of claim 18 wherein said antigen is an intracellular pathogen antigen.

22. The method of claim 18 wherein said antigen is a viral antigen.

23. The method of claim 22 wherein said viral antigen is of a virus selected from the group consisting of: human immunodeficiency virus, HIV; Human T cell leukemia virus, HTLV; influenza virus; hepatitis A virus; hepatitis B virus; hepatitis C virus; human papilloma virus, HPV; Herpes simplex 1 virus, HSV1; Herpes simplex 2 virus, HSV2; Cytomegalovirus, CMV; Epstein-Barr virus, EBR; rhinovirus; and, coronavirus.

24. The method of claim 18 wherein said tissue includes skin and muscle.

25. The method of claim 18 wherein said tissue is skin.

26. The method of claim 18 wherein said tissue is muscle.

27. The method of claim 26 wherein said tissue is skeletal muscle.

28. The method of claim 18 wherein said polynucleotide function enhancer is a compound having the formula $Ar-R^1-O-R^2-R^3$ or $Ar-N-R^1-R^2-R^3$.

* * * * *

SEQUENCE LISTING

<160> NUMBER OF SEQ ID NOS: 52

<210> SEQ ID NO 1
<211> LENGTH: 32
<212> TYPE: DNA
<213> ORGANISM: Artificial
<220> FEATURE:
<223> OTHER INFORMATION: Oligonucleotide

<400> SEQUENCE: 1
aggcgtctcg agacagagga gagcaagaaa tg					32

<210> SEQ ID NO 2
<211> LENGTH: 30
<212> TYPE: DNA
<213> ORGANISM: Artificial
<220> FEATURE:
<223> OTHER INFORMATION: Oligonucleotide

<400> SEQUENCE: 2
tttccctcta gataagccat ccaatcacac					30

<210> SEQ ID NO 3
<211> LENGTH: 29
<212> TYPE: DNA
<213> ORGANISM: Artificial
<220> FEATURE:
<223> OTHER INFORMATION: Oligonucleotide

<400> SEQUENCE: 3
gaaggatcca tgaaaaaata tttattggg					29

<210> SEQ ID NO 4
<211> LENGTH: 30
<212> TYPE: DNA
<213> ORGANISM: Artificial
<220> FEATURE:
<223> OTHER INFORMATION: Oligonucleotide

<400> SEQUENCE: 4
actgtcgact tattttaaag cgtttttaag					30

<210> SEQ ID NO 5
<211> LENGTH: 30
<212> TYPE: DNA
<213> ORGANISM: Artificial
<220> FEATURE:
<223> OTHER INFORMATION: Oligonucleotide

<400> SEQUENCE: 5
gccagttttg gatccttaaa aaaggcttgg					30

<210> SEQ ID NO 6
<211> LENGTH: 27
<212> TYPE: DNA
<213> ORGANISM: Artificial

-continued

<220> FEATURE:
<223> OTHER INFORMATION: Oligonucleotide

<400> SEQUENCE: 6
ttgtgaggga cagaattcca atcaggg                                          27

<210> SEQ ID NO 7
<211> LENGTH: 24
<212> TYPE: DNA
<213> ORGANISM: Artificial
<220> FEATURE:
<223> OTHER INFORMATION: Oligonucleotide

<400> SEQUENCE: 7
cagtgatatc ccgggagact cctc                                             24

<210> SEQ ID NO 8
<211> LENGTH: 25
<212> TYPE: DNA
<213> ORGANISM: Artificial
<220> FEATURE:
<223> OTHER INFORMATION: Oligonucleotide

<400> SEQUENCE: 8
gaatagaaga actcctctag aattc                                            25

<210> SEQ ID NO 9
<211> LENGTH: 27
<212> TYPE: DNA
<213> ORGANISM: Artificial
<220> FEATURE:
<223> OTHER INFORMATION: Oligonucleotide

<400> SEQUENCE: 9
gccttaggcg gatcctatgg caggaag                                          27

<210> SEQ ID NO 10
<211> LENGTH: 24
<212> TYPE: DNA
<213> ORGANISM: Artificial
<220> FEATURE:
<223> OTHER INFORMATION: Oligonucleotide

<400> SEQUENCE: 10
taagatgggt ggccatggtg aatt                                             24

<210> SEQ ID NO 11
<211> LENGTH: 22
<212> TYPE: PRT
<213> ORGANISM: Artificial Sequence
<220> FEATURE:
<223> OTHER INFORMATION: chemically synthesized peptide

<400> SEQUENCE: 11

Cys Asn Thr Arg Lys Arg Ile Arg Ile Gln Arg Gly Pro Gly Arg Ala
1               5                   10                  15

Phe Val Thr Ile Gly Lys
            20

<210> SEQ ID NO 12
<211> LENGTH: 25
<212> TYPE: PRT
<213> ORGANISM: Artificial Sequence
<220> FEATURE:
<223> OTHER INFORMATION: chemically synthesized peptide

<400> SEQUENCE: 12

Tyr Asn Lys Arg Lys Arg Ile His Ile Gln Arg Gly Pro Gly Arg Ala
1               5                   10                  15

Phe Tyr Thr Thr Lys Asn Ile Ile Cys
            20                  25

<210> SEQ ID NO 13
<211> LENGTH: 27
<212> TYPE: PRT
<213> ORGANISM: Artificial Sequence
<220> FEATURE:
<223> OTHER INFORMATION: chemically synthesized peptide

<400> SEQUENCE: 13

Cys Arg Ile Lys Gln Phe Ile Asn Met Trp Gln Glu Val Gly Lys Ala
1               5                   10                  15

Met Thr Ala Pro Pro Ile Ser Gly Ile Arg Cys
            20                  25

<210> SEQ ID NO 14
<211> LENGTH: 26
<212> TYPE: PRT
<213> ORGANISM: Artificial Sequence
<220> FEATURE:
<223> OTHER INFORMATION: chemically synthesized peptide

<400> SEQUENCE: 14

Arg Ile Leu Ala Val Glu Arg Tyr Ile Lys Asp Gln Gln Leu Leu Gly
1               5                   10                  15

Ile Trp Gly Cys Ser Gly Lys Leu Ile Cys
            20                  25

<210> SEQ ID NO 15
<211> LENGTH: 27
<212> TYPE: DNA
<213> ORGANISM: Artificial
<220> FEATURE:
<223> OTHER INFORMATION: Oligonucleotide

<400> SEQUENCE: 15
ttgtttaact tttgatcgat ccattcc                                              27

<210> SEQ ID NO 16
<211> LENGTH: 21
<212> TYPE: DNA
<213> ORGANISM: Artificial
<220> FEATURE:
<223> OTHER INFORMATION: Oligonucleotide

<400> SEQUENCE: 16
gatttgtatc gatgatctga c                                                    21

<210> SEQ ID NO 17
<211> LENGTH: 25
<212> TYPE: DNA
<213> ORGANISM: Artificial
<220> FEATURE:
<223> OTHER INFORMATION: Oligonucleotide

<400> SEQUENCE: 17
tgtagtagca aaagaaatag ttaag                                                25

<210> SEQ ID NO 18
<211> LENGTH: 25
<212> TYPE: DNA
<213> ORGANISM: Artificial

```
<220> FEATURE:
<223> OTHER INFORMATION: Oligonucleotide

<400> SEQUENCE: 18
aattcttaac tatttctttt gctac                                            25

<210> SEQ ID NO 19
<211> LENGTH: 40
<212> TYPE: DNA
<213> ORGANISM: Artificial
<220> FEATURE:
<223> OTHER INFORMATION: Oligonucleotide

<400> SEQUENCE: 19
atttgtcgac tggtttcagc ctgccatggc aggaagaagc                            40

<210> SEQ ID NO 20
<211> LENGTH: 29
<212> TYPE: DNA
<213> ORGANISM: Artificial
<220> FEATURE:
<223> OTHER INFORMATION: Oligonucleotide

<400> SEQUENCE: 20
acgacgcgta ttctttagct cctgactcc                                        29

<210> SEQ ID NO 21
<211> LENGTH: 24
<212> TYPE: DNA
<213> ORGANISM: Artificial
<220> FEATURE:
<223> OTHER INFORMATION: Oligonucleotide

<400> SEQUENCE: 21
gctgacggta gcggccgcac aatt                                             24

<210> SEQ ID NO 22
<211> LENGTH: 22
<212> TYPE: DNA
<213> ORGANISM: Artificial
<220> FEATURE:
<223> OTHER INFORMATION: Oligonucleotide

<400> SEQUENCE: 22
gtattaagcg gccgcaattg tt                                               22

<210> SEQ ID NO 23
<211> LENGTH: 78
<212> TYPE: DNA
<213> ORGANISM: Artificial
<220> FEATURE:
<223> OTHER INFORMATION: Oligonucleotide

<400> SEQUENCE: 23
aaaaagcttc gcggatccgc gttgcggccg caacccgtca ccggcgacgc gtcggtcgac      60
cggtcatggc tgggcccc                                                    78

<210> SEQ ID NO 24
<211> LENGTH: 29
<212> TYPE: DNA
<213> ORGANISM: Artificial
<220> FEATURE:
<223> OTHER INFORMATION: Oligonucleotide

<400> SEQUENCE: 24
cccaagctta gacatgataa gatacattg                                        29
```

<210> SEQ ID NO 25
<211> LENGTH: 22
<212> TYPE: DNA
<213> ORGANISM: Artificial
<220> FEATURE:
<223> OTHER INFORMATION: Oligonucleotide

<400> SEQUENCE: 25
ctagcagctg gatcccagct tc                                            22

<210> SEQ ID NO 26
<211> LENGTH: 24
<212> TYPE: DNA
<213> ORGANISM: Artificial
<220> FEATURE:
<223> OTHER INFORMATION: Oligonucleotide

<400> SEQUENCE: 26
ggatttctgg ggatccaagc tagt                                          24

<210> SEQ ID NO 27
<211> LENGTH: 31
<212> TYPE: DNA
<213> ORGANISM: Artificial
<220> FEATURE:
<223> OTHER INFORMATION: Oligonucleotide

<400> SEQUENCE: 27
tataggatcc gcgcaatgaa agaccccacc t                                  31

<210> SEQ ID NO 28
<211> LENGTH: 31
<212> TYPE: DNA
<213> ORGANISM: Artificial
<220> FEATURE:
<223> OTHER INFORMATION: Oligonucleotide

<400> SEQUENCE: 28
atatggatcc gcaatgaaag accccgctg a                                   31

<210> SEQ ID NO 29
<211> LENGTH: 30
<212> TYPE: DNA
<213> ORGANISM: Artificial
<220> FEATURE:
<223> OTHER INFORMATION: Oligonucleotide

<400> SEQUENCE: 29
taaagcggcc gctcctatgg caggaagacg                                    30

<210> SEQ ID NO 30
<211> LENGTH: 34
<212> TYPE: DNA
<213> ORGANISM: Artificial
<220> FEATURE:
<223> OTHER INFORMATION: Oligonucleotide

<400> SEQUENCE: 30
attacgcgtc ttatgcttct agccaggcac aatg                               34

<210> SEQ ID NO 31
<211> LENGTH: 40
<212> TYPE: DNA
<213> ORGANISM: Artificial
<220> FEATURE:
<223> OTHER INFORMATION: Oligonucleotide

```
<400> SEQUENCE: 31
attacgcgtt tattacagaa tggaaaacag atggcaggtg                    40

<210> SEQ ID NO 32
<211> LENGTH: 32
<212> TYPE: DNA
<213> ORGANISM: Artificial
<220> FEATURE:
<223> OTHER INFORMATION: Oligonucleotide

<400> SEQUENCE: 32
attacgcgtt attgcagaat tcttattatg gc                            32

<210> SEQ ID NO 33
<211> LENGTH: 38
<212> TYPE: DNA
<213> ORGANISM: Artificial
<220> FEATURE:
<223> OTHER INFORMATION: Oligonucleotide

<400> SEQUENCE: 33
gaggcttgga gaggattata gaagtactgc aagagctg                      38

<210> SEQ ID NO 34
<211> LENGTH: 39
<212> TYPE: DNA
<213> ORGANISM: Artificial
<220> FEATURE:
<223> OTHER INFORMATION: Oligonucleotide

<400> SEQUENCE: 34
gaatcctctc caagcctcag ctactgctat agctctggc                     39

<210> SEQ ID NO 35
<211> LENGTH: 39
<212> TYPE: DNA
<213> ORGANISM: Artificial
<220> FEATURE:
<223> OTHER INFORMATION: Oligonucleotide

<400> SEQUENCE: 35
aaaaataaag cggccgctcc tatgccagga agagaagcg                     39

<210> SEQ ID NO 36
<211> LENGTH: 39
<212> TYPE: DNA
<213> ORGANISM: Artificial
<220> FEATURE:
<223> OTHER INFORMATION: Oligonucleotide

<400> SEQUENCE: 36
aaaaaattac gcgtcttatg cttctagcca ggcacaatg                     39

<210> SEQ ID NO 37
<211> LENGTH: 31
<212> TYPE: DNA
<213> ORGANISM: Artificial
<220> FEATURE:
<223> OTHER INFORMATION: Oligonucleotide

<400> SEQUENCE: 37
cccaagcttg ggaatgctct gccagtgtta c                             31

<210> SEQ ID NO 38
<211> LENGTH: 36
```

```
<212> TYPE: DNA
<213> ORGANISM: Artificial
<220> FEATURE:
<223> OTHER INFORMATION: Oligonucleotide

<400> SEQUENCE: 38
gggggccgga agggcacaat aaaactgtct gcttac                                36

<210> SEQ ID NO 39
<211> LENGTH: 33
<212> TYPE: DNA
<213> ORGANISM: Artificial
<220> FEATURE:
<223> OTHER INFORMATION: Oligonucleotide

<400> SEQUENCE: 39
cctgattcag gtgaaaatat tgttgatgcg ctg                                   33

<210> SEQ ID NO 40
<211> LENGTH: 111
<212> TYPE: DNA
<213> ORGANISM: Artificial
<220> FEATURE:
<223> OTHER INFORMATION: Oligonucleotide

<400> SEQUENCE: 40
aacatcaata caacctatta atttcccctc gtcaaaaata aggttatcaa gtgagaaatc      60
accatcagtg acgactgaat ccggtgagaa tggcaaaagt ttatgcattt c              111

<210> SEQ ID NO 41
<211> LENGTH: 55
<212> TYPE: DNA
<213> ORGANISM: Artificial
<220> FEATURE:
<223> OTHER INFORMATION: Oligonucleotide

<400> SEQUENCE: 41
ctagcgcggg gatccgcgtt gcggccgcaa aaagtcgacg ggcgacgcgt aaaaa           55

<210> SEQ ID NO 42
<211> LENGTH: 55
<212> TYPE: DNA
<213> ORGANISM: Artificial
<220> FEATURE:
<223> OTHER INFORMATION: Oligonucleotide

<400> SEQUENCE: 42
gatcttttta cgcgtcgccc gtcgactttt tgcgcccgca acgcggatcc ccgcg           55

<210> SEQ ID NO 43
<211> LENGTH: 38
<212> TYPE: DNA
<213> ORGANISM: Artificial
<220> FEATURE:
<223> OTHER INFORMATION: Oligonucleotide

<400> SEQUENCE: 43
atgtcgactg gtttcagcct gccatggcag gaagaagc                             38

<210> SEQ ID NO 44
<211> LENGTH: 35
<212> TYPE: DNA
<213> ORGANISM: Artificial
<220> FEATURE:
<223> OTHER INFORMATION: Oligonucleotide

<400> SEQUENCE: 44
```

```
ccccacgacg cgtctattct ttagctcctg actcc                              35
```

<210> SEQ ID NO 45
<211> LENGTH: 35
<212> TYPE: DNA
<213> ORGANISM: Artificial
<220> FEATURE:
<223> OTHER INFORMATION: Oligonucleotide

<400> SEQUENCE: 45

```
tttgccgccg cgtaagtgga gagagatggt gcgag                              35
```

<210> SEQ ID NO 46
<211> LENGTH: 21
<212> TYPE: DNA
<213> ORGANISM: Artificial
<220> FEATURE:
<223> OTHER INFORMATION: Oligonucleotide

<400> SEQUENCE: 46

```
ctggtggggc tgttggctct g                                             21
```

<210> SEQ ID NO 47
<211> LENGTH: 79
<212> TYPE: DNA
<213> ORGANISM: Artificial
<220> FEATURE:
<223> OTHER INFORMATION: Oligonucleotide

<400> SEQUENCE: 47

```
aatttaataa gtaagtaagt gtcatatgtt tgtttgaatt ctgcaacaac tgctgtttat   60
ccattttcag aattgggtg                                                79
```

<210> SEQ ID NO 48
<211> LENGTH: 79
<212> TYPE: DNA
<213> ORGANISM: Artificial
<220> FEATURE:
<223> OTHER INFORMATION: Oligonucleotide

<400> SEQUENCE: 48

```
tcgacaccca attctgaaaa tggataaaca gcacttgttg cagaattcaa acaaacatat   60
gacacttact tacttatta                                                79
```

<210> SEQ ID NO 49
<211> LENGTH: 41
<212> TYPE: DNA
<213> ORGANISM: Artificial
<220> FEATURE:
<223> OTHER INFORMATION: Oligonucleotide

<400> SEQUENCE: 49

```
ggggtttttg ggcatatgta tagggggacaa ttggagaagt g                      41
```

<210> SEQ ID NO 50
<211> LENGTH: 70
<212> TYPE: DNA
<213> ORGANISM: Artificial
<220> FEATURE:
<223> OTHER INFORMATION: Oligonucleotide

<400> SEQUENCE: 50

```
aagcttgtgg aattcttaat ttctctgtcc ggggtttttg ggcatatgta tgagggacat   60
tggacaagtg                                                          70
```

```
<210> SEQ ID NO 51
<211> LENGTH: 19
<212> TYPE: DNA
<213> ORGANISM: Artificial
<220> FEATURE:
<223> OTHER INFORMATION: Oligonucleotide

<400> SEQUENCE: 51
cagtatctgg catgggtac                                               19

<210> SEQ ID NO 52
<211> LENGTH: 19
<212> TYPE: DNA
<213> ORGANISM: Artificial
<220> FEATURE:
<223> OTHER INFORMATION: Oligonucleotide

<400> SEQUENCE: 52
ccatgccaga tactggtac                                               19
```